United States Patent [19]
Biller et al.

[11] Patent Number: 5,712,279
[45] Date of Patent: Jan. 27, 1998

[54] INHIBITORS OF MICROSOMAL TRIGLYCERIDE TRANSFER PROTEIN AND METHOD

[75] Inventors: Scott A. Biller, Hopewell; John K. Dickson, Eastampton, both of N.J.; R. Michael Lawrence, Yardley, Pa.; David R. Magnin, Hamilton; Michael A. Poss, Lawrenceville, both of N.J.; Jeffrey A. Robl, Newtown, Pa.; Richard B. Sulsky, Franklin Park; Joseph A. Tino, Lawrenceville, both of N.J.

[73] Assignee: Bristol-Myers Squibb Company, Princeton, N.J.

[21] Appl. No.: 548,811

[22] Filed: Jan. 11, 1996

Related U.S. Application Data

[63] Continuation-in-part of Ser. No. 472,067, Jun. 6, 1995, which is a continuation-in-part of Ser. No. 391,901, Feb. 21, 1995, abandoned.

[51] Int. Cl.$^6$ .............. C07D 211/98; C07D 409/06; C07D 405/06; A61K 31/445
[52] U.S. Cl. .............. 514/252; 546/208; 546/202; 546/198; 546/193; 546/189; 546/201; 546/194; 546/196; 546/187; 546/244; 546/212; 546/214; 546/200; 546/224; 546/203; 546/205; 546/199; 546/213; 546/141; 514/325; 514/324; 514/321; 514/318; 514/316; 514/259; 514/235.5; 514/255; 514/228.8; 514/323; 514/320; 514/232.8; 514/309; 514/329; 544/287; 544/130; 544/360; 544/88; 544/405; 544/364; 544/238; 544/391; 544/399
[58] Field of Search ................ 546/208, 202, 546/198, 193, 189, 201; 514/325, 324, 321, 318, 316, 259, 235.5, 255, 228.8, 323, 252; 544/287, 130, 360, 88, 405

[56] References Cited

U.S. PATENT DOCUMENTS

| | | | |
|---|---|---|---|
| 3,910,931 | 10/1975 | Cavalla et al. | 546/206 |
| 4,289,781 | 9/1981 | Bengtsson et al. | 424/267 |
| 4,576,940 | 3/1986 | Tahara et al. | 514/212 |
| 4,581,355 | 4/1986 | Tahara et al. | 514/212 |
| 4,607,042 | 8/1986 | Pierce | 514/323 |
| 5,032,598 | 7/1991 | Baldwin et al. | 514/318 |
| 5,130,333 | 7/1992 | Pan et al. | 514/460 |
| 5,189,045 | 2/1993 | Peglion et al. | 514/319 |
| 5,215,989 | 6/1993 | Baldwin et al. | 514/252 |
| 5,527,801 | 6/1996 | Masuda et al. | 514/255 |

FOREIGN PATENT DOCUMENTS

| | | |
|---|---|---|
| 0584446A2 | 3/1994 | European Pat. Off. |
| 0643057A1 | 3/1995 | European Pat. Off. |
| WO9305778 | 4/1993 | WIPO |
| WO94/40640 | 12/1996 | WIPO |

OTHER PUBLICATIONS

Wetterau, J. and Zilversmit, D.B., J. Biol. Chem. 259, 10863–10866 (1984), "1 Triglyceride and Cholesteryl Ester Transfer Protein Associated with Liver Microsomes".

Wetterau, J., Grant Application entitled: "Intracellular Triglyceride Transport and Metabolism". Presentation Materials, Aspen Bile Acid/Cholesterol Conference, Aug. 15, 1992.

Wetterau, J. R., et al., Science, vol. 258, 999–1001, Nov. 6, 1992, "Absence of Microsomal Triglyceride Transfer Protein in Individuals with Abetalipoproteinemia".

Archibald, J. L., et al., Journal of Medicinal Chemistry, vol. 14, No. 11, pp. 1054–1059.

Cortizo, L. et al., J. Med. Chem., 34, pp. 2242–2247, 1991.

Hall, I. H. et al., Pharmaceutical Research, vol. 9, No. 10, pp. 1324–1329, 1992.

Hall, I. H., et al., Pharmacological Research Communications, vol. 19, No. 12, pp. 839–858, 1987.

Murthy et al., Eur. J. Med. Chem.—Chim. Ther., vol. 20, No. 6, pp. 547–550, 1985.

Derwent Abstract No. 93-117225/14.

Bulleid & Freedman, Nature 335, 649–651 (1988). "Defective co-translational formation of disulphide bonds in protein disulphideisomerase-deficient microsomes".

Koivu et al., J. Biol. Chem. 262, 6447–6449 (1987). "A Single Polypeptide Acts Both as the β Subunit of Prolyl 4-Hydroxylase and as a Protein Disulfide-Isomerase".

Kane & Havel in the Metabolic Basis of Inherited Disease, Sixth Edition, 1139–1164 (1989). "Disorders of the Biogenesis and Secretion of Lipoproteins Containing The B Apolipoproteins".

Schaerer et al., Clin. Chem. 34, B9–B12 (1988). "Genetics and Abnormalties in Metabolism of Lipoproteins".

Drayna et al., Nature 327, 632–634 (1987). "Cloning and sequencing of human cholesteryl ester transfer protein cDNA".

(List continued on next page.)

*Primary Examiner*—Mukund J. Shah
*Assistant Examiner*—King Lit Wong
*Attorney, Agent, or Firm*—Burton Rodney

[57] ABSTRACT

Compounds are provided which inhibit microsomal triglyceride transfer protein and thus are useful for lowering serum lipids and treating atherosclerosis and related diseases. The compounds have the structure wherein Z, $X^1$, $X^2$, x and $R^5$ are as defined herein.

19 Claims, No Drawings

OTHER PUBLICATIONS

Pihlajaniemi et al., EMBO J. 6, 643–649 (1987). "Molecular cloning of the β–subunit of human prolyl 4–hydroxylase. This subunit and protein disulphide isomerase are products of the same gene".

Yamaguchi et al., Biochem. Biophys. Res. Comm. 146, 1485–1492 (1987). "Sequence of Membrane–Associated Thyroid Hormone Binding Protein From Bovine Liver: Its Identity with Protein Disulphide Isomerase".

Edman et al., Nature 317, 267–270 (1985). "Sequence of protein disulphide isomerase and implications of its relationship to thioredoxin".

Kao et al., Connective Tissue Research 18, 157–174 (1988). "Isolation of cDNA Clones and Genomic DNA Clones of β–Subunit of Chicken Prolyl 4–Hydroxylase".

Wetterau, J. et al., Biochem 30, 9728–9735 (1991). "Protein Disulfide Isomerase Appears Necessary To Maintain the Catalytically Active Structure of the Microsomal Triglyceride Transfer Protein".

Morton, R.E. et al., J. Biol. Chem. 256, 1992–1995 (1981). "A Plasma Inhibitor of Triglyceride and Chloesteryl Ester Transfer Activities".

Wetterau, J. et al., Biochem. 30, 4406–4412 (1991): "Structural Properties of the Microsomal Triglyceride–Transfer Protein Complex".

Wetterau, J. et al., J. Biol. Chem. 265, 9800–9807 (1990). "Protein Disulfide Isomerase Is a Component of the Microsomal Triglyceride Transfer Protein Complex".

Wetterau, J. and Zilversmit, D.B., Chem. and Phys. of Lipids 38, 205–22 (1985). "Purification and Characterization of Microsomal Triglyceride and Cholesteryl Ester Transfer Protein From Bovine Liver Microsomes".

Wetterau, J. and Zilversmit, D.B., Biochimica et Biophysica Acta 875, 610–617 (1986). "Localization of intracellular triacylglycerol and cholesteryl ester transfer activity in rat tissues".

INHIBITORS OF MICROSOMAL TRIGLYCERIDE TRANSFER PROTEIN AND METHOD

CROSS-REFERENCE TO RELATED APPLICATIONS

This is a continuation-in-part of application Ser. No. 472,067 filed Jun. 6, 1995, which is a continutation-in-part of application Ser. No. 391,901 filed Feb. 21, 1995, now abandoned each of which is hereby incorporated by reference.

FIELD OF THE INVENTION

This invention relates to novel compounds which inhibit microsomal triglyceride transfer protein, and to methods for decreasing serum lipids and treating atherosclerosis employing such compounds.

BACKGROUND OF THE INVENTION

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, *Chem. Phys. Lipids* 38, 205–22 (1985). When transfer rates are expressed as the percent of the donor lipid transferred per time, MTP expresses a distinct preference for neutral lipid transport (TG and CE), relative to phospholipid transport. The protein from bovine liver has been isolated and characterized. Wetterau & Zilversmit, *Chem. Phys. Lipids* 38, 205–22 (1985). Polyacrylamide gel electrophoresis (PAGE) analysis of the purified protein suggests that the transfer protein is a complex of two subunits of apparent molecular weights 58,000 and 88,000, since a single band was present when purified MTP was electrophoresed under nondenaturing condition, while two bands of apparent molecular weights 58,000 and 88,000 were identified when electrophoresis was performed in the presence of sodium dodecyl sulfate (SDS). These two polypeptides are hereinafter referred to as 58 kDa and 88 kDa, respectively, or the 58 kDa and the 88 kDa component of MTP, respectively, or the low molecular weight subunit and the high molecular weight subunit of MTP, respectively.

Characterization of the 58,000 molecular weight component of bovine MTP indicates that it is the previously characterized multifunctional protein, protein disulfide isomerase (PDI). Wetterau et al., *J. Biol. Chem.* 265, 9800–7 (1990). The presence of PDI in the transfer protein is supported by evidence showing that (1) the amino terminal 25 amino acids of the bovine 58,000 kDa component of MTP is identical to that of bovine PDI, and (2) disulfide isomerase activity was expressed by bovine MTP following the dissociation of the 58 kDa–88 kDa protein complex. In addition, antibodies raised against bovine PDI, a protein which by itself has no TG transfer activity, were able to immunoprecipitate bovine TG transfer activity from a solution containing purified bovine MTP.

PDI normally plays a role in the folding and assembly of newly synthesized disulfide bonded proteins within the lumen of the endoplasmic reticulum. Bulleid & Freedman, *Nature* 335, 649–51 (1988). It catalyzes the proper pairing of cysteine residues into disulfide bonds, thus catalyzing the proper folding of disulfide bonded proteins. In addition, PDI has been reported to be identical to the beta subunit of human prolyl 4-hydroxylase. Koivu et al., *J. Biol. Chem.* 262, 6447–9 (1987). The role of PDI in the bovine transfer protein is not clear. It does appear to be an essential component of the transfer protein as dissociation of PDI from the 88 kDa component of bovine MTP by either low concentrations of a denaturant (guanidine HCl), a chaotropic agent (sodium perchlorate), or a nondenaturing detergent (octyl glucoside) results in a loss of transfer activity. Wetterau et al., *Biochemistry* 30, 9728–35 (1991). Isolated bovine PDI has no apparent lipid transfer activity, suggesting that either the 88 kDa polypeptide is the transfer protein or that it confers transfer activity to the protein complex.

The tissue and subcellular distribution of MTP activity in rats has been investigated. Wetterau & Zilversmit, *Biochem. Biophys. Acta* 875, 610–7 (1986). Lipid transfer activity was found in liver and intestine. Little or no transfer activity was found in plasma, brain, heart, or kidney. Within the liver, MTP was a soluble protein located within the lumen of the microsomal fraction. Approximately equal concentrations were found in the smooth and rough microsomes.

Abetalipoproteinemia is an autosomal recessive disease characterized by a virtual absence of plasma lipoproteins which contain apolipoprotein B (apoB). Kane & Havel in *The Metabolic Basis of Inherited Disease*, Sixth edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect has not been previously determined. In subjects examined, triglyceride, phospholipid, and cholesterol synthesis appear normal. At autopsy, subjects are free of atherosclerosis. Schaefer et al., *Clin. Chem.* 34, B9–12 (1988). A link between the apoB gene and abetalipoproteinemia has been excluded in several families. Talmud et al., *J. Clin. Invest.* 82, 1803–6 (1988) and Huang et al., *Am. J. Hum. Genet.* 46, 1141–8 (1990).

Subjects with abet alipoproteinemia are afflicted with numerous maladies. Kate & Havel, supra. Subjects have fat malabsorption and TG accumulation in their enterocytes and hepatocytes. Due to the absence of TG-rich plasma lipoproteins, there is a defect in the transport of fat-soluble vitamins such as vitamin E. This results in acanthocytosis of erythrocytes, spinocerebellar ataxia with degeneration of the fasciculus cuneatus and gracilis, peripheral neuropathy, degenerative pigmentary retinopathy, and ceroid myopathy. Treatment of abet alipoproteinemic subjects includes dietary restriction of fat intake and dietary supplementation with vitamins A, E and K.

In vitro, MTP catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, *Biochem. Biophys. Acta* 875, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Olofsson and colleagues have studied lipoprotein assembly in HepG2 cells. Bostrom et al., *J. Biol. Chem.* 263, 4434–42 (1988). Their results suggest small precursor lipoproteins become larger with time. This would be consistent with the addition or transfer of lipid molecules to nascent lipoproteins as they are assembled. MTP may play a role in this process. In support of this hypothesis, Howell and Palade, *J. Cell Biol.* 92, 833–45 (1982), isolated nascent lipoproteins from the hepatic Golgi fraction of rat liver. There was a spectrum of sizes of particles present with varying lipid and protein compositions. Particles of high density lipoprotein (HDL) density, yet containing apoB, were found. Higgins and Hutson, *J. Lipid Res.* 25, 1295–1305 (1984), reported lipoproteins isolated from Golgi were consistently larger than those from the endoplasmic reticulum, again suggesting the assembly of lipoproteins is a progressive event.

Recent reports (Science, Vol. 258, page 999, 1992; D. Sharp et. al., Nature, Vol. 365, page 65, 1993) demonstrate that the defect causing abet alipoproteinemia is in the MTP gene, and as a result, the MTP protein. Individuals with abet alipoproteinemia have no MTP activity, as a result of mutations in the MTP gene, some of which have been characterized. These results indicate that MTP is required for the synthesis of apoB containing lipoproteins, such as VLDL, the precursor to LDL. It therefore follows that inhibitors of MTP would inhibit the synthesis of VLDL and LDL, thereby lowering VLDL levels, LDL levels, cholesterol levels, and triglyceride levels in animals and man.

Canadian Patent Application No. 2,091,102 published Mar. 2, 1994 (corresponding to U.S. application Ser. No. 117,362, filed Sep. 3, 1993 (file DC21b)) reports MTP inhibitors which also block the production of apoB containing lipoproteins in a human hepatic cell line (HepG2 cells). This provides further support for the proposal that an MTP inhibitor would lower apoB containing lipoprotein and lipid levels in vivo. This Canadian patent application discloses a method for identifying the MTP inhibitors

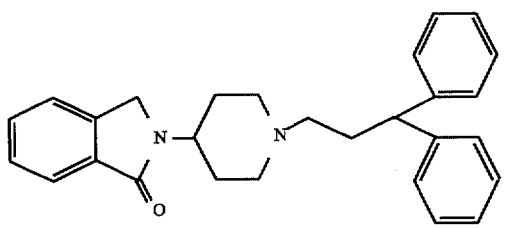

which has the name 2-[1-(3,3-diphenylpropyl)-4-piperidinyl]-2,3-dihydro-3-oxo-1H-isoindole hydrochloride and

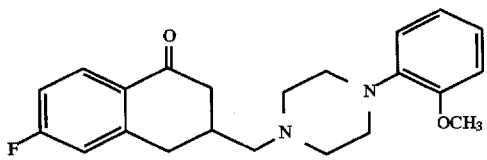

which has the name 1-[3-(6-fluoro-1-tetralanyl)methyl]-4-O-methoxyphenyl piperazine EP 0643057A1 published Mar. 15, 1995, discloses MTP inhibitors of the structure

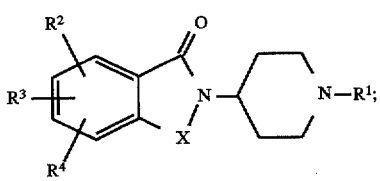

I or

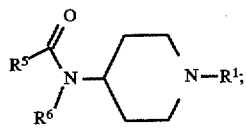

II or

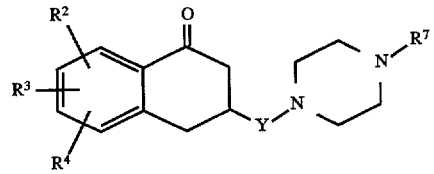

III where X is: $CHR^8$,

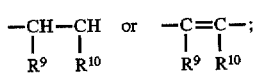

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is $-(CH_2)_m-$ or

where m is 2 or 3;

$R^1$ is alkyl, alkenyl, alkynyl, aryl, heteroaryl, arylalkyl (wherein alkyl has at least 2 carbons), diarylalkyl, arylalkenyl, diarylalkenyl, arylalkynyl, diarylalkynyl, diarylalkylaryl, heteroarylalkyl (wherein alkyl has at least 2 carbons), cycloalkyl, or cycloalkylalkyl (wherein alkyl has at least 2 carbons); all of the aforementioned $R^1$ groups being optionally substituted through available carbon atoms with 1, 2, or 3 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or $R^1$ is a group of the structure

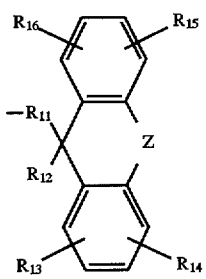

$R^{11}$ is a bond, alkylene, alkenylene or alkynylene of up to 6 carbon atoms, arylene (for example

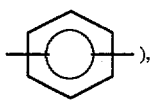

or mixed arylene-alkylene (for example

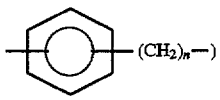

where n is 1 to 6;

$R^{12}$ is hydrogen, alkyl, alkenyl, aryl, heteroaryl, haloalkyl, arylalkyl, arylalkenyl, cycloalkyl, aryloxy, alkoxy, arylalkoxy, heteroarylalkyl or cycloalkylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, carboxy, aminocarbonyl, alkylcarbonyloxy, alkylcarbonylamino, arylalkyl, heteroaryl, heteroarylalkyl, or aryloxy;

or $R^1$ is

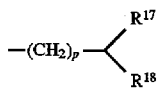

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

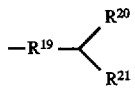

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, haloalkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl of at least 2 carbons, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloalkenylalkyl, polycycloalkenyl, polycycloalkenylalkyl, heteroarylcarbonyl, all of the $R^5$ and $R^6$ substituents being optionally substituted through available carbon atoms with 1, 2, or 3 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, or aryl or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino; with the proviso that when $R^5$ is $CH_3$, $R^6$ is not H; and where $R^5$ is phenyl, the phenyl preferably includes an ortho hydrophobic substituent such as alkyl, haloalkyl, aryl, aryloxy or arylalkyl;

$R^6$ is hydrogen or $C_1$-$C_4$ alkyl or $C_1$-$C_4$ alkenyl;

$R^7$ is alkyl, aryl or arylalkyl wherein alkyl or the alkyl portion is optionally substituted with oxo; and including pharmaceutically acceptable salts and anions thereof.

In the formula I compounds, where X is $CH_2$ and $R^2$, $R^3$ and $R^4$ are each H, $R^1$ will be other than 3,3-diphenylpropyl.

In the formula III compounds, where one of $R^2$, $R^3$ and $R^4$ is 6-fluoro, and the others are H, $R^7$ will be other than 4-O-methoxyphenyl.

U.S. application Ser. No. 472,067, filed Jun. 6, 1995 (file DC21e) discloses compounds of the structure

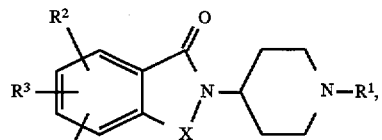

or

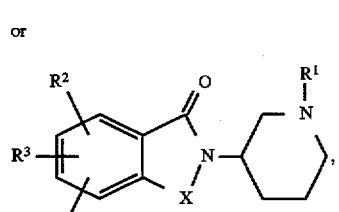

or

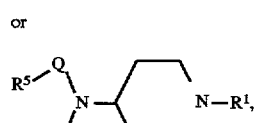

or

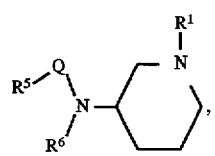

or

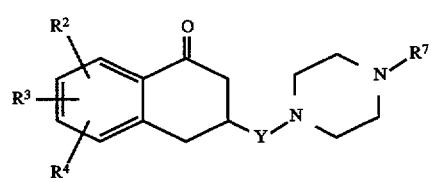

where Q is

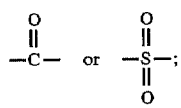

X is: CHR$^8$,

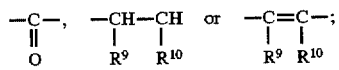

R$^8$, R$^9$ and R$^{10}$ are independently hydrogen, alkyl, alkenyl, alkynyl, aryl, arylalkyl, heteroaryl, heteroarylalkyl, cycloalkyl, or cycloalkylalkyl;

Y is —(CH$_2$)$_m$— or

wherein m is 2 or 3;

R$^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cyclo-alkylalkyl, heteroaryl, fluorenyl, heteroarylalkyl, hydroxy or oxo;

or R$^1$ is a fluorenyl-type group of the structure

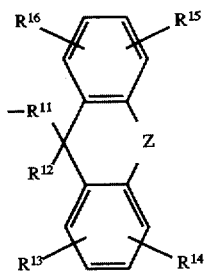   A or

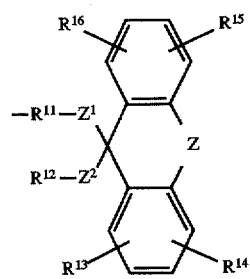   B or

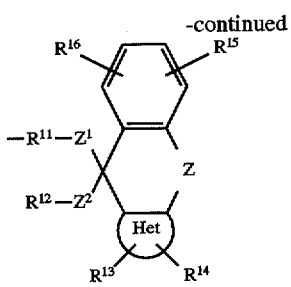   C or

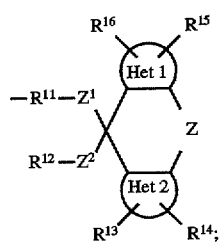   D or

R$^1$ is an indenyl-type group of the structure

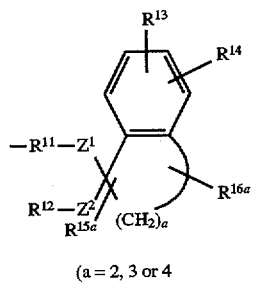   E (a = 2, 3 or 4)

or

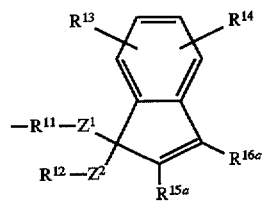   F or

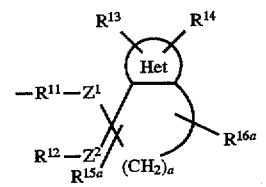   G or

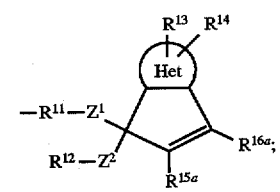   H $Z^1$ and $Z^2$ are the same or different and are independently a bond, O, S,

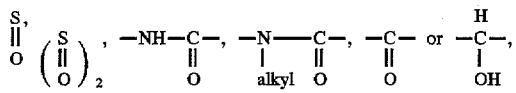

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl, with the provisos that (1) when $R^{12}$ is H, aryloxy, alkoxy or arylalkoxy, then $Z^2$ is

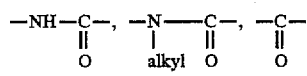

or a bond and (2) when $Z^2$ is a bond, $R^{12}$ cannot be heteroaryl or heteroarylalkyl;

Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

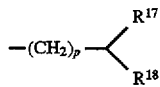

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

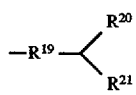

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1-C_4$ alkyl or $C_1-C_4$ alkenyl; all optionally substituted with 1, 2, 3 or 4 groups which may independently be any of the substituents listed in the definition of $R^5$ set out above;

$R^7$ is alkyl, aryl or arylalkyl wherein alkyl by itself or as part of arylalkyl is optionally substituted with oxo

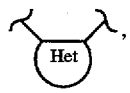

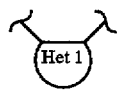

and

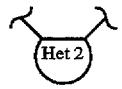

are the same or different and are independently selected from heteroaryl containing 5- or 6-ring members; and N-oxides

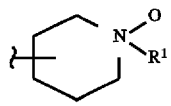

thereof; and pharmaceutically acceptable salts thereof;

with the provisos that where in the first formula X is $CH_2$, and $R^2$, $R^3$ and $R^4$ are each H, then $R^1$ will be other than 3,3-diphenylpropyl, and in the fifth formula, where one of $R^2$, $R^3$ and $R^4$ is 6-fluoro, and the others are H, $R^7$ will be other than 4-(2-methoxyphenyl).

SUMMARY OF THE INVENTION

In accordance with the present invention, novel compounds are provided which are inhibitors of MTP and have the structure

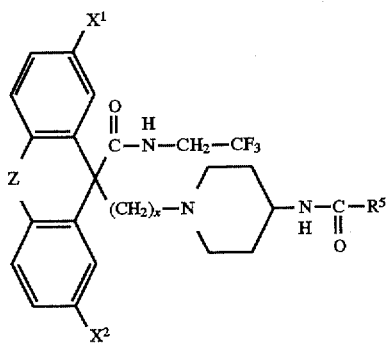

wherein Z is a bond, O or S;

$X^1$ and $X^2$ are independently H or halo, preferably F;

x is an integer from 2 to 6, preferably from 3 to 5, and $(CH_2)_x$ may be optionally substituted with 1, 2 or 3 substituents which are the same or different and are alkyl or halo; and $R^5$ is heteroaryl, aryl, heterocycloalkyl or cycloalkyl, each $R^5$ group being optionally substituted with 1, 2, 3 or 4 substituents which may be the same or different as defined hereinafter; and including piperidine N-oxides of the formula I compound, that is

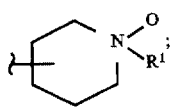

and including pharmaceutically acceptable salts thereof such as alkali met al salts such as lithium sodium or potassium, alkaline earth met al salts such as calcium or magnesium, as well as zinc or aluminum and other cations such as ammonium, choline, diethanolamine, ethylenediamine, t-butyl-amine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

The $R^5$ group may be substituted with 1, 2, 3 or 4 substituents, including (1) halogen such as Cl, F, $CF_3$, and I, (2) heteroaryl, including monocyclic or bicyclic ring systems, which includes 1, 2 or 3 heteroatoms which are S, N and/or O, and which includes from 2 to 10 carbons in the ring or ring system, such as

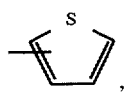

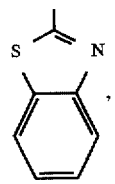

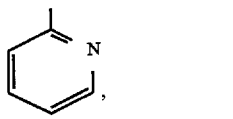

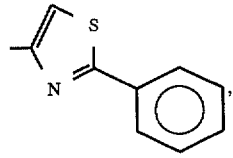

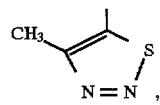

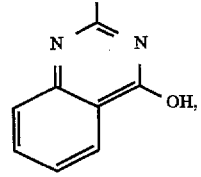

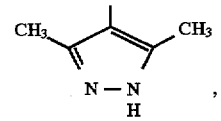

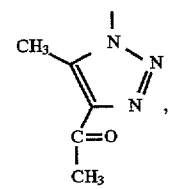

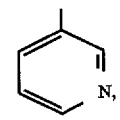

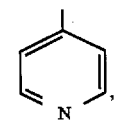

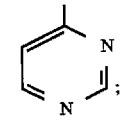

(3) heteroarylalkyl wherein heteroaryl is as defined above such as

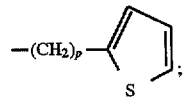

(4) cycloheteroalkyl which includes 1, 2 or 3 hetero atoms which are N, S or O in a monocyclic or bicyclic ring system such

[Structures: morpholine (N-linked with O), N-methylpiperazine (N-linked), piperidine (N-linked), 2-pyrrolidinone (N-linked)];

(5) alkyl;
(6) aryl such as phenyl, phenyl substituted with (a) halo, (b) alkyl, (c) CF$_3$O, (d) alkoxy (e)

$$-\mathrm{CH}(\mathrm{CF}_3)_2,$$

(f) CF$_3$, or (g) phenyl;
(7) alkylamino such as $$-\underset{\mathrm{H}}{\mathrm{N}}-(\mathrm{CH}_2)_p\mathrm{CF}_3-;$$

(8) alkyl (aryl) amino such as —N(CH$_3$)C$_6$H$_5$;
(9) alkythio such as —S—(CH$_2$)$_p$CF$_3$, $$-\mathrm{S}-\mathrm{CH}(\mathrm{CF}_3)_2,$$

—S—alkyl, $$-\mathrm{S}-(\mathrm{CH}_2)_p-\underset{\mathrm{O}}{\overset{\mathrm{O}}{\mathrm{S}}}-\mathrm{C}_6\mathrm{H}_5;$$

(10) alkoxy such as —O—(CH$_2$)$_p$—CF$_3$, $$-\mathrm{O}-\mathrm{CH}(\mathrm{CF}_3)_2,$$

OCH$_3$;
(11) cycloalkyl such as cyclohexyl;
(12) aryloxy such as

[—O—C$_6$H$_5$, —O—C$_6$H$_4$—Cl];

(13) amino;
(14) arylamino such as

[—NH—C$_6$H$_4$—CF$_3$];

(15) arylthio such as

[—S—C$_6$H$_4$—Cl, —S—C$_6$H$_3$(OCH$_3$)$_2$, —S—C$_6$H$_4$—OCH$_3$, —S—C$_6$H$_4$—CN];

(16) acyl such as (a) alkanoyl, such as $$-\overset{\mathrm{O}}{\underset{\|}{\mathrm{C}}}\mathrm{CH}_3,$$

(b) alkoxycarbonyl, such as $$-\overset{\mathrm{O}}{\underset{\|}{\mathrm{C}}}-\mathrm{O}-\mathrm{CF}_3,$$

(c) aroyl, such as $$-\overset{\mathrm{O}}{\underset{\|}{\mathrm{C}}}-\mathrm{C}_6\mathrm{H}_5, \quad -\overset{\mathrm{O}}{\underset{\|}{\mathrm{C}}}-\mathrm{C}_6\mathrm{H}_4-\mathrm{F},$$

(d) heteroarylaminocarbonyl, such as

[—C(O)—NH—CH$_2$-furyl, —C(O)—NH-(5-methylisoxazol-3-yl)], (e) arylalkyloxycarbonyl, such as $$-\overset{\mathrm{O}}{\underset{\|}{\mathrm{C}}}-\mathrm{O}-\mathrm{CH}_2\mathrm{C}_6\mathrm{H}_5;$$

(17) arylthioalkyl, such as —CH$_2$—S—C$_6$H$_5$;
(18) heteroarylamino, such as

[—NH-(3-CF$_3$-pyrazol-5-yl), —N(CH$_3$)—CH$_2$-pyridyl];

(19) arylalkyloxy, such as

[—O—CH$_2$—C$_6$H$_4$—F];

(20) heteroarylthio, such as

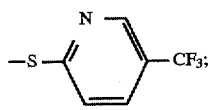

(21) heteroaryloxy, such as

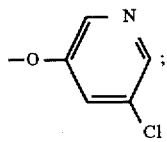

and

(22) arylsulfinyl, such as

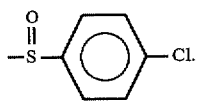

Thus, the compounds of formula I of the invention encompass compounds of the structure I$^a$

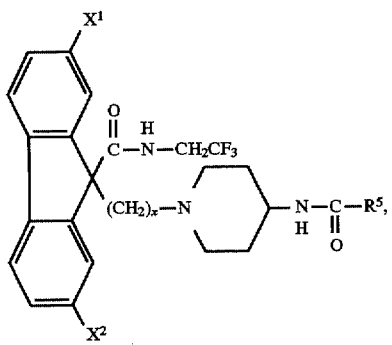

I$^b$

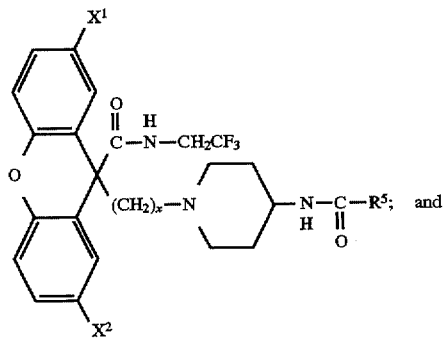

I$^c$

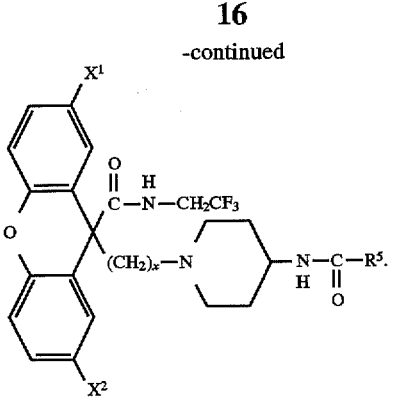

In addition, in accordance with the present invention, a method for preventing, inhibiting or treating atherosclerosis, pancreatitis or obesity is provided, wherein a compound of formula I as defined hereinbefore is administered in an amount which decreases the activity of microsomal triglyceride transfer protein.

Furthermore, in accordance with the present invention, a method is provided for lowering serum lipid levels, cholesterol and/or triglycerides, or inhibiting and/or treating hyperlipemia, hyperlipidemia, hyperlipoproteinemia, hypercholesterolemia and/or hypertriglyceridemia, wherein a compound of formula I as defined hereinbefore is administered in an amount which decreases the activity of microsomal triglyceride transfer protein.

DETAILED DESCRIPTION OF THE INVENTION

The following definitions apply to the terms as used throughout this specification, unless otherwise limited in specific instances.

The term "MTP" refers to a polypeptide or protein complex that (1) if obtained from an organism (e.g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., Nature 327, 632–634 (1987)] which may have similar catalytic properties. However, the MTP molecules of the present invention do not necessarily need to be catalytically active. For example, catalytically inactive MTP or fragments thereof may be useful in raising antibodies to the protein.

The phrase "stabilizing" atherosclerosis as used in the present application refers to slowing down the development of and/or inhibiting the formation of new atherosclerotic lesions.

The phrase "causing the regression of" atherosclerosis as used in the present application refers to reducing and/or eliminating atherosclerotic lesions.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4- dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, acyl, heteroaryl, heteroaryloxy, hetero-arylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio, as well as any of the other substituents as defined for $R^5$.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

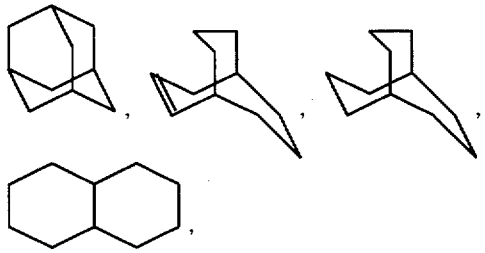

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio, as well as any of the other substituents as defined for $R^5$.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "polycycloalkyl" as employed herein alone or as part of another group refers to a bridged multicyclic group containing 5 to 20 carbons and containing 0 to 3 bridges, preferably 6 to 12 carbons and 1 or 2 bridges. Exemplary polycycloalkyl groups include [3.3.0]-bicyclo-octanyl, adamantanyl, [2.2.1]-bicycloheptanyl, [2.2.2]-bicyclooctanyl and the like and may be optionally substituted as defined for cycloalkyl.

The term "polycycloalkenyl" as employed herein alone or as part of another group refers to a bridged multicyclic group containing 5 to 20 carbons and containing 0 to 3 bridges and containing 1 or 2 double bonds, preferably 6 to 12 carbons and 1 or 2 bridges. Exemplary polycyclo-alkyl groups include [3.3.0]-bicyclooctenyl, [2.2.1]-bicycloheptenyl, [2.2.2]-bicyclooctenyl and the like and may be optionally substituted as defined for cycloalkyl.

The term "aryl" or "Ar" as employed herein alone or as part of another group refers to monocyclic and bicyclic aromatic groups containing 6 to 10 carbons in the ring portion (such as phenyl or naphthyl) and may optionally include one to three additional rings fused to Ar (such as aryl, cycloalkyl, heteroaryl or cycloheteroalkyl rings) and may be optionally substituted through available carbon atoms with 1, 2, 3 or 4 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of the substituents as defined for the $R^5$ group set out above.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl and/or aryl.

The term "lower alkylthio", "alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group as defined herein, refers to an organic radical linked to a carbonyl

group, examples of acyl groups include alkanoyl, alkenoyl, aroyl, aralkanoyl, heteroaroyl, cycloalkanoyl and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cyclo-alkyl, amino, hydroxy, heteroaryl, cycloheteroalkyl, alkanoylamino, alkylamido, arylcarbonylamino, nitro, cyano, thiol and/or alkylthio, as well as any of the other substituents as defined for $R^5$.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, as well as any of the other substituents as defined for $R^5$.

The term "alkylene" as employed herein alone or as part of another group (which also encompasses "alkyl" as part of another group such as arylalkyl or heteroarylalkyl) refers to alkyl groups as defined above having single bonds for attachment to other groups at two different carbon atoms and may optionally be substituted as defined above for "alkyl". The definition of alkylene applies to an alkyl group which links one function to another, such as an arylalkyl substituent.

The terms "alkenylene" and "alkynylene" as employed herein alone or as part of another group (which also encompass "alkenyl" or "alkynyl" as part of another group such as arylalkenyl or arylalkynyl), refer to alkenyl groups as defined above and alkynyl groups as defined above, respectively, having single bonds for attachment at two different carbon atoms.

Suitable $(CH_2)_x$ (were x is 2 to 6, preferably 3 to 5) or $(CH_2)_p$ groups (where p is 1 to 8, preferably 1 to 5) (which may include alkylene, alkenylene or alkynylene groups) as defined herein, may optionally include 1, 2, or 3 alkyl or halogen and in addition, may have one of the carbon atoms in the chain replaced with an oxygen atom, N—H, N—alkyl or N—aryl.

Examples of $(CH_2)_x$ and $(CH_2)_p$ groups include

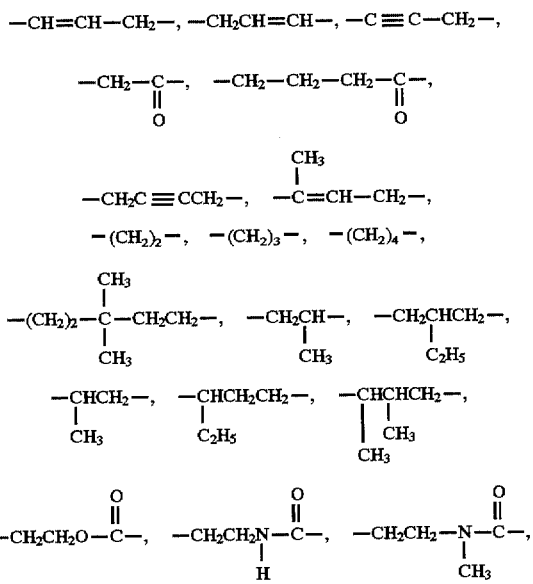

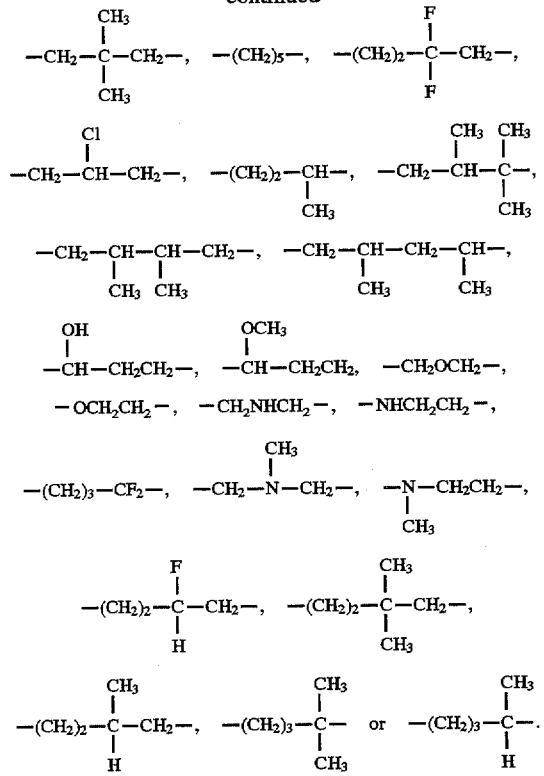

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" or "heterocycloalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

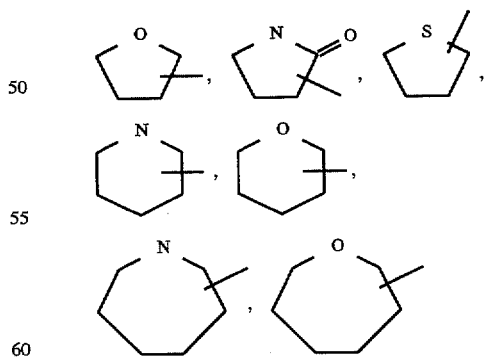

and the like. The above groups may include 1 to 3 substituents such as for any of $R^5$ groups as defined above. In addition, any of the above rings can be fused to 1 or 2 cycloalkyl, aryl, heteroaryl or cycloheteroalkyl rings.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), linked through a carbon atom or a heteroatom, where possible, optionally via the linker $(CH_2)_p$ (which is defined above), such as

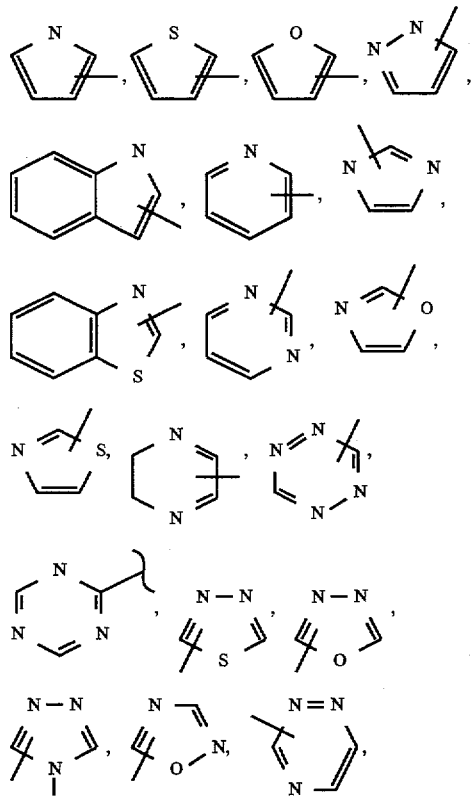

and the like, and includes all possible N-oxide derivatives.

The heteroaryl groups including the above groups may optionally include 1 to 4 substituents such as any of the substituents listed for aryl, or those substituents indicated for $R^5$ group as defined above. In addition, any of the above rings can be fused to a cycloalkyl, aryl, heteroaryl or cycloheteroalkyl ring.

The term "cycloheteroalkylalkyl" or "heterocycloalkylalkyl" as used herein alone or as part of another group refers to cycloheteroalkyl groups as defined above linked through a C atom or heteroatom to a $-(CH_2)_p-$ chain.

The term "heteroarylalkyl" or "heteroarylalkenyl" as used herein alone or as part of another group refers to a heteroaryl group as defined above linked through a C atom or heteroatom to a $-(CH_2)_p-$ chain, alkylene or alkenylene as defined above.

Preferred are compounds of formula I where Z is a bond;

$X^1$ and $X^2$ are H;

$R^5$ is aryl such as phenyl substituted with (1) aryl such as phenyl,

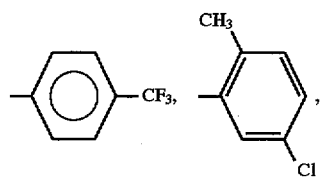

(2) heteroaryl such as

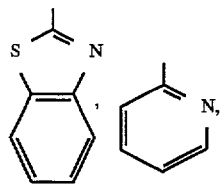

(3) halo such as Cl
$R^5$ is heteroaryl such as

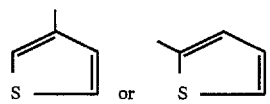

substituted with (1) aroyl such as

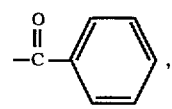

(2) arylthio such as

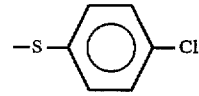

wherein the $R^5$ substituent is preferably in the position adjacent to the carbon linked to

$(CH_2)_x$ is $-(CH_2)_4-$ or

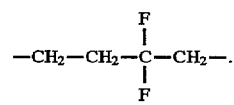

Most preferred are compounds of the structure (including salts thereof such as the monohydrochloride or dihydrochloride)

9-[4-[4-[[2-(2,2,2-Trifluoroethoxy)benzoyl]amino]-1-piperidinyl]butyl]-N-(2,2,2-trifluoroethyl)-9H-fluorene-9-carboxamide

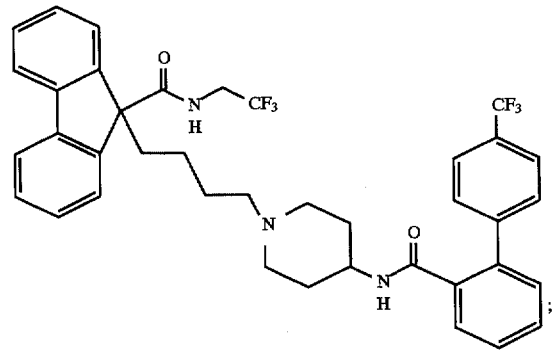

9-[4-[4-[([1,1-Biphenyl]-4-ylcarbonyl)amino]-1-piperidinyl]-3,3-difluorobutyl]-N-(2,2,2-trifluoroethyl)-9H-fluorene-9-carboxamide

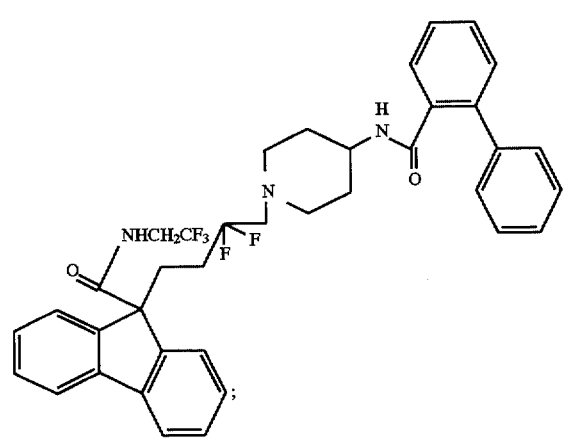

9-[4-[4-[(2-Pyridinylbenzoyl)amino)amino]-1-piperidinyl]-butyl]-N-(2,2,2-trifluoroethyl)-9H-fluorene-9-carboxamide

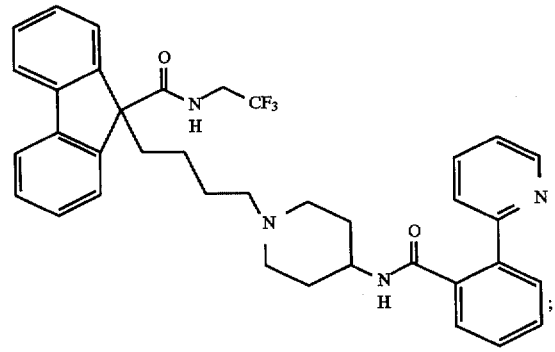

9-[4-[4-[[2-(2-Benzothiazolyl)benzoyl]amino]-1-piperidinyl]butyl]-N-(2,2,2-trifluoroethyl)-9H-fluorene-9-carboxamide

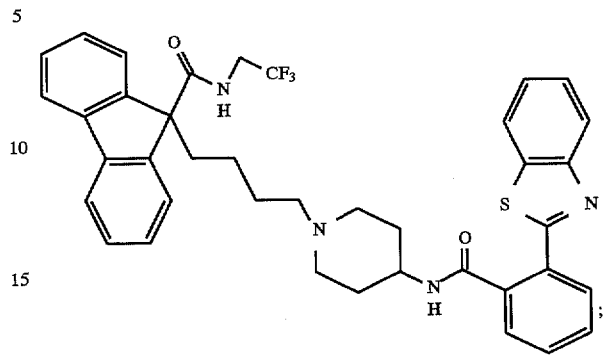

9-[4-[4-[[(4'-Chloro-[1,1'-biphenyl]-2-yl)carbonyl]-amino]-1-piperidinyl]butyl]-N-(2,2,2-trifluoroethyl)-9H-fluorene-9-carboxamide

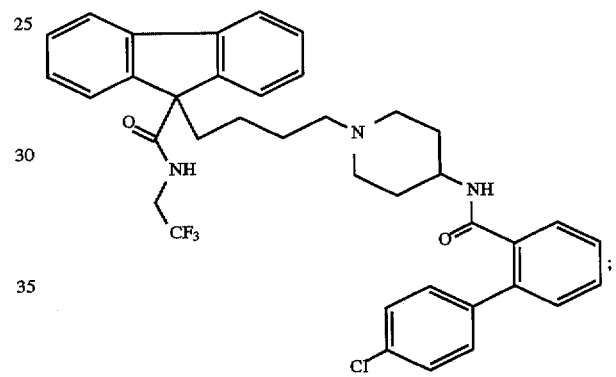

9-[4-[4-[[[1-(Phenylmethyl)-2-piperidinyl]carbonyl]-amino]-1-piperidinyl]butyl]-N-(2,2,2-trifluoroethyl)-9H-fluorene-9-carboxamide

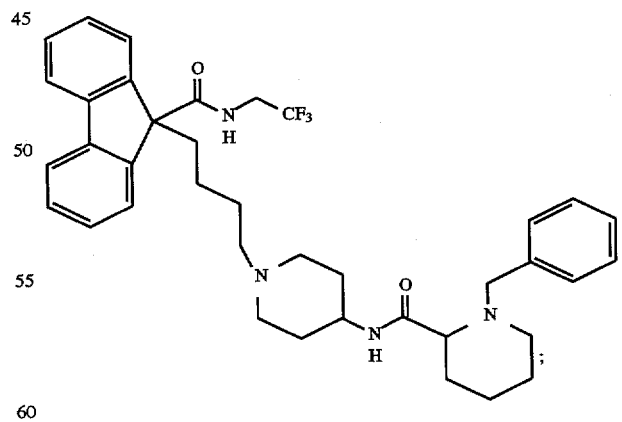

9-[4-[-[[(4,4'-Difluoro[1,1'-biphenyl]-2-yl)carbonyl]amino]-1-piperidinyl]butyl]-N-(2,2,2-trifluoroethyl)-9H-fluorene-9-carboxamide

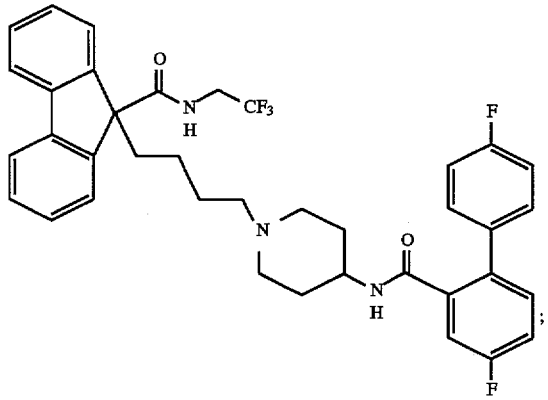

9-[4-[4-[[(4-Chloro[1,1-biphenyl]-2-yl)carbonyl]amino]-1-piperidinyl]butyl]-N-(2,2,2-trifluoroethyl)-9H-fluorene-9-carboxamide

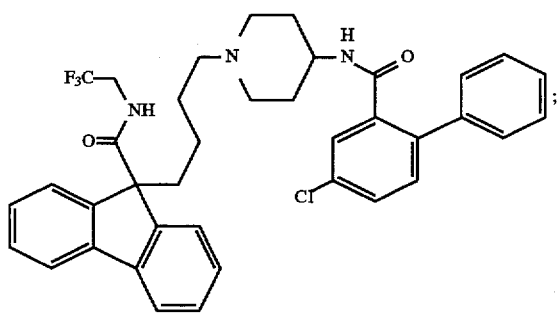

N-(2,2,2-Trifluoroethyl)-9-[4-[4-[[[4-(trifluoromethyl)[1,1-biphenyl]-2-yl]carbonyl]amino]-1-piperidinyl]butyl]-9H-fluorene-9-carboxamide

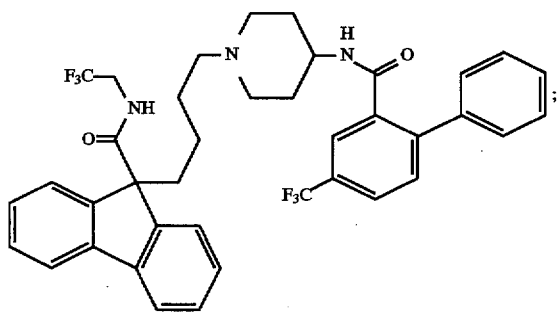

9-[4-[4-[[2-Chloro-5-(trifluoromethyl)benzoyl]amino]-1-piperidinyl]butyl]-N-(2,2,2-trifluoroethyl)-9H-fluorene-9-carboxamide, N-oxide

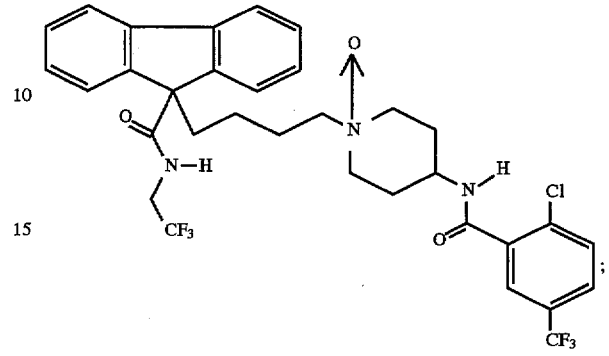

9-[4-[4-[(5-Chloro-2-methylbenzoyl)amino]-1-piperidinyl]butyl]-N-(2,2,2-trifluoroethyl)-9H-fluorene-9-carboxamide

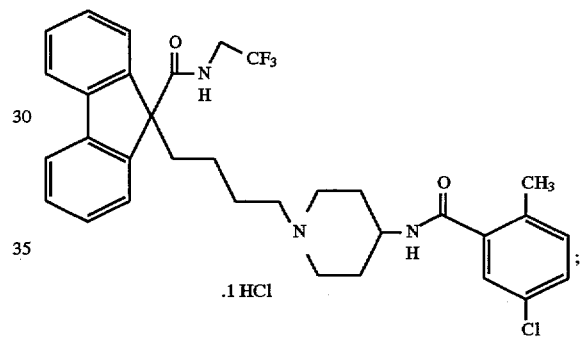

.1 HCl

N-(2,2,2-Trifluoroethyl)-9-[4-[4-[[[4'-(trifluoromethyl)[1,1-biphenyl]-2-yl]carbonyl]amino]-1-piperidinyl]butyl]-9H-fluoroene-9-carboxamide, N-oxide

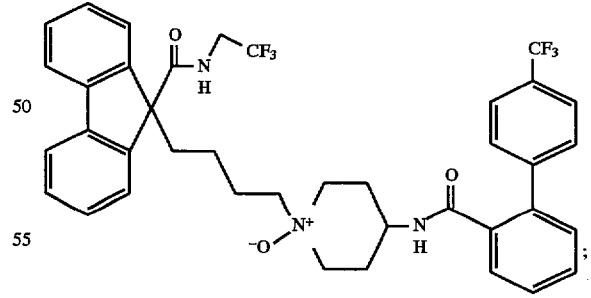

9-[4-[4-[[2-(2-Benzothiazolyl)benzoyl]amino]-1-piperidinyl]butyl]-N-(2,2,2-trifluoroethyl)-9H-fluorene-9-carboxamide, N-oxide

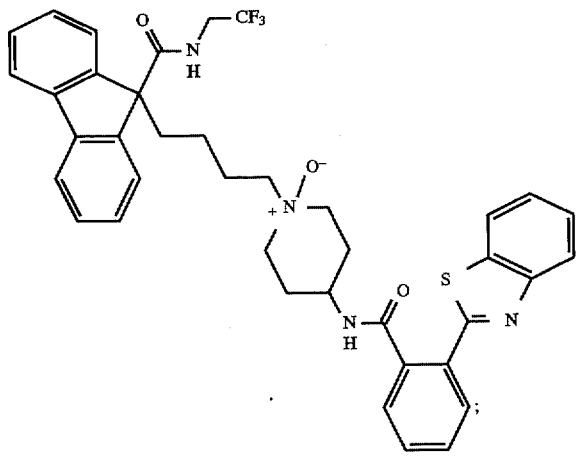

9-[4-[4-[(5-Chloro-2-methylbenzoyl)amino]-1-piper-idinyl]butyl]-N-(2,2,2-trifluoroethyl)-9H-fluorene-9-carboxamide, N'-oxide

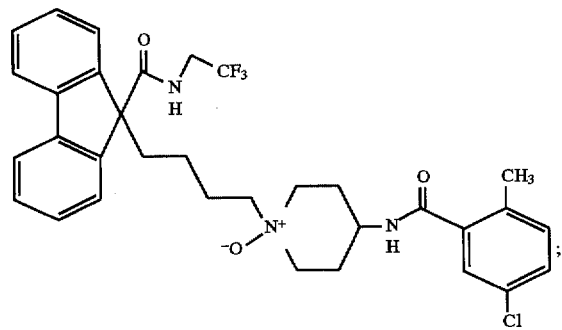

9-[4-[4-[[[4-Chloro-4'-(trifluoromethyl)[1,1'-biphenyl]-2-yl]-carbonyl]amino]-1-piperidinyl]butyl]-N-(2,2,2-trifluoroethyl)-9H-fluorene-9-carboxamide

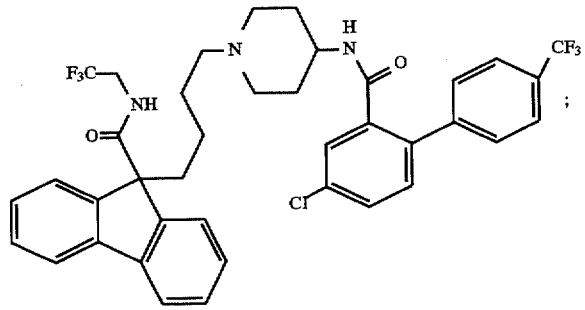

9-[4-[4-[[[4-Chloro-4'-(trifluoromethyl)[1,1'-biphenyl]-2-yl]carbonyl]amino]-1-piperidinyl]butyl]-N-(2,2,2-trifluoroethyl)-9H-fluorene-9-carboxamide, N-oxide

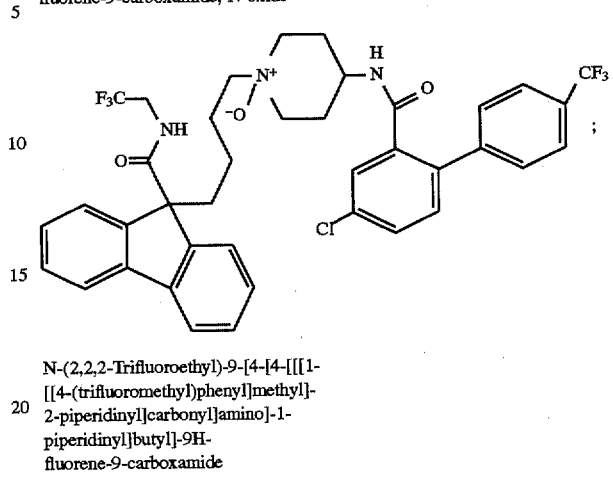

N-(2,2,2-Trifluoroethyl)-9-[4-[4-[[[1-[[4-(trifluoromethyl)phenyl]methyl]-2-piperidinyl]carbonyl]amino]-1-piperidinyl]butyl]-9H-fluorene-9-carboxamide

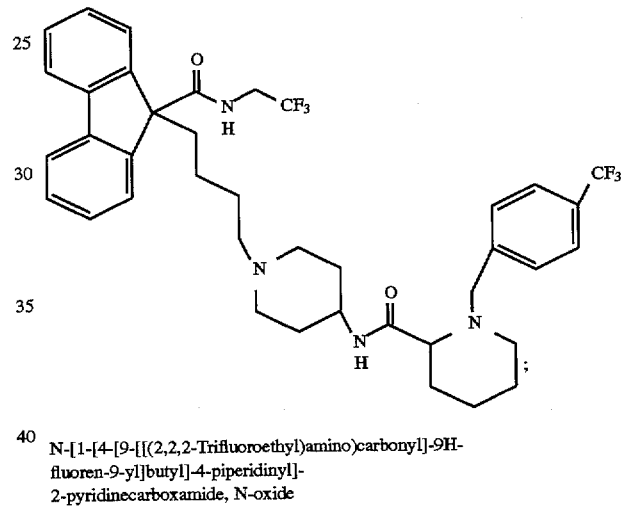

N-[1-[4-[9-[[(2,2,2-Trifluoroethyl)amino]carbonyl]-9H-fluoren-9-yl]butyl]-4-piperidinyl]-2-pyridinecarboxamide, N-oxide

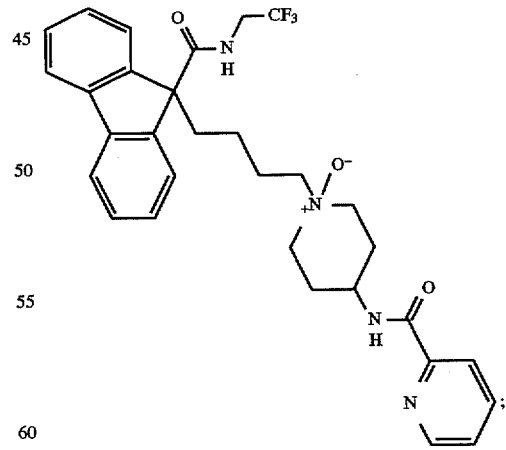

-continued

9-[4-[4-[[[1-(Cyclohexylmethyl)-2-piperidinyl]-
carbonyl]amino]-1-piperidinyl]-butyl]-
N-(2,2,2-trifluoroethyl)-9H-fluorene-9-carboxamide

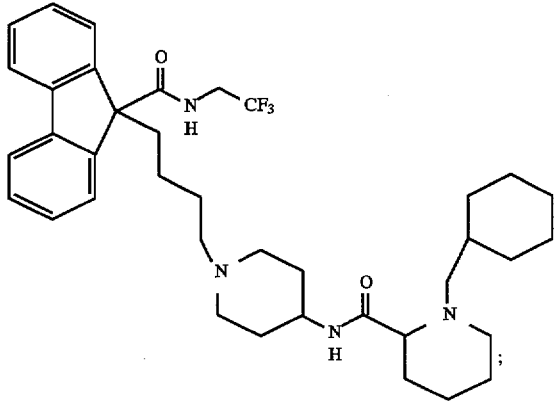

9-[4-[4-[[(3-Cyclohexyl-2-pyridinyl)carbonyl]amino]-1-
piperidinyl]butyl]-N-(2,2,2-trifluoroethyl)-
9H-fluorene-9-carboxamide

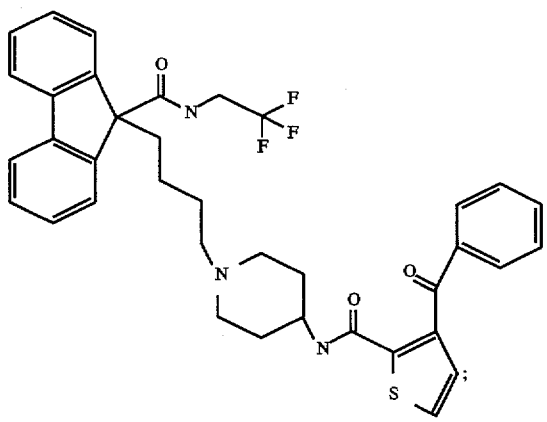

9-[4-[4-[[(4'-Fluoro-[1,1'-biphenyl]-2-
yl)carbonyl]amino]-1-piperidinyl]butyl]-
N-(2,2,2-trifluoroethyl)-9H-fluorene-9-carboxamide

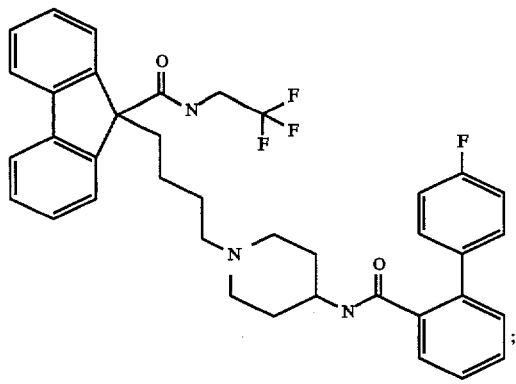

-continued

9-[4-[4-[(2,5-Dichlorobenzoyl)amino]-1-
piperidinyl]butyl]-N-(2,2,2-trifluoroethyl)-
9H-fluorene-9-carboxamide

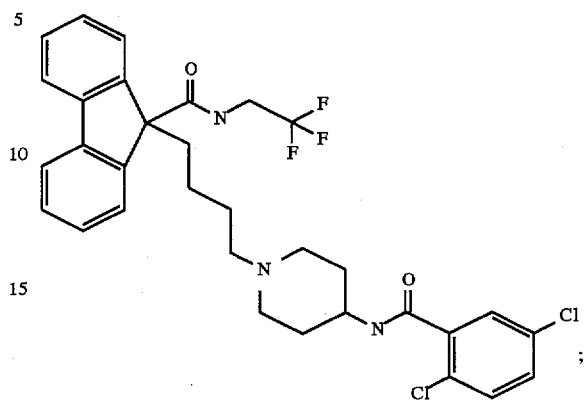

9-[4-[4-[[2-Chloro-5-(trifluoromethyl)benzoyl]amino]-
1-piperidinyl]butyl]-N-(2,2,2-trifluoroethyl)-
9H-fluorene-9-carboxamide

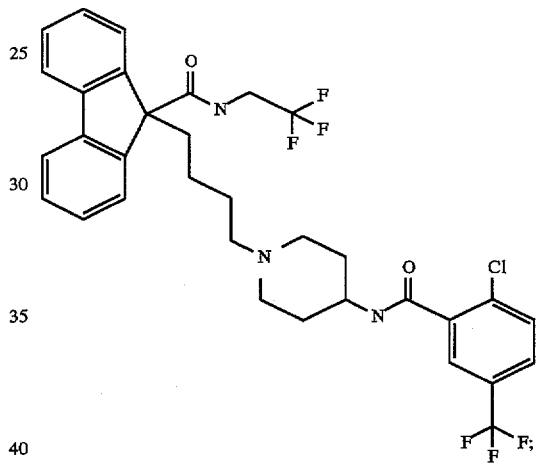

9-[4-[4-[[[4-[(4-Chlorophenyl)thio]-3-
thienyl]carbonyl]amino]-1-piperidinyl]butyl]-
N-(2,2,2-trifluoroethyl)-9H-fluorene-9-carboxamide

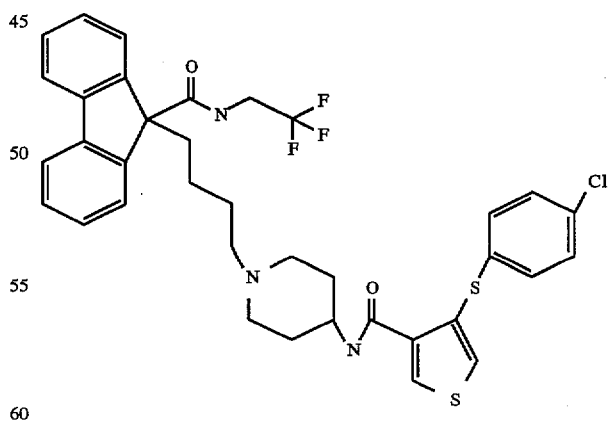

It is to be understood that combinations of substituents which lead to chemically unstable molecules are not included within the scope of the present invention; for example, compounds of the invention will not include —O—O—, —O—C—OH, N—C—OH and —S—C—OH linkages.

The compounds of formula I, may be prepared by the exemplary processes described in the following reaction schemes. Exemplary reagents and procedures for these reactions appear hereinafter and in the working Examples.

In the following reaction schemes $R^1$ is

Scheme I
General Routes

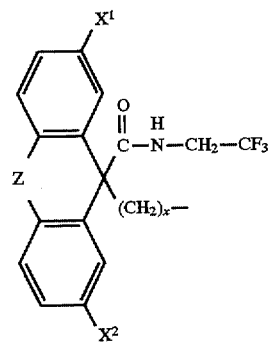

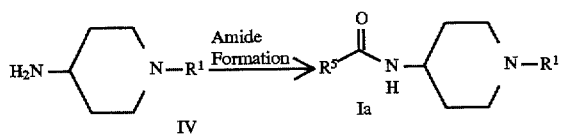

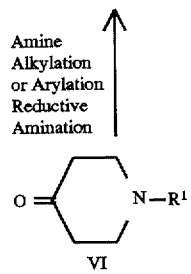

Scheme II
General Routes to Starting Materials

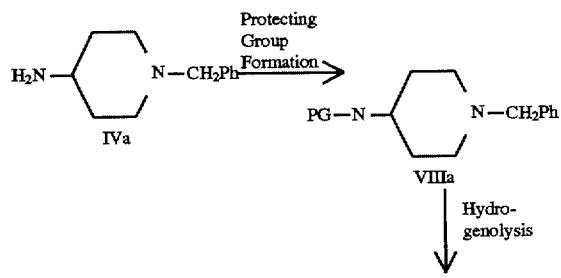

Scheme II
General Routes to Starting Materials

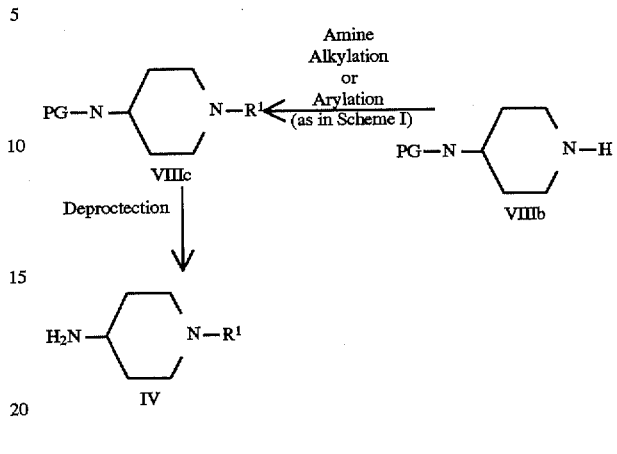

Scheme III
Preparation of Compound I
(Robotic Amide Coupling)

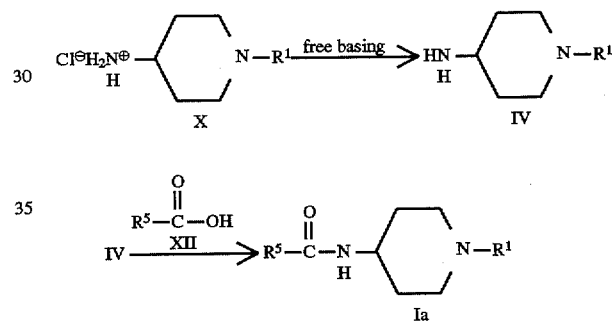

Scheme IV
Preparation of Intermediates
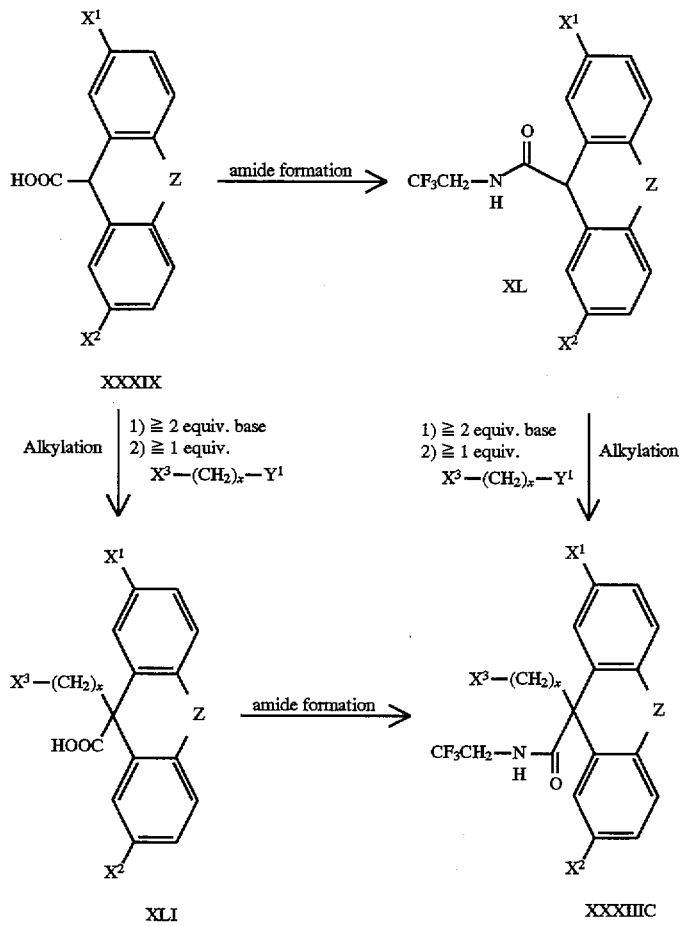
$X^3$, $Y^1$ are same or different halo or Osulfonate
Scheme V
General Route to Final Product
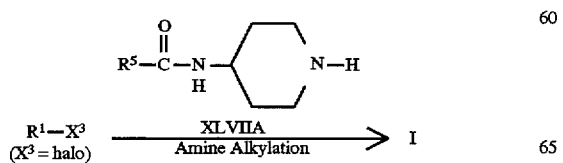

Scheme VI
General Route to Final Product I

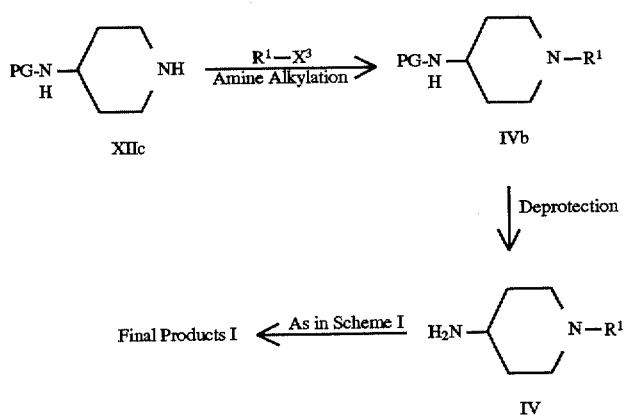

(Example of a protected nitrogen (PG-N) is the t-BuOC=ONH (BOC amino) group, which can be deprotected under mild conditions, such as anhydrous HCl in dioxane or neat trifluoroacetic acid).

Scheme VII
Preparation of Halide Intermediates (where $(CH_2)_x$ is $(CH_2)_4$)

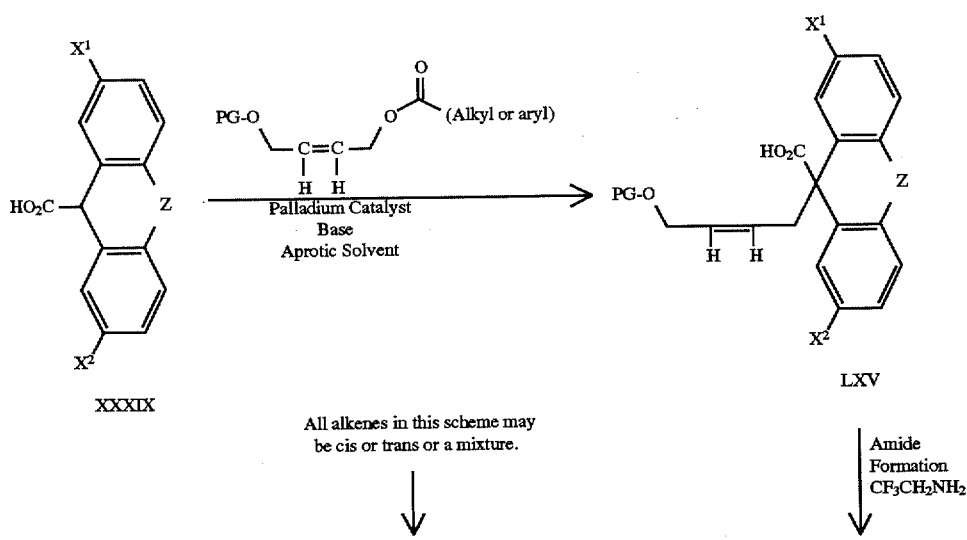

All alkenes in this scheme may be cis or trans or a mixture.

Amide Formation
$CF_3CH_2NH_2$

-continued
Scheme VII
Preparation of Halide Intermediates (where $(CH_2)_x$ is $(CH_2)_4$)

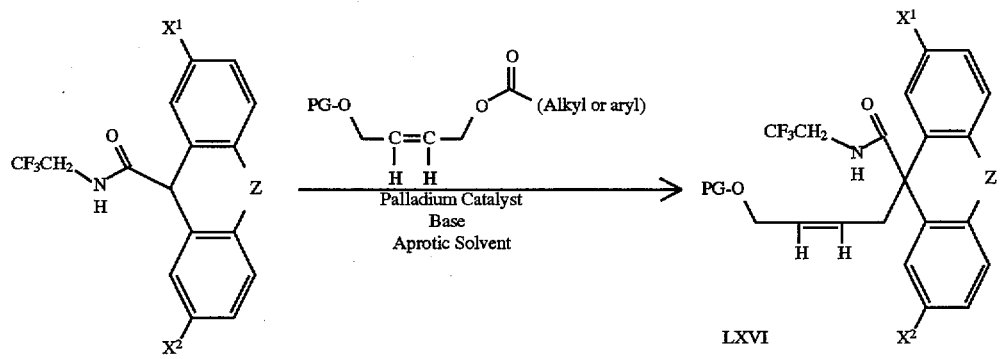

XL

For example: Palladium catalyst can be $Pd(Ph_3P)_4$,
base can be NaH or bis(trimethylsilyl)acetamide,
aprotic solvent can be THF or DMF or mixtures.
PG- can be organosilyl such as $t\text{-}Bu(Ph)_2Si\text{-}$,
and deprotection conditions can be $n\text{-}Bu_4NF$, THF.

LXVI

↓ Deprotection

LXVII

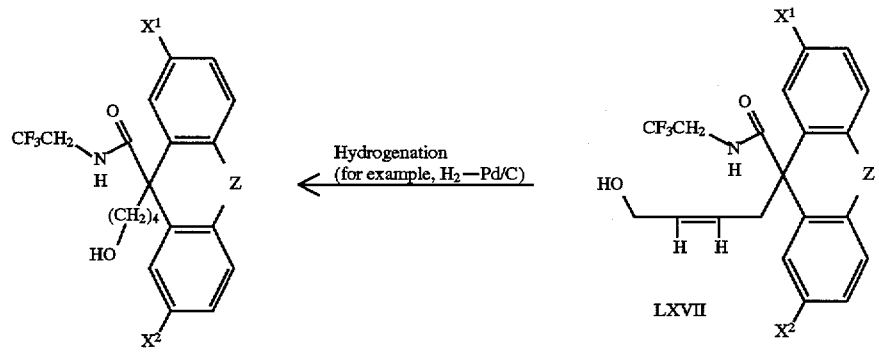

LXIX ← Hydrogenation (for example, $H_2$—Pd/C) — LXVII

↓ Halide Formation

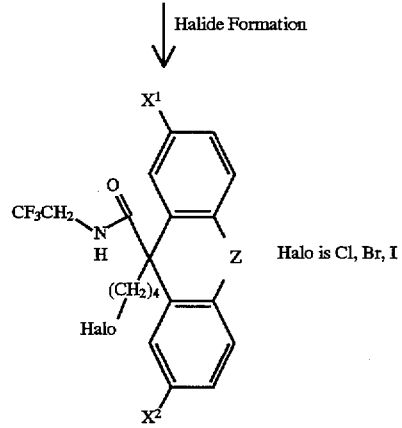

Halo is Cl, Br, I

XXXIIIJ

Scheme VIII
Preparation of N-Oxides of Formula I compounds

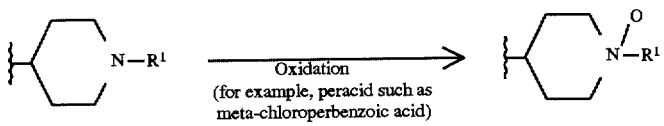

Amide formation Reaction Schemes I, II and IV, may be carried out by a number of methods known in the art. For example, an amine substrate may be treated with (1) an acid halide $R^5C(O)$halo in an aprotic solvent, optionally in the presence of a tertiary amine base (e.g., triethylamine); (2) the acid halide in the presence of an aqueous base under Schotten-Baumann conditions; (3) a free carboxylic acid ($R^5CO_2H$) in the presence of a coupling agent such as dicyclohexylcarbodiimide (DCC), diisopropyl carbodiimide (DIC) or 1-(3-dimethylamino-propyl)-3-ethylcarbodiimide hydrochloride (WSC), optionally in the presence of 1-hydroxybenzotriazole (HOBT); (4) the free acid in the presence of N, N-carbonyldiimidazole in an aprotic organic solvent followed by the amine substrate; (5) trialkylaluminum (e.g., $Al(CH_3)_3$) in an aprotic solvent, followed by an ester (e.g., $R^5CO_2$alkyl) or (6) mixed anhydride formation, by reacting the acid with an acid chloride (e.g., isobutyl chloroformate or bis-(2-oxo-3-oxazolidinyl)phosphinic chloride (Bop—Cl)) in the presence of a tertiary amine base (e.g., triethylamine) followed by treatment with the amine substrate.

Protection and deprotection (Reaction Schemes II, VI and VII) may be carried out by procedures generally known in the art. See, for example, T. W. Greene, *Protecting Groups in Organic Synthesis*, Second edition, 1991. PG in Scheme II denotes a nitrogen-protecting group. One particularly useful group is tert-butoxy-carbonyl (BOC) which can be derived from the associated anhydride. BOC-protected amines may typically be deprotected by treatment with acid (e.g., trifluoroacetic acid or hydrochloric acid) in procedures well understood by those having ordinary skill in the art.

Hydrogenolysis (Reaction Scheme II) may be carried out with $H_2$ using a balloon apparatus or a Parr Shaker in the presence of a catalyst (e.g., pallladium on activated carbon).

Amine alkylation and arylation (Reaction Schemes II, V and VI) may be carried out by methods known in the art. Suitable procedures are described in Cortizo, L., *J. Med. Chem.* 34, 2242–2247 (1991). For example, the alkylation or arylation may be carried out by treating the amine substrate with a halide (e.g., $R^1$-halo) or an oxytosylate (e.g., $R^1$—O—tosylate) in an aprotic solvent (e.g., dimethylformamide), optionally in the presence of a tertiary amine (e.g., triethylamine) or an inorganic base (e.g., potassium carbonate).

Amide N-alkylation (Reaction Scheme I) may be carried out by base treatment (e.g., NaH, KH, $KN[Si(CH_3)_3]_2$, $K_2CO_3$, P4-phosphazene base, or butyl lithium) in an aprotic organic solvent. Use of P4-phosphazene base is described in T. Pietzonka, D. Seebach, *Angew. Chem. Int. Ed. Engl.* 31, 1481, 1992.

The compounds of the invention may be employed in preventing, stabilizing or causing regression of atherosclerosis in a mammalian species by administering a therapeutically effective amount of a compound to decrease the activity of MTP.

The compounds of the invention can be tested for MTP inhibitory activity employing the procedures set out in U.S. application Ser. No. 117,362 filed Sep. 3, 1993, employing MTP isolated from one of the following sources:

(1) bovine liver microsomes, (2) $HepG_2$ cells (human hepatoma cells) or (3) recombinant human MTP expressed in baculovirus.

The compounds of the invention may also be employed in lowering serum lipid levels, such as cholesterol or triglyceride (TG) levels, in a mammalian species, by administering a therapeutically effective amount of a compound to decrease the activity of MTP.

The compounds of the invention may be employed in the treatment of various other conditions or diseases using agents which decrease activity of MTP. For example, compounds of the invention decrease the amount or activity of MTP and therefore decrease serum cholesterol and TG levels, and TG, fatty acid and cholesterol absorption and thus are useful in treating hypercholesterolemia, hypertriglyceridemia, hyperlipidemia, pancreatitis, hyperglycemia and obesity.

The compounds of the present invention are agents that decrease the activity of MTP and can be administered to various mammalian species, such as monkeys, dogs, cats, rats, humans, etc., in need of such treatment. These agents can be administered systemically, such as orally or parenterally.

The agents that decrease the activity or amount of MTP can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered in amounts of from about 5 to about 500 mg per day in single or divided doses of one to four times daily.

The following Examples represent preferred embodiments of the invention. All temperatures are in °C. unless indicated otherwise.

NOTE: The phrase "flash chromatography" as employed in the following examples refers to chromatography performed on EM Industries Silica Gel 60, 230–400 mesh under 10–20 psi of nitrogen pressure.

EXAMPLE 1

9-[4-[4-[([1,1-Biphenyl]-4-ylcarbonyl)amino]-1-piperidinyl]-3,3-difluorobutyl]-N-(2,2,2-trifluoroethyl)-9H-fluorene-9-carboxamide, monohydrochloride

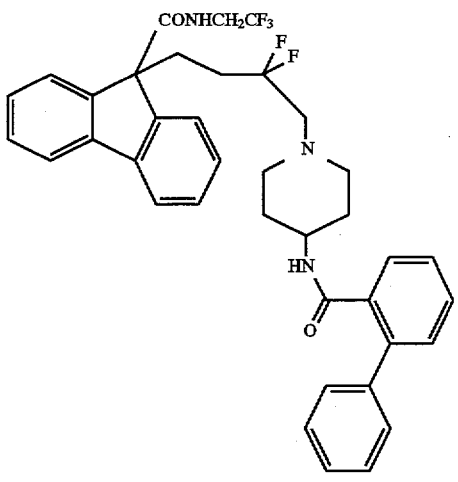

A mixture of

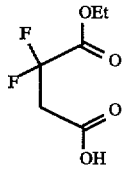

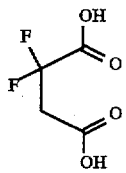

(5.18 g, 33.6 mmol), acetyl chloride (5.2 mL) and acetic anhydride (5.2 mL) was heated to 50° C. under argon for 1 h. The reaction was cooled and evaporated. The residue was dissolved in EtOH (20 ml) and stirred at room temperature (RT) under argon. After 16 h, the solution was evaporated, the residue redissolved in Et$_2$O and the solution dried (Na$_2$SO$_4$) to give title compound as a colorless oil, 5.91 g, 97% material balance. The compound was used without further purification.

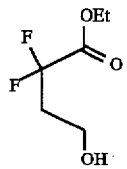

To a stirred solution of Part A compound (1.82 g, 10.0 mmol) in THF (10 mL) at room temperature under argon was added a solution of borane-methyl sulfide complex (1.25 mL, 13.2 mmol) in dichloromethane (14 mL). The reaction was set to reflux. After 24 h, the reaction was cooled, methanol (20 mL) was added and the reaction again set to reflux. After 1 h, the excess solvents were distilled at atmospheric pressure. The residue was bulb-to-bulb distilled at reduced pressure to provide title compound as a colorless oil, 1.45 g, 86%.

To a stirred solution of Part B compound (1.40 g, 8.33 mmol) in DMF (10 mL) at room temperature under argon was added Ph$_2$tBuSiCl (2.6 mL, 9.2 mmol) and imidazole (1.4 g, 21 mmol). After 2 h, the reaction was quenched with water and extracted three times with ether. The organic extracts were combined, dried (Na$_2$SO$_4$) and evaporated to give a brown oil. Purification by flash chromatography on silica gel (5×20 cm column, 2:7 dichloromethane/hexanes) gave title compound as a colorless oil, 1.83 g, 54%.

To a stirred solution of Part C compound (1.73 g, 4.26 mmol) in THF (5 mL) at room temperature under argon was added lithium borohydride solution (1.2 mL, 2.4 mmol, 2M in THF). After 16 h, the reaction mixture was quenched with saturated sodium bicarbonate solution and extracted three times with EtOAc. The organic extracts were dried (Na$_2$SO$_4$) and evaporated to give title compound as a colorless oil, 1.51 g, 97%. The compound was used in subsequent reactions without further purification.

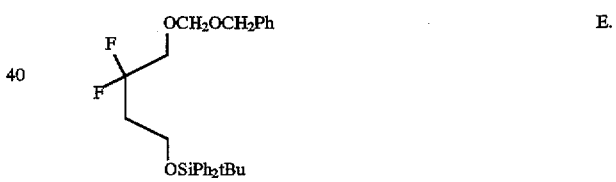

To a stirred solution of Part D compound (1.50 g, 4.12 mmol) in diisopropylethylamine (5 mL) at 10° C. under argon was added benzyloxymethyl chloride (BomCl) (0.7 mL, 4.9 mmol) in one portion. A precipitate began to form within 10 min. After 1 h, hexane was added to the reaction mixture and the resulting slurry washed with 10% hydrochloric acid (20 mL) and once with water. The organic layer was dried (MgSO$_4$) and evaporated to give a light yellow oil. Purification by flash chromatography on silica gel (5×20 cm column, 2:3 dichloromethane/hexane) gave title compound as a colorless oil, 1.77 g, 89%.

To a stirred solution of Part E compound (1.72 g, 3.55 mmol) in THF (5 mL) at room temperature under argon was added tetrabutylammonium fluoride solution (TBAF, 7.5 mL, 7.5 mmol, 1M in THF). After 1 h, the reaction was quenched with brine and extracted twice with EtOAc. The combined extracts were dried (Na₂SO₄) and evaporated. Purification by flash chromatography on silica gel (5×12 cm column, 1:9 EtOAc/dichloromethane) provided title compound as a colorless oil, 774 mg, 89%.

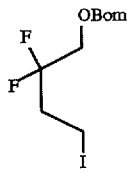
G.

To a stirred solution of Part F compound (770 mg, 3.13 mmol), triphenylphosphine (826 mg, 3.15 mmol) and imidazole (470 mg, 6.9 mmol) in THF (10 mL) at room temperature under argon was added a solution of iodine (800 mg, 3.15 mmol) in THF (5 mL) dropwise over 10 min. The reaction mixture was diluted with ether and washed once with saturated sodium bicarbonate (containing 5% NaHSO₃). The organic extract was dried (Na₂SO₄) and evaporated. Purification by flash chromatography on silica gel (5×10 cm column, dichloromethane) provided title compound as a colorless oil, 935 mg, 84%.

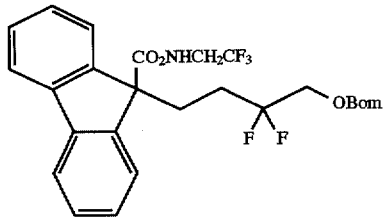
H.

To a solution of 9-fluorenecarboxylic acid (631 mg, 3.0 mmol) in THF (5 mL) under argon at −10° C. was added a solution of sodium bis(trimethylsilyl)amide (6.2 mL, 6.2 mmol, 1M in THF) over 10 min. The resulting slurry was stirred 60 min and then a solution of Part G compound (930 mg, 2.61 mmol) in THF (5 mL) was added. The reaction was allowed to warm to room temperature and stirred. After 48 h, the reaction was quenched with 10% citric acid solution and extracted twice with EtOAc. The organic extracts were combined, dried (MgSO₄) and evaporated. The oily residue was dissolved in dichloromethane (10 mL) and treated, at room temperature, with oxalyl chloride (0.52 mL, 6.0 mmol) and DMF (0.1 mL). After 1 h, the reaction was evaporated and then redissolved in dichloromethane (5 mL). This solution was added, dropwise over 10 min, to a stirred slurry of trifluoroethylamine hydrochloride (502 mg, 3.70 mmol) and Et₃N (1.12 mL, 8 mmol) in dichloromethane (10 mL) at 0° C. under argon. After 1 h, the reaction was quenched with 10% citric acid solution and extracted twice with EtOAc. The organic extracts were combined, dried (MgSO₄) and evaporated. Purification by flash chromatography (5×20 cm column, 1 L dichloromethane, then 5:95 ether/dichloromethane) to provide

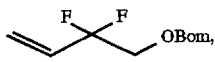

375 mg, 47% and then title compound, 120 mg, 9% as colorless oils.

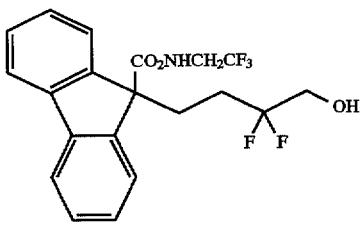
I.

A stirred slurry of Part H compound (108 mg, 0.208 mmol) and 20% Pd(OH)₂-on-carbon (200 mg) in cyclohexene (2 mL) and ethanol (5 mL) was refluxed for 2 h under argon. The reaction was cooled, evaporated, diluted with EtOAc, dried (MgSO₄) and filtered through a 0.75μ nylon filter. Evaporation provided title compound as a colorless oil, 53 mg, 64%.

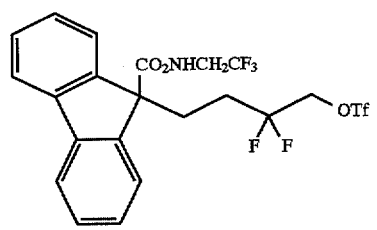
J.

To a solution of Part I compound (50.9 mg, 0.128 mmol) and pyridine (68 μL, 0.8 mmol) in dichloromethane (1 mL) at 0° C. under argon was added triflic anhydride (40 μL, 0.15 mmol) over 2 min. After 1 h, the reaction was quenched with 1M hydrochloric acid and extracted twice with EtOAc. The organic extracts were combined, dried (MgSO₄) and evaporated to give title compound as an orange crystalline solid, 68 mg, 100%.

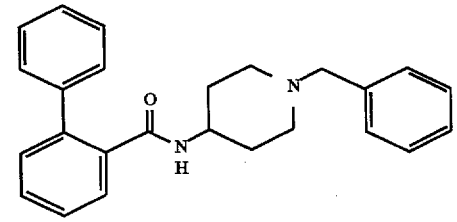
K.

K(1).

To a solution of 2-biphenyl carboxylic acid (31.2 g, 160 mmol) in methylene chloride (300 ml) was added the oxalyl chloride (21 ml, 280 mmol), followed by a few drops of DMF. The reaction bubbled vigorously and was stirred under argon at room temp 2 h. The solvent was evaporated in vacuo at less than 25° C., and the residue was dissolved in methylene chloride (250 ml). This solution was added dropwise to a solution of 4-aminobenzyl piperidine (Aldrich, 25.0 g, 130 mmol) and triethylamine (46 ml, 330 mmol) in methylene chloride (200 ml) at −5° C. The reaction stirred 30 minutes at that temperature after addition was complete. The reaction mixture was washed twice with water and once with brine. The organic layer was dried (Na₂SO₄), and the solvent was removed in vacuo to give title compound as a light yellow solid (56.6 g, 95.4% yield).

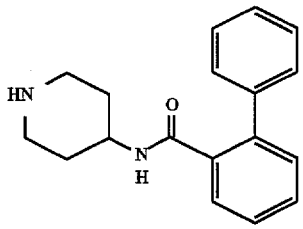

K(2).

To a solution of Part K(1) compound (55.5 g, 150 mmol) in ethanol (500 ml) was added cyclohexene (167 ml, 1.6 mol) and 20% palladium hydroxide on carbon (11.1 g). The reaction was heated to reflux and stirred at that temperature 2.75 h. The warm reaction was filtered through Celite® and rinsed with ethanol and methanol. The filtrate was concentrated in vacuo to give a light yellow oil. This oil was triturated twice with ether to give a light yellow solid (30.1 g).

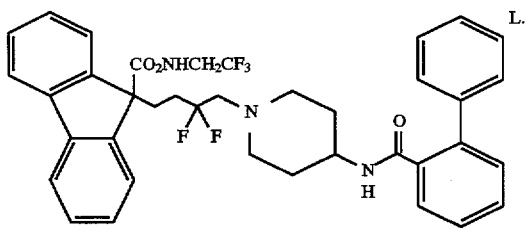

L.

To a stirred solution of Part J compound (68 mg. 0.126 mmol) in toluene (2 mL) at room temperature under argon was added Part K compound (84 mg, 0.3 mmol) in DMF (0.5 mL). The solution was heated to 50° C. After 14 h, the reaction was cooled, diluted with ether and washed once with saturated sodium bicarbonate solution. The organic layer was dried (Na$_2$SO$_4$) and evaporated. Purification by flash chromatography on silica gel (1×10 cm column, EtOAc) provided title compound as the free base as a white foam, 57 mg, 68%. The foam was diluted with dichloromethane and 0.1 mL of 4N hydrochloric acid. Evaporation provided the HCl salt of the title compound, 59 mg, mp 115°–118° C.

TLC: R$_f$=0.20 (free base, EtOAc, Silica gel 60) Mass Spectrometry: (electrospray, +ions) m/z 662 (M+H)

EXAMPLE 2

9-[4-[4-[[(4'-Chloro-[1,1'-biphenyl]-2-yl) carbonyl]-amino]-1-piperidinyl]butyl]-N-(2,2,2-trifluoroethyl)-9H-fluorene-9-carboxamide, monohydrochloride

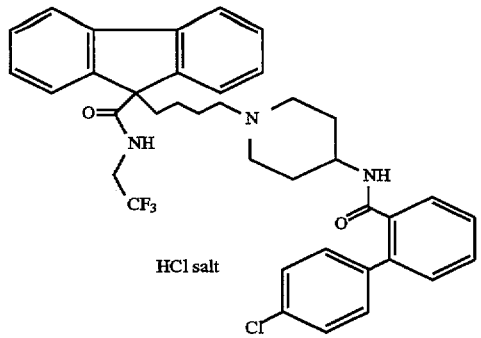

A.

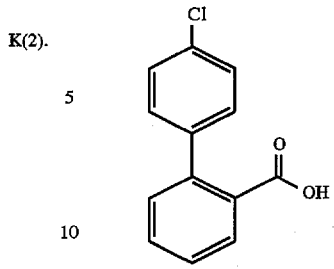

The title compound was prepared by the method of Meyers by Grignard addition of p-chlorophenylmagnesium bromide to o-methoxy-phenyl-1,1-dimethylisoxazole and hydrolysis with 6N HCl.

B. 9-[4-[4-[[(4'-Chloro-[1,1'-biphenyl]-2-yl)carbonyl]-amino]-1-piperidinyl]butyl]-N-(2,2,2-trifluoroethyl)-9H-fluorene-9-carboxamide, monohydrochloride To a solution of the Part A acid (2.0 g, 8.6 mmol) in methylene chloride (35 ml) was added a 2M solution of oxalyl chloride (6.0 ml, 12 mmol) in dichloromethane followed by a 2 drops of DMF. The reaction bubbled vigorously and stirred under argon at RT for 2 h. The solvent was evaporated in vacuo at less than 25° C., and the residue was dissolved in THF (50 ml). This solution was added dropwise to a solution of the Example 11 Part C diamine (4.45 g, 8.6 mmol) and triethylamine (3.54 g, 35 mmol) in THF (150 ml) at 0° C. The reaction stirred in a melting ice bath 1 h and warmed to RT and stirred for 48 h. The reaction mixture was diluted with ethyl acetate (200 mL) and washed once with water. The organic layer was dried (MgSO$_4$), and the solvent was removed in vacuo to give an off-white solid foam which was purified trituration with ethyl acetate to give a white solid.

The solid was diluted with ether (100 mL) and treated with 1M HCl in ether (10 mL, 10 mmol) in give a white powder which was filtered. The solid was collected and dried at 55° C. (20 mm Hg) overnight to give 3.95 g (67%) of title compound as a white powder.

mp:140°–150° C. MS (ES, +ions) m/z 660 (M+H); 1 Cl isotope pattern. Anal Calcd. for C$_{38}$H$_{37}$N$_3$O$_2$F$_3$Cl+HCl: C, 63.07; H, 5.71; N, 5.81 Found: C, 62.79; H, 5.62; N, 6.05.

EXAMPLE 3

9-[4-[4-[[[1-(Phenylmethyl)-2-piperidinyl]carbonyl] amino]-1-piperidinyl]butyl]-N-(2,2,2-trifluoroethyl)-9H-fluorene-9-carboxamide, dihydrochloride

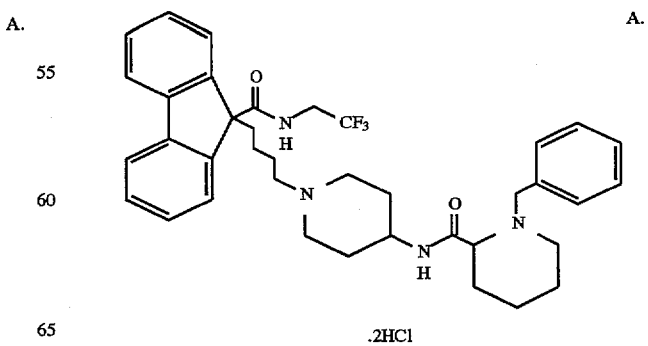

A.

-continued

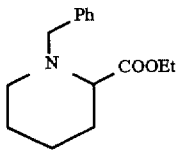

Benzyl bromide (700 μl, 5.7 mmol) was added dropwise to a slurry of ethyl pipecolinate hydrochloride (1.0 g, 5.2 mmol) and potassium carbonate (1.5 g, 11.4 mmol) in DMF (10 mL) under argon. The reaction was stirred at RT for 2.5 h., then the solvent was removed in vacuo. The residue was partitionated between dichloromethane (10 mL) and water (10 mL), and the aquous layer was extracted with dichloromethane (3×10 mL). The combined organic layers were dried over sodium sulfate, then concentrated in vacuo to give a cloudy oil, which was chromatographyed (10% ethyl acetate in hexane) on silica gel (60 g). Pure fractions were combined and evaporated to give title compound (1.24 g, 97%) as a colorless oil.

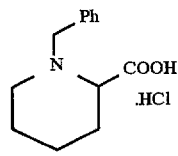

B.

A biphasic mixture of Part A compound (600 mg, 2.4 mmol) and 1N KOH (7.2 mL) in dioxane was stirred at RT overnight, then the reaction was heated at 50° C. for 2 days. The reaction was cooled to RT then adjusted to pH 2 with 1N HCl. The cloudy mixture was concentrated in vacuo then pumped under high vaccum overnight. The solid product was stirred with chloroform (10 mL) for 15 min. then filtered. The filtrate was concentrated in vacuo to give title compound (411 mg, 67%) as a yellow foam.

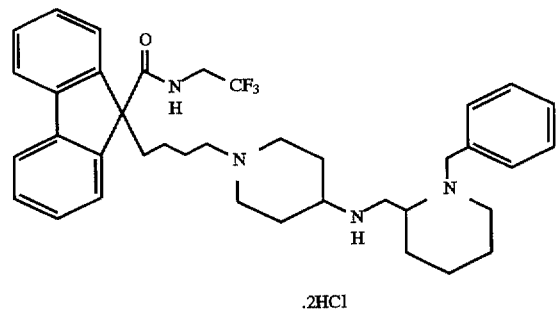

C.

Ethyl 3-(3-dimethylamino)propyl carbodiimide (164 mg, 0.86 mmol) was added to a mixture of Example 11 Part C compound (404 mg, 0.78 mmol), Part B compound (200 mg, 0.78 mmol), hydroxybenzotriazole (105 mg, 0.78 mmol), and 4-methyl morpholine (300 μl, 2.7 mmol) in dichloromethane (3 mL) under argon. The reaction was stirred at RT for 24 h., diluted with dichloromethane (20 mL) and washed with saturated sodium bicarbonate solution (5 mL). The organic layer was washed with water (2×5 mL) then dried over sodium sulfate. Evaporation gave a yellow gum. Purification was performed by flash chromatography (4% methanol in dichloromethane) on silica gel (50 g). Pure fractions were combined and evaporated to give a colorless oil. The resulting product was dissolved in methanol (1 mL) and a solution of hydrochloric acid in ethyl ether (1.1M, 1.1 mL) was added. The reaction was stirred at RT for 10 min, then evaporated to dryness. The product was dried in a vacuum oven (55° C., 24 h) to give title compound (302 mg, 54%) as a white solid.

m.p. 161°–165° C. MS (ESI, +ion): 647 (M+H) Anal. Calc. for $C_{38}H_{47}Cl_2F_3N_4O_2 \cdot 1.5 H_2O$: C, 61.12; H, 6.75; N, 7.50; Cl, 9.50; F, 7.63 Found: C, 60.97; H, 6.77; N, 7.40; Cl, 9.18; F, 7.34

EXAMPLE 4

N-(2,2,2-Trifluoroethyl)-9-[4-[4-[[[4-(trifluoromethyl)[1,1-biphenyl]-2-yl]carbonyl]amino]-1-piperidinyl]butyl]-9H-fluorene-9-carboxamide, monohydrochloride

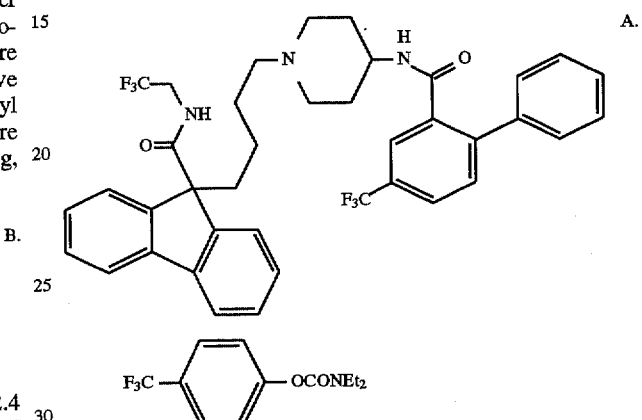

A.

To a stirred solution of

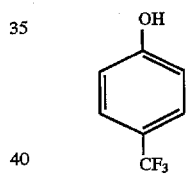

(3.08 g, 19.0 mmol) in THF (20 mL) at room temperature under argon was added triethylamine (2.80 mL, 20.0 mmol), diethyl carbamyl chloride (2.50 mL, 19.5 mmol) and dimethylaminopyridine (100 mg). The reaction was heated to 50° C. for 18 h. The reaction was cooled, diluted with ether, washed with 10% citric acid solution, brine and dried (MgSO$_4$). Purification by flash chromatography on silica gel (5×15 cm column, 55:45 hexane/dichloromethane) provided title compound as a colorless oil, 4.35 g, 89%.

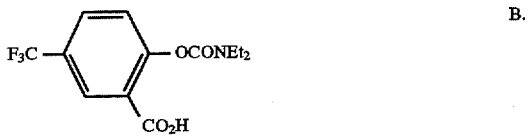

B.

To a flame-dried three-necked flask fitted with a dropping funnel and thermometer under an argon atmosphere was added THF (100 mL) and N,N,N,N-tetramethylethylene diamine (TMEDA, 4.4 mL, 29.2 mmol). The resulting solution was cooled to −73° C. and a solution of s-butyllithium in hexane (22.0 mL, 1.25M, 27.5 mmol) was added dropwise over 1 min. After 30 min, a solution of Part A compound (5.90 g, 22.6 mmol) in THF (20 mL) was added over 20 min. After an additional hour, dry carbon dioxide gas was bubbled through the solution for 30 min. The cold bath was removed and the reaction was allowed to warm to 0° C. The turbid solution was immediately quenched with 10% citric acid solution, extracted twice with EtOAC, dried (MgSO₄) and evaporated to give title compound as a white solid, mp 124°–126° C., 5.88 g, 85%.

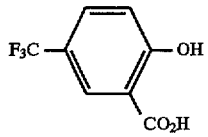

C.

A slurry of Part B compound (2.28 g, 7.47 mmol) in 6M hydrochloric acid (25 mL) under argon was heated to reflux for 1 h. The reaction was cooled, diluted with water, washed and filtered. The damp filter cake was dissolved in EtOAc, dried (MgSO₄) and evaporated to give title compound as a white solid, 1.52 g, 99%, mp 148°–149° C.

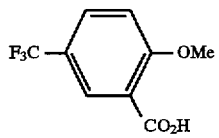

D.

To a stirred solution of Part C compound (1.50 g, 7.28 mmol) in DMF (20 mL) under argon at room temperature was added potassium carbonate (2.8 g, 20 mmol). The slurry was heated to 50° C. and then dimethyl sulfate (1.9 mL, 20 mmol) was added. After 1 h, the reaction mixture was quenched with 10% citric acid solution (20 mL) and extracted twice with ether. The combined extracts were washed with water, dried (MgSO₄) and evaporated to give the methyl ester of title compound as a colorless oil, 1.71 g, 100%.

The oil was dissolved in THF (10 mL), 3M sodium hydroxide solution (10 mL) was added and the mixture was heated to reflux under argon for 1 h. The solution was cooled, poured into cold 1M hydrochloric acid and extracted twice with dichloromethane. The extracts were combined, dried (MgSO₄) and evaporated to give title compound as a white solid, 1.45 g, 91%, mp 105°–107° C.

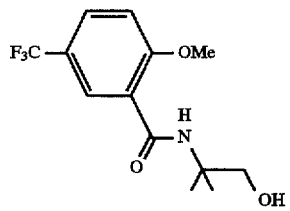

E.

To a stirred solution of Part D compound (1.40 g, 6.36 mmol) in dichloromethane (10 mL) protected by a Drierite-filled tube at room temperature was added oxalyl chloride (1.00 mL, 11.5 mmol) and DMF (50 µL). After 2 h, the solution was evaporated and redissolved in dichloromethane (20 mL). To this solution, under argon at room temperature, was added Et₃N (1.02 mL, 7.33 mmol) and then 2-amino-2-methyl-1-propanol (0.70 mL, 7.33 mmol). An exotherm results in an orange solution. After 13 h, the reaction mixture was diluted with dichloromethane, washed twice with 10% citric acid solution, dried (MgSO₄) and evaporated to give title compound as a white foam, 2.08 g, >100% material balance.

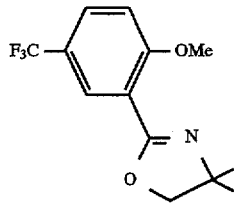

F.

To a solution of Part E compound (2.08 g) in dichloromethane (20 mL) at room temperature and protected by a Drierite-filled tube was added thionyl chloride (1.9 mL, 23.6 mmol). The solution was stirred for 2 h, then diluted with dichloromethane and poured into a 1:1 mixture of ice and saturated sodium bicarbonate solution. The aqueous layer was adjusted to pH 8 with 1M potassium hydroxide solution and extracted twice with dichloromethane. The organic extracts were combined, dried (Na₂SO₄) and evaporated. Purification by flash chromatography on silica gel (5×10 cm column, 1:9 EtOAc/dichloromethane) provided title compound as a white solid, 1.56 g, 90% yield starting from Part D compound, mp 55°–57° C.

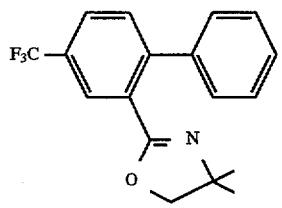

G.

To a stirred solution of Part F compound (1.17 g, 4.28 mmol) in THF (10 mL) at 0° C. under argon was added a solution of phenylmagnesium bromide (1.7 mL, 3M in ether, 5.1 mmol) over 5 min. After stirring an additional 10 min, the ice bath was removed and the reaction allowed to stir at room temperature. After 2 h, the reaction was quenched with saturated ammonium chloride solution and extracted twice with EtOAc. The extracts were combined, dried (Na₂SO₄) and evaporated to give a brown oil. Purification by flash chromatography on silica gel (5×15 cm column, 0.5 L hexane and then dichloromethane) provided title compound as a colorless oil, 1.36 g, 100%.

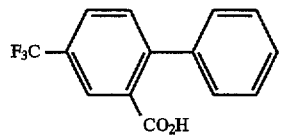

H.

A slurry of Part G compound (1.25 g, 3.91 mmol) in 6M hydrochloric acid (25 mL) was heated to reflux for 13 h. The reaction mixture was cooled and extracted twice with dichlormethane. The extracts were combined, dried (MgSO₄) and evaporated. Purification by flash chromatography on silica gel (5×15 cm column, EtOAc) provided title compound as a white solid, 395 mg, 38%, mp 120°–122° C.

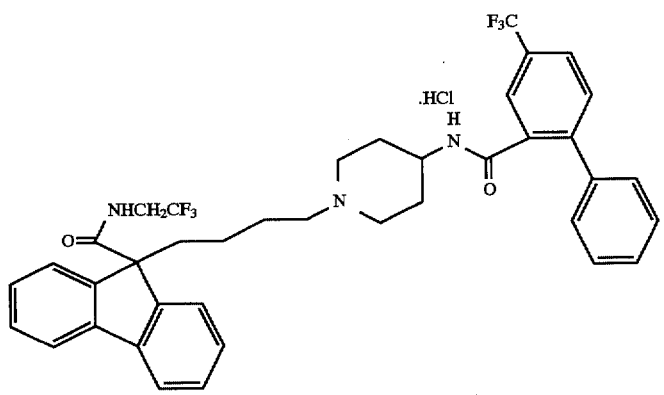

A solution of Part H compound (380 mg, 1.43 mmol) in thionyl chloride (3 mL) was stirred at room temperature, protected by a Drierite-filled tube. After 2 h, the reaction was evaporated and then reevaporated from dichloromethane. The semi-solid residue was dissolved in dichloromethane (5 mL) and added dropwise to a solution, at 0° C. under argon, of Example 11 Part C compound (816 mg, 1.57 mmol), Et₃N (0.7 mL, 5 mmol) and DMAP (50 mg, 0.4 mmol) in 10 mL of dichloromethane. After the addition was completed, the reaction was warmed to room temperature and stirred for 3 h. The reaction mixture was diluted with EtOAc, washed once with saturated sodium bicarbonate solution, dried (Na₂SO₄) and evaporated. Purification by flash chromatography on silica gel (5×15 cm column, 3:17 hexanes/EtOAc) provided title compound (as the free base) as a white foam, 640 mg, 65%. The foam was dissolved in dichloromethane (5 mL) and treated with 4M hydrogen chloride in dioxane (0.3 mL). Evaporation provided title compound as the hydrogen chloride salt, 670 mg, mp 129°–134° C.

Mass Spectrometry: (electrospray, +ions) m/z 694 (M+H).

EXAMPLE 5

9-[4-[4-[[2-Chloro-5-(trifluoromethyl)benzoyl] amino]-1-piperidinyl]butyl]-N-(2,2,2-trifluoroethyl)-9H-fluorene-9-carboxamide, N-oxide

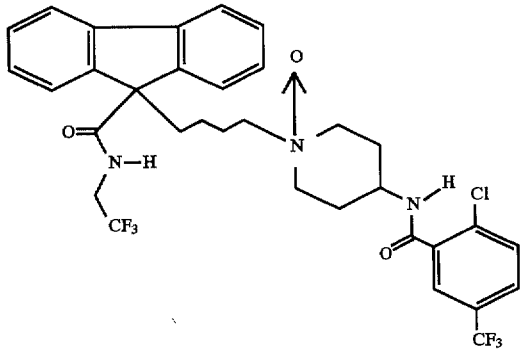

To a solution of the Example 111 amine free base (8.50 g, 13.0 mmol) in methylene chloride (35 ml) was added a 35% of peracetic acid solution in acetic acid (3.7 ml, 15 mmol). An additional 3.7 mL of peracetic acid solution was added (15 mmol) after 1 h. The reaction mixture was stirred for 16 h at RT, diluted with toluene (200 mL) and the contents stripped. The residue was pumped to constant weight. The colorless remainder was diluted with CHCl₃/methanol (100 mL, 9:1) and concentrated to give an off-white solid foam which was recrystalized from a (10:1; 10 mL) dichloromethane/methanol solution. The yield of material was 2.3 g. The mother liquor was purified by flash column chromatography on silica gel with 7:93 methanol/dichloromethane to give 4.2 g of pure material. The solids were combined to give 6.5 g (75%) of title compound as a white solid.

mp:131°–136° C.; material then resolidified: mp: 198°–200° C. decomp. MS (ES, +ions) m/z 668 (M+H). monochloro isotope pattern. Anal Calcd. for $C_{33}H_{32}N_3O_3F_6Cl+H_2O$: C, 57.77; H, 5.00; N, 5.78; Cl, 5.06 Found: C, 57.44; H, 5.11; N, 5.78; Cl, 5.06.

EXAMPLE 6A

N-(2,2,2-Trifluoroethyl)-9-[4-[4-[[[4'-(trifluoromethyl)[1,1-biphenyl]-2-yl]carbonyl] amino]-1-piperidinyl]butyl]-9H-fluorene-9-carboxamide, N-oxide,

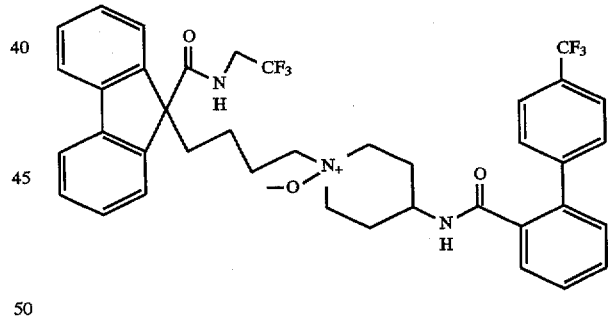

A CH₂Cl₂ (5 ml) solution of Example 10A compound (200 mg, 0.274 mmol) was added to a 0° C. solution of saturated NaHCO₃ (5 ml). After several minutes, a CH₂Cl₂ (2 ml) solution of meta-chloroperbenzoic acid (63 mg, 80%, 0.292 mmol) was added. A further amount of meta-chloroperbenzoic acid (23 mg, 80%, 0.107 mmol) was added in three portions over the next 1 h while the reaction was allowed to come to room temperature. The reaction mixture was partitioned between CH₂Cl₂ and saturated NaHCO₃ after 1.45 h. The aqueous layer was extracted twice with CH₂Cl₂, the organics dried over Na₂SO₄, and concentrated in vacuo to a colorless foam (200 mg). The residue was purified by flash column chromatography (silica gel, 50 ml), eluting with 5% MeOH:CH₂Cl₂, then 10% MeOH:CH₂Cl₂ with 1% NH₄OH, to give title compound (151 mg, 77.6% yield) as a colorless solid. mp 136°–142° C.

[shrinks 115° C.]. Rf=0.38 (10% MeOH:CH$_2$Cl$_2$). MS: (electrospray, +ions) m/z 710$^+$(M+H).

EXAMPLE 6B

N-(2,2,2-Trifluoroethyl)-9-[4-[4-[[[4'-(trifluoromethyl)[1,1-biphenyl]-2-yl]carbonyl]amino]-1-piperidinyl]butyl]-9H-fluorene-9-carboxamide, N-oxide.

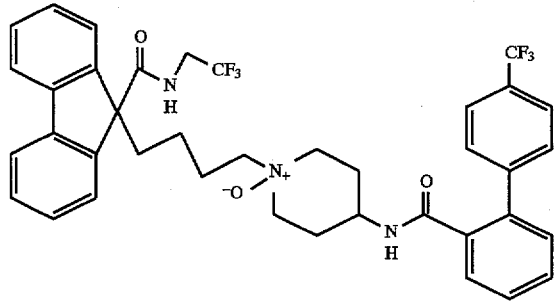

(Alternative Preparation)

To a CH$_2$Cl$_2$ (20 ml) solution of Example 10A compound (5.3 g, 7.64 mmol) in an adiabatic water bath was added peracetic acid (1.7 ml, 32% in AcOH, 8.08 mmol). A further amount of peracetic acid (0.9 ml, 32% in AcOH, 4.28 mmol, 12.3 mmol total) was added in three portions over the next 1.5 h. The reaction mixture was partitioned between CH$_2$Cl$_2$ and 1N KOH, the aqueous layer extracted twice with CH$_2$Cl$_2$, the combined organics washed with H$_2$O, dried over Na$_2$SO$_4$, and concentrated in vacuo to a foam (4.95 g). The residue was crystalized from hot EtOH and H$_2$O to give a colorless solid containing still impure solid. The crude material (5.5 g, combined with an identical reaction starting with 0.93 mmol Example 10A compound) could be purified by flash column chromatography (silica gel, 200 g), eluting with 10% MeOH:CH$_2$Cl$_2$ to give the title compound (3.5 g, 57% yield) as a colorless solid.

EXAMPLE 7

9-[4-[4-[[2-(2-Benzothiazolyl)benzoyl]amino]-1-piperidinyl]butyl]-N-(2,2,2-trifluoroethyl)-9H-fluorene-9-carboxamide, N-oxide

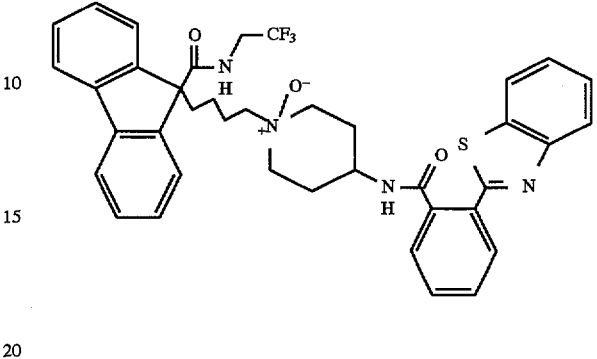

A solution Example 9 compound (free base, 14.589 g, 21.3 mmol) in CH$_2$Cl$_2$ (≈300 mL) at room temperature was treated with 4.40 mL 32% peracetic acid in dilute HOAc. After 2 hours, additional peracetic acid solution (1.2 mL) was added and stirring continued for 1 hour. The mixture was quenched with saturated NaHCO$_3$ and the CH$_2$Cl$_2$ layer was separated. The organic extract was washed with half-saturated NaCl, dried (Na$_2$SO$_4$), and filtered. The solution was diluted with EtOAc (≈200 mL) and let stand to give a white precipitate which was collected by filtration, washed with EtOAc and Et$_2$O, and dried in vacuo to give title compound (8.582 g, corrected for solvent): mp 189°–191° C.

MS: ESI (M+H)$^+$699; (M−H)$^-$697.

EXAMPLE 8

9-[4-[4-[(5-Chloro-2-methylbenzoyl)amino]-1-piperidinyl]butyl]-N-(2,2,2-trifluoroethyl)-9H-fluorene-9-carboxamide, N'-oxide.

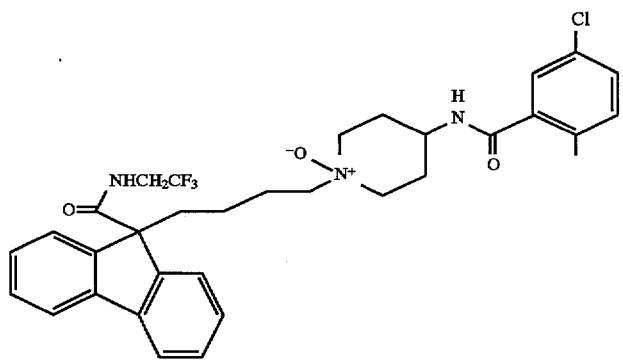

-continued

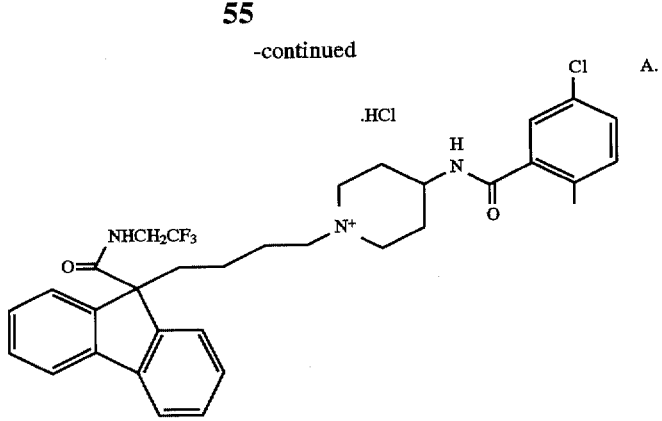
A.

To a stirred slurry of

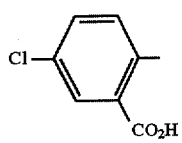

(2.05 g, 12.0 mmol), Example 11 Part C compound (6.22 g, 12.0 mmol), N-methylmorpholine (3.30 mL, 30.0 mmol) and HOBt.H$_2$O (1.80 g, 12.0 mmol) in dichlormethane (100 mL) at room temperature under argon was added EDAC (2.61 g, 13.7 mmol). Within 1 h, a clear yellow solution had formed. After 3 h, the reaction mixture was partitioned between EtOAc and saturated sodium bicarbonate solution. The organic extract was washed with brine, dried (Na$_2$SO$_4$) and evaporated. The resulting solid was recrystallized from EtOAc/hexanes to give the free base of the title compound, 6.56 g, 91%, mp 201°–202° C. The free base was dissolved in dichloromethane (25 mL) and treated with 4M hydrogen chloride in dioxane (3 mL). Evaporation provided title compound as the hydrogen chloride salt, an amorphous solid, 7.15 g, 100%

MICROAnal. Calcd for C$_{33}$H$_{35}$ClF$_3$N$_3$O$_2$+HCl+ 0.4H$_2$O+0.22 dioxane: C, 61.55; H, 5.88; N, 6.36; Cl, 10.72 Found: C, 61.56; H, 5.86; N, 6.28; Cl, 10.95 organic layer was dried (MgSO$_4$) and evaporated. Purification by flash chromatography on silica gel (5×15 cm column, 3:17 methanol/EtOAc) followed by redissolving the evaporated residue in dichloromethane and filtration through a 2 μM nylon filter provided title compound as a white solid, 450 mg, 73%, mp 124°–127° C.

MICROAnal. Calcd for C$_{33}$H$_{35}$ClF$_3$N$_3$O$_3$ 1.5 H$_2$O+0.6 EtOAc: C, 61.27; H, 6.22; N, 6.22; Cl, 5.11; F, 8.21 Found: C, 61.33; H, 6.38; N, 6.09; Cl, 5.19; F, 8.21 Mass Spectrometry: (electrospray, +ions) m/z 614 (M+H)

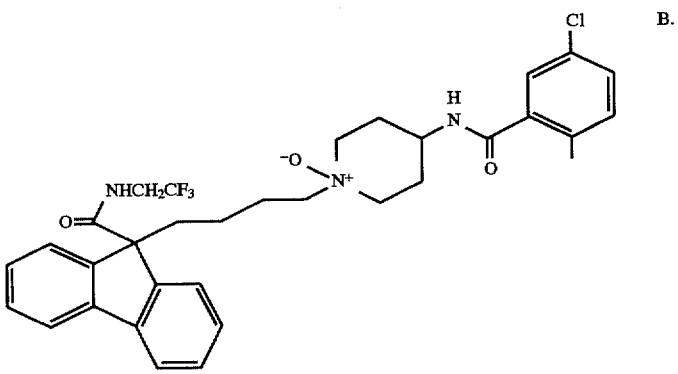
B.

To a rapidly stirring slurry of Part A compound (635 mg, 1.00 mmol) and sodium bicarbonate (100 mg, 1.2 mmol) in dichloromethane (20 mL) and saturated sodium bicarbonate solution (5 mL) at room temperature under argon, was added m-chloroperbenzoic acid (mCPBA, 220 mg, 80% purity, 1.05 mol) portionwise over the course of 20 min. After 1 h, the reaction was diluted with dichloromethane and washed twice with saturated sodium bicarbonate solution. The

EXAMPLE 9

9-[4-[4-[[2-(2-Benzothiazolyl)benzoyl]amino]-1-piperidinyl]butyl]-N-(2,2,2-trifluoroethyl)-9H-fluorene-9-carboxamide, monohydrochloride.

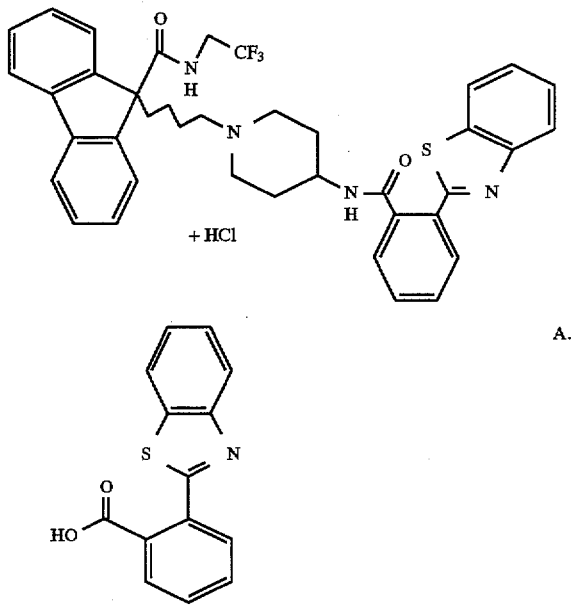

A slurry of phthalic anhydride (7.1 g, 47.9 mmol) and 2-aminothiophenol (7.0 mL, 8.2 g, 65.4 mmol) in glacial acetic acid (50 mL) was heated at reflux for 3 hours. The cooled reaction mixture was poured into ≈400 mL ice water to give a gummy precipitate. The mixture was extracted with EtOAc and the EtOAc extract was washed with 1N HCl and H$_2$O. The organic layer was extracted three times with saturated NaHCO$_3$ and the pooled bicarbonate extracts were acidified with 6N HCl to give a precipitate which was collected by filtration, washed with H$_2$O, and dried in vacuo to give title compound (11.27 g, 92%) as a white solid: mp 188°–189° C.

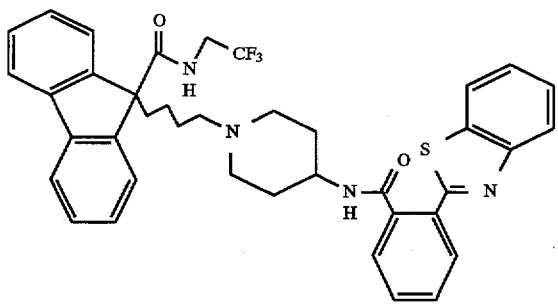

A slurry of Part A acid (2.048 g, 8.0 mmol) and Example 11 Part C diamine (3.960 g, 7.64 mmol) in CH$_2$Cl$_2$ (80 mL) was treated with N-methyl morpholine (2.1 mL, 1.93 g, 19.1 mmol) and DMF (6 mL). The slurry was then treated successively with HOBT hydrate (1.12 g, 8.3 mmol) and EDAC (1.630 g, 8.5 mmol). The mixture became homogeneous within 3 hours. After 4 hours, the solution was partitioned between EtOAc/Et$_2$O) and saturated NaHCO$_3$. The organic layer was separated, washed twice with H$_2$O and brine, then dried (Na$_2$SO$_4$), filtered, and stripped. Flash chromatography (Merck SiO$_2$, 8/92-MeOH/CH$_2$Cl$_2$) gave title compound (5.369 g, 103% of theory, 96% corrected for solvent) as a white foam.

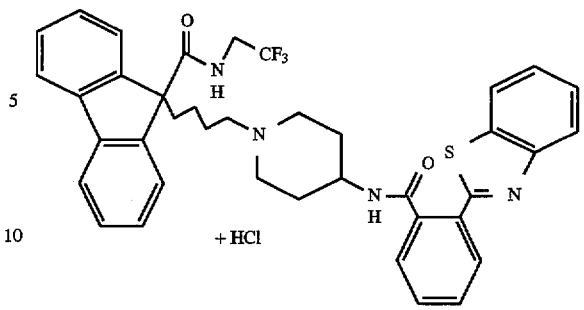

Part B compound (the free base, 5.254 g, 7.16 mmol corrected for solvent) was dissolved in ≈25 mL of 1,4-dioxane and treated with 2.2 mL of 4N HCl in 1,4-dioxane at room temperature. The resulting homogeneous mixture was added via canula to ≈350 mL of Et$_2$O with rapid swirling. The precipitate was collected by filtration, washed with Et$_2$O, and dried in vacuo at 45° C. to give title compound (5.113 g, 95% corrected for solvent) as a white solid.

MS (ESI): (M+H)$^+$683; (M−H)$^−$681.

EXAMPLE 10A

9-[4-[4-[[2-(2,2,2-Trifluoroethoxy)benzoyl]amino]-1-piperidinyl]butyl]-N-(2,2,2-trifluoroethyl)-9H-fluorene-9-carboxamide, monohydrochloride.

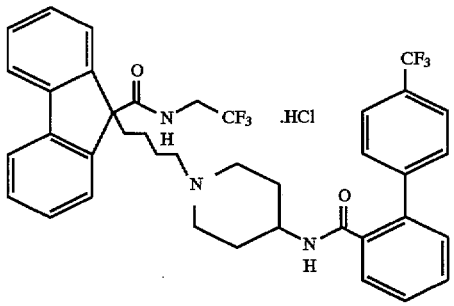

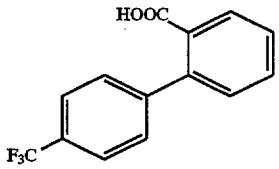

To a solution of the acid (3.2 g, 12 mmol) in methylene chloride (35 ml) was added oxalyl chloride (1.8 ml, 21 mmol) followed by a few drops of DMF. The reaction bubbled vigorously and stirred under argon at room temp 2 h. The solvent was evaporated in vacuo at less than 25° C., and the residue was dissolved in methylene chloride (50 ml). This solution was added dropwise to a solution of the Example 11 Part C diamine (5.0 g, 9.6 mmol) and triethylamine (6.7 ml, 48 mmol) in methylene chloride (50 ml) at −5° C. The reaction stirred in a melting ice bath 1 h. The reaction mixture was diluted with MeCl$_2$ and washed once with water. The organic layer was dried (Na$_2$SO$_4$), and the solvent was removed in vacuo to give an off-white solid foam which was purified by flash column chromatography (SiO$_2$, 800 g) eluted with 5% MeOH:0.5%NH$_4$OH: MeCl$_2$ to give a clear oil (5.23 g, 91.5% pure). This oil was purified again by flash column chromatography (SiO$_2$, 500 g) eluted with 3%MeOH: MeCl₂ to give a clear oil (4.11 g, 61.4% yield). This oil (4.07 g) was dissolved in MeOH (25 ml) and 1.1N ethereal HCl (8.0 ml) was added. The solvent was removed in vacuo to give title compound as a white solid foam (4.17 g).

mp 129°–142° C. MS (ESI, +ions) m/z 694 (M+H) Anal. calc'd for $C_{39}H_{37}F_6N_3O_2 \cdot HCl+1H_2O$: C, 62.61; H, 5.39; N, 5.62 Found: C, 62.48; H, 5.19; N, 5.60

EXAMPLE 10B

9-[4-[4-[[2-(2,2,2-Trifluoroethoxy)benzoyl]amino]-1-piperidinyl]butyl]-N-(2,2,2-trifluoroethyl)-9H-fluorene-9-carboxamide, monohydrochloride.

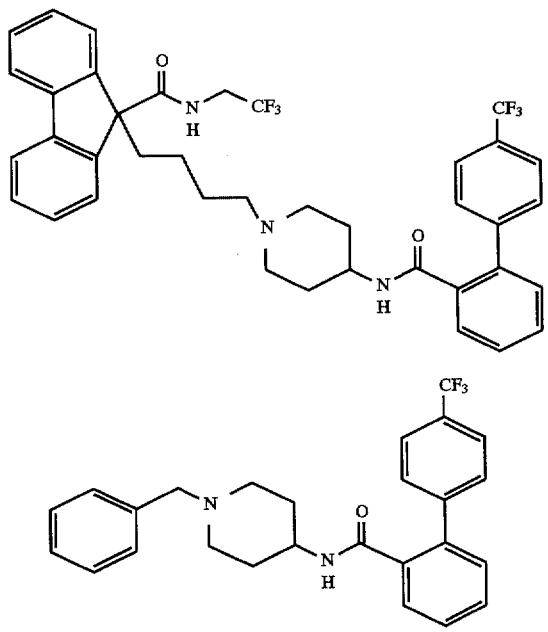

A.

To a slurry of 4'-(trifluoromethyl)-2-biphenyl carboxylic acid (50.0 g, 190 mmol) in methylene chloride (500 ml) was added the oxalyl chloride (28.7 ml, 330 mmol) followed by DMF (5 drops). The reaction bubbled vigorously and stirred at room temperature under argon 2 h. All solid had dissolved and evolution of gas had ceased. The solvent was removed in vacuo, and the residue was dissolved in methylene chloride (400 ml). This solution was added dropwise to a solution of compound

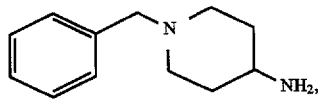

4-amino-1-benzylpiperidine (36.4 ml, 180 mmol) and triethylamine (65.4 ml, 470 mmol) in methylene chloride (300 ml) cooled in an ice/brine bath. After the addition was complete, a lot of solid had precipitated from solution. An additional 200 ml methylene chloride was added. The reaction stirred at room temperature under argon 18 h. The reaction was diluted with methylene chloride (600 ml) and washed twice with saturated NaHCO₃, once with brine and once with 1N KOH. The organic layer was dried with Na₂SO₄, and the solvent removed in vacuo to give a white solid. This solid was recrystallized from hot EtOH (1 L) and washed with heptane to give title compound as a white solid (59.1 g, 75.6% yield). The mother liquor was concentrated to dryness and recrystallized from hot EtOH (300 ml) and washed with heptane to give a second crop of title compound as a white solid (12.7 g, 16.2% yield).

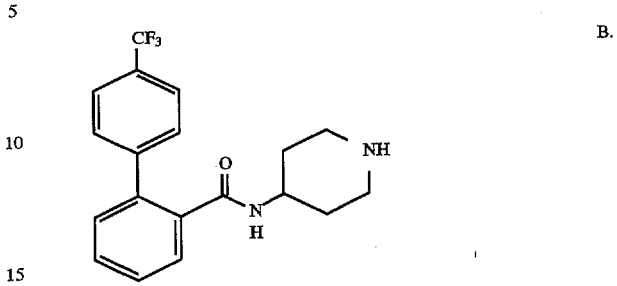

B.

To a solution of Part A compound (59.0 g, 130 mmol) in methanol (300 ml) and ethanol (300 ml) was added the cyclohexene (150 ml, 1.5 mol) and 20% palladium hydroxide on carbon (11.8 g). The reaction was heated in an argon atmosphere to reflux (80° C.) and stirred at that temperature 2.5 h. The hot mixture was filtered through Celite, washed with methanol and the solvent removed in vacuo to give title compound as a white solid (46.7 g, 99.6% yield).

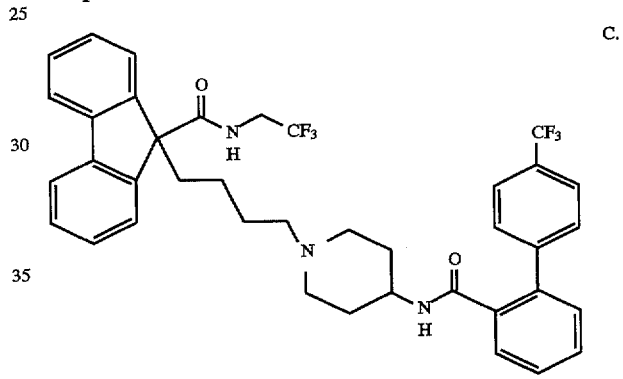

C.

To a stirred solution of Part B compound (18.0 g, 49 mmol) in DMF (100 ml) at room temperature under argon was added potassium carbonate (12.6 g, 49 mmol) followed by

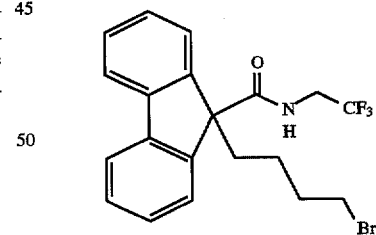

compound (prepared) as described in Example 11 Part C(2)) (21.0 g, 49 mmol). The reaction was heated to 50° C. and stirred at that temp under argon 24 h. After cooling, the reaction was filtered to remove potassium carbonate, and the filter cake was rinsed with ethyl acetate. The filtrate was partitioned between 20% heptane in ethyl acetate and water. The organic layer was washed five times with water and once with brine. The organic layer was dried (Na₂SO₄) and the solvent removed in vacuo to give a beige solid (30 g). This solid was recrystallized from 300 ml 25% EtOAc in heptane to give title compound as an off-white solid (27.0 g, 78.9% yield). mp 164°–68° C.

EXAMPLE 11

9-[4-[4-[(2-Pyridinylbenzoyl)amino]-1-piperidinyl]-butyl]-N-(2,2,2-trifluoroethyl)-9H-fluorene-9-carboxamide, dihydrochloride

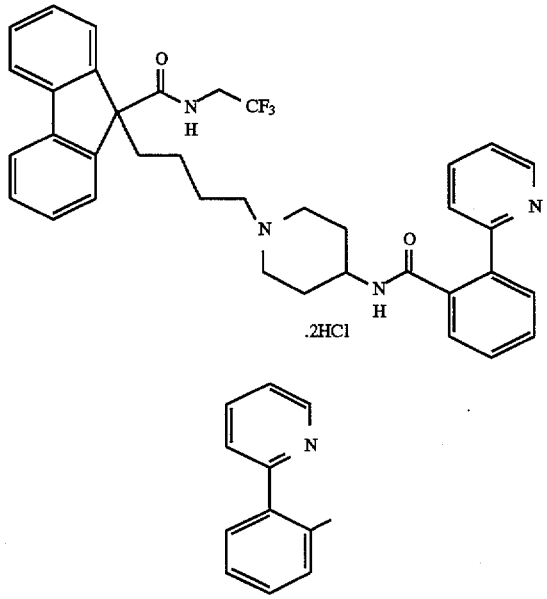

A.

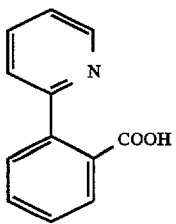

To a degassed solution of 2-bromopyridine (1.9 ml, 20 mmol) in ethylene glycol dimethyl ether (60 ml) under argon, tetrakis(triphenylphosphane) palladium° (700 mg, 0.6 mmol) was added. After stirring for 10 min., 2-methylphenyl boronic acid (2.9 g, 22 mmol) was added followed by sodium bicarbonate (5.04 g, 60 mmol in 60 ml water). The mixture was heated to reflux (~85° C.) and stirred at that temp overnight. After cooling to room temp., the solvent was removed in vacuo, the residue was partitioned between water and ether, and the aqueous layer was extracted twice with ether. The combined organic layers were dried (Na$_2$SO$_4$), and the solvent was removed in vacuo to give a black oil. This oil was distilled under high vacuum at ~95° C. to give title compound (2.75 g, 81.6% yield) as a clear oil.

B.

A solution of Part A compound (850 mg, 5.0 mmol) and potassium permanganate (1.9 g, 12.0 mmol) in water (25 ml) was heated to reflux (~100° C.) and stirred at that temperature 1 h. The hot reaction mixture was filtered, and the filtrate was evaporated to dryness. The solid residue was dissolved in water (5 ml) and acidified with acetic acid to pH 4–5. The resulting precipitate was isolated by filtration and rinsed with water to give a white solid (800 mg) which was recrystallized from hot ethanol (12 ml) to give title compound as a white solid (453 mg, 45.3% yield).

C.

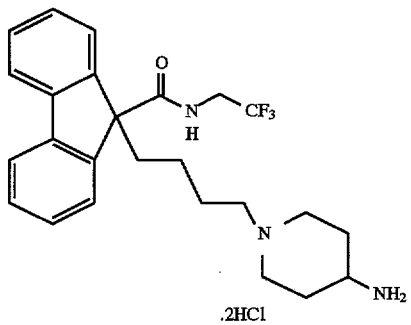

C(1).

To a solution of 9-fluorenecarboxylic acid (50 g, 240 mmol) in THF (1200 mL) at 0° C. was added dropwise a solution of n-butyllithium (2.5M, 211 mL, 530 mmol) in THF. The yellow reaction was stirred at 0° C. for 1 h, then 1,4-dibromobutane (31.3 mL, 260 mmol) was added dropwise over 30 min. The reaction was stirred at 0° C. for 30 min, then the reaction was warmed to RT for 30 h. The reaction was extracted with water (3×750 mL). The combined aqueous layers were extracted with ethyl ether (800 mL). The aqueous layer was made acidic with HCl solution (1N, 500 mL), then extracted with dichloromethane (3×750 mL). The combined organic layers were dried over MgSO$_4$. Evaporation gave title compound (71 g, 85%) as a white solid.

C(2).

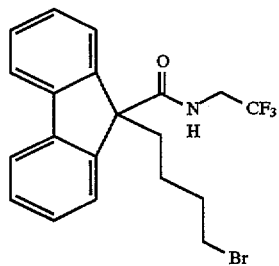

To a solution of Part C(1) acid (60 g, 173 mmol) and DMF (100 µL) in CH$_2$Cl$_2$ (600 mL) under argon at 0° C. was added oxalyl chloride (104 mL, 2.0M in CH$_2$Cl$_2$, 208 mmol) dropwise. The reaction was stirred at 0° C. for 10 min, then warmed to RT and stirred for 1.5 h. The reaction was concentrated in vacuo to give the crude acid chloride as a yellow oil. To a suspension of 2,2,2-trifluoroethylamine hydrochloride (25.9 g, 191 mmol) in CH$_2$Cl$_2$ (500 mL) at 0° C. under argon was added triethylamine (73 mL, 521 mmol) followed by dropwise addition of a solution of the crude acid chloride in CH$_2$Cl$_2$ (15 mL). The reaction was stirred at 0° C. for 1 h, diluted with CH$_2$Cl$_2$ (500 mL), and washed with water (2×300 mL), 1N HCl (2×300 mL), saturated NaHCO$_3$ (2×300 mL), and brine (2×300 mL), then dried over MgSO$_4$. Evaporation gave 80 g of a oil which was purified by flash chromatography on silica gel (2.5 kg). The crude product was loaded in a mixture of CH$_2$Cl$_2$ and hexane, and eluted with a step gradient of 10% EtOAc/hexane (4 L) to 15% EtOAc/hexane (2 L) to 20% EtOAc/hexane (4 L). Pure fractions were combined and evaporated to give title compound (52.5 g, 71%) as a white solid (mp 88°–92° C.).

C(3).

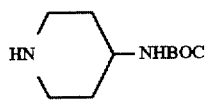

To a solution of 4-aminobenzylpiperidine (20 g, 105 mmol) in dichloromethane (200 mL) at 0° C. was added dropwise (about 30 min) a solution of di-tert-butyldicarbonate (25.2 g, 115 mmol) in dichloromethane (50 mL). The reaction was stirred at RT for 2 h, then evaporated to give an off-white solid. The product was triturated with ethyl ether (2×20 mL) to give a white solid (26.5 g, 90%). The product was dissolved in ethanol (200 mL). To the resulting solution at RT was added glacial acetic acid (10 mL, 177 mmol) and 10% palladium on activated carbon (2.6 g). Hydrogenation on a Parr apparatus (initial pressure 40 psi) was maintained for 19 h. The reaction was filtered through Celite and the filtrate was concentrated to dryness. The residue was dissolved in chloroform (500 mL) and washed with 1N KOH saturated with sodium chloride (3×100 mL). The aqueous layers were combined and extracted with chloroform (3×80 mL). Combined organics were dried over sodium sulfate and evaporated to give title compound (16 g, 90%) as a white solid (m.p. 157°–159° C.).

C(4).

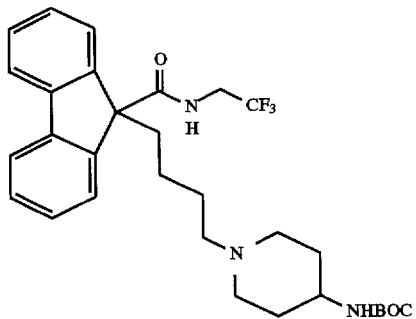

A mixture of Part C(2) compound (29.5 g, 69.2 mmol), Part C(3) compound (14.5 g, 72.7 mmol), and anhydrous potassium carbonate (11.5 g, 83.0 mmol) in DMF (100 mL) was stirred at 50° C. for 48 h, concentrated to dryness, and taken up in $CH_2Cl_2$ (500 mL). The solution was washed with saturated $NaHCO_3$ (3×80 mL) and brine (2×80 mL), then dried over $MgSO_4$. Evaporation gave a yellow oil which was purified by flash chromatography on silica gel (600 g), loaded in $CH_2Cl_2$, and eluted with a step gradient of 2% $MeOH/CH_2Cl_2$ (3 L) to 3% $MeOH/CH_2Cl_2$ (4 L). Pure fractions were combined and evaporated to give title compound (30 g, 86%) as a white foamy gum.

C(5).

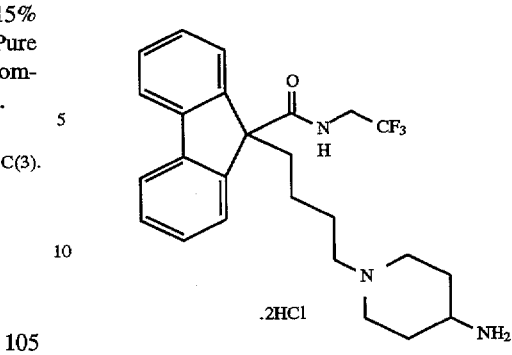

To a solution of Part C(4) compound (30.5 g, 60.4 mmol) in dioxane (120 mL) was added 4N HCl in dioxane (121 mL, 483 mmol). The reaction was stirred at RT for 4 h, then concentrated in vacuo to provide title compound (30 g) as a white foamy solid, containing a residual amount of dioxane.

D. 9-[4-[4-[(2-Pyridinylbenzoyl)amino]-1-piperidinyl]-butyl]-N-(2,2,2-trifluoroethyl)-9H-fluorene-9-carboxamide, dihydrochloride To a solution of the Part B acid (145 mg, 0.7 mmol) in methylene chloride (2 ml) was added oxalyl chloride (110 µl, 1.3 mmol) followed by a few drops of DMF. The reaction bubbled vigorously, turned yellow, and stirred under argon at room temp 2 h. The solvent was evaporated in vacuo at less than 25° C., and the residue was dissolved in methylene chloride (5 ml). This solution was added dropwise to a solution of the Part C diamine (300 mg, 0.6 mmol) and triethylamine (400 µl, 2.9 mmol) in methylene chloride (5 ml) at −5° C. The reaction stirred in a melting ice bath overnight. The reaction mixture was diluted with $MeCl_2$ and washed once with water. The organic layer was extracted twice with 1N HCl. The combined acid extractions were made basic with 1N NaOH and extracted twice with EtOAc. The combined EtOAc layers were dried ($Na_2SO_4$), and the solvent was removed in vacuo to give a brown oil which was purified by flash column chromatography ($SiO_2$, 90 g) eluted with 5% MeOH: 0.5% $NH_4OH:MeCl_2$ to give a clear oil (170 mg, 46.8% yield). 160 mg of this oil was dissolved in MeOH (2 ml) and 1.1N ethereal HCl (800 µl) was added. The solvent was removed in vacuo to give title compound as a light yellow solid (173 mg).

mp 146°–50° C. (dec.) MS (ESI, +ions) m/z 627 (M+H) Anal. calc'd for $C_{37}H_{37}F_3N_4O_2 \cdot 2HCl + 2H_2O$: C, 60.41; H, 5.89; N, 7.62 Found: C, 60.38; H, 5.86; N, 7.50

The following additional compounds were prepared employing procedures as set out hereinbefore.

EXAMPLE 11a

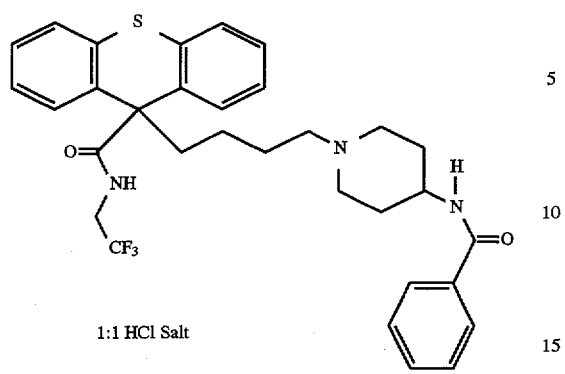

1:1 HCl Salt

9-[4-[4-(Benzoylamino)-1-piperidinyl]butyl]-N-(2,2,2-trifluoroethyl)-9H-thioxanthene-9-carboxamide, monohydrochloride.

M.P. 145°–150° C. MS (ES, +ions) m/z 582 (M+H) Elemental Anal. Calc'd for $C_{32}H_{34}N_3O_2F_3S+1.0$ HCl+0.75 $H_2O$: C, 60.94; H, 5.67; N, 6.66; F, 9.04 Found: C, 60.97; H, 6.00; N, 6.26; F, 9.15.

EXAMPLE 12

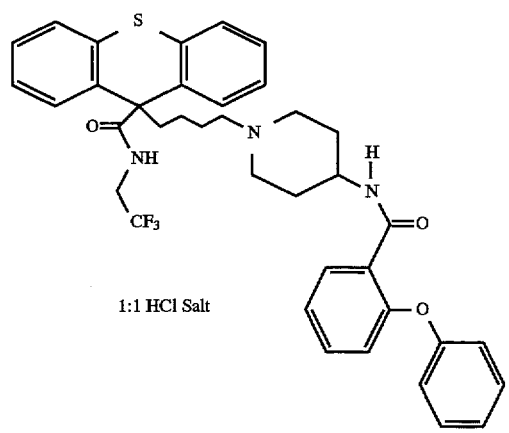

1:1 HCl Salt

9-[4-[4-[(2-Phenoxybenzoyl)amino]-1-piperidinyl]butyl]-N-(2,2,2-trifluoroethyl)-9H-thioxanthene-9-carboxamide, monohydrochloride.

M.P. 204°–208° C. MS (ES, +ions) m/z 578 (M+H) Elemental Anal. Calc'd for $C_{38}H_{38}O_3SF_3N_3+1$ HCl+0.5 $H_2O$: C, 63.46; H, 5.61; N, 5.84; S, 4.46 Found: C, 63.45; H, 5.51; N, 5.72; S, 4.15.

EXAMPLE 13

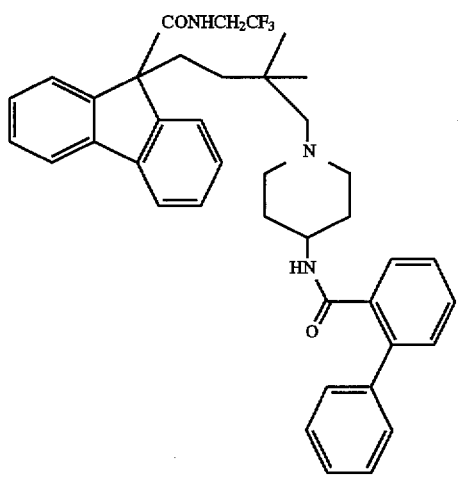

9-[4-[4-[([1,1-Biphenyl]-4-ylcarbonyl)amino]-1-piperidinyl]-3,3-dimethylbutyl]-N-(2,2,2-trifluoroethyl)-9H-fluorene-9-carboxamide, monohydrochloride.

M.P. 95°–101° C. MS (electrospray, –ions) m/z 654 (M+H)

EXAMPLE 14

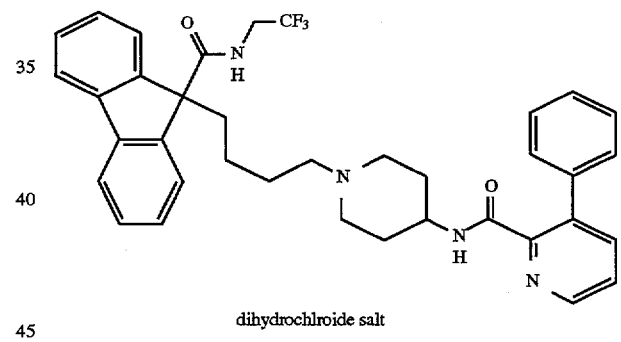

dihydrochlroide salt

9-[4-[4-[[(3-Phenyl-2-pyridinyl)carbonyl]amino]-1-piperidinyl]butyl]-N-(2,2,2-trifluoroethyl)-9H-fluorene-9-carboxamide, dihydrochloride salt.

MS (ESI, +ions) m/z 627 (M+H)$^+$; (ESI, –ions) m/z 625 (M–H)$^-$

EXAMPLE 15

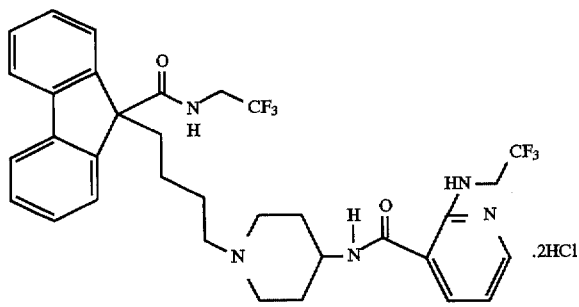

N-[1-[4-[9-[[(2,2,2-Trifluoroethyl)amino]carbonyl]-
9H-fluorene-9-yl]but-1-yl]piperidin-1-yl]-2-[N-(2,2,
2-trifluoroethyl)amino]pyridine-3-carboxamide,
hydrochloride.

MS (ESI, +ions) m/z 648 (M+H); (ESI, −ions) m/z 646 (M−H)

EXAMPLE 16

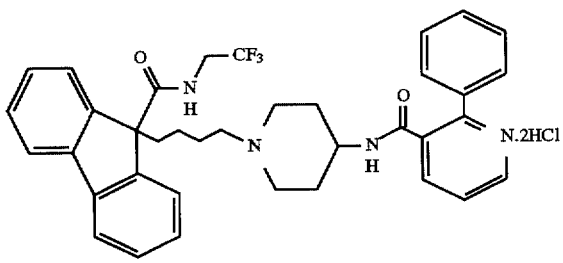

contains 0.1 mole of ethyl ether

N-[1-[4-[9-[[(2,2,2-Trifluoromethyl)amino]carbonyl]-
9H-fluoren-9-yl]but-1-yl]piperidin-4-yl]-2-
phenylpyridine-3-carboxamide, hydrochloride.

MS (ESI−NH$_3$, +ions) 627 (M+H)

EXAMPLE 17

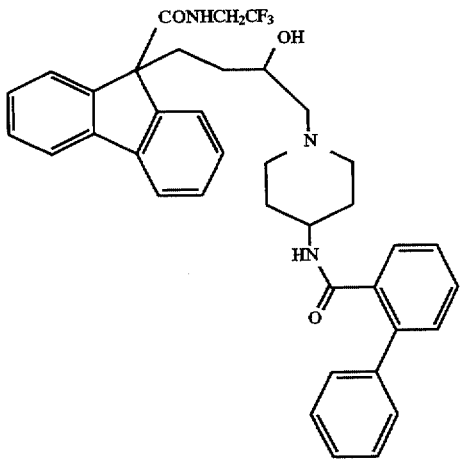

9-[4-[4-[((1,1-Biphenyl]-4-ylcarbonyl)amino]-1-
piperidinyl]-3-hydroxybutyl]-N-(2,2,2-trifluoroethyl)-
9H-fluorene-9-carboxamide, monohydrochloride.

M.P. 163°–165° C. MS (electrospray, +ions) m/z 642 (M+H)

EXAMPLE 18

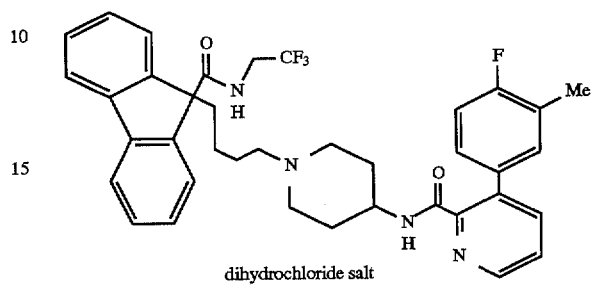

dihydrochloride salt

9-[4-[4-[[[3-(4-Fluoro-3-methylphenyl)-2-pyridinyl]-
carbonyl]amino]-1-piperidinyl]butyl]-N-(2,2,2-
trifluoroethyl)-9H-fluorene-9-carboxamide,
dihydrochloride.

MS (ESI, +ions) m/z 659 (M+H)$^+$; (ESI, −ions) m/z 657 (M−H)$^-$ Elemental Anal. Calc'd for C$_{38}$H$_{38}$F$_4$N$_4$O$_2$+2 HCl+ 1.5 H$_2$O+0.2 Et$_2$O+0.2 dioxane C, 60.12; H, 5.94; N, 7.08; F, 9.61; Cl, 8.96 Found: C, 60.17; H, 5.89; N, 7.24; F, 10.48; Cl, 8.91

EXAMPLE 19

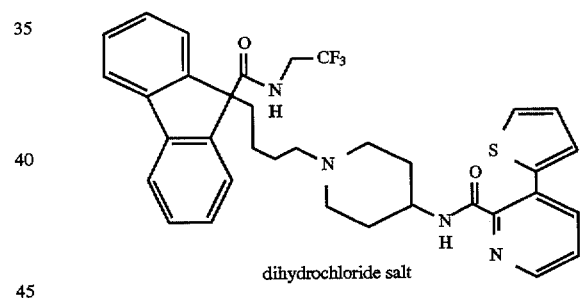

dihydrochloride salt

9-[4-[4-[[[3-(2-Thienyl)-2-pyridinyl]carbonyl]
amino]-1-piperidinyl]butyl]-N-(2,2,2-trifluoroethyl)-
9H-fluorene-9-carboxamide, dihydrochloride.

MS (ESI, +ions) m/z 633 (M+H)$^+$; (ESI, −ions) m/z 631 (M−H)$^-$

EXAMPLE 20

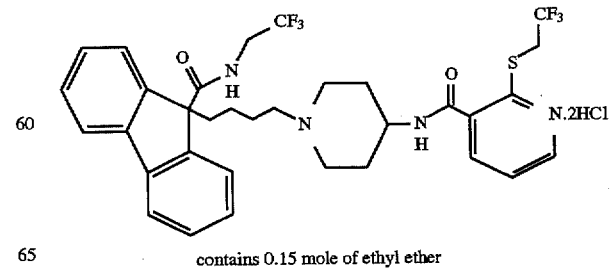

contains 0.15 mole of ethyl ether

N-(2,2,2-Trifluoromethyl)-9-[4-[4-[[[2-[(2,2,2-trifluoromethyl)thio]-3-pyridinyl]carbonyl]amino]-1-piperidinyl]butyl]-9H-fluorene-9-carboxamide, dihydrochloride.

MS (ESI—NH₃, +ions) 665 (M+H); 663 [M−H]

EXAMPLE 21

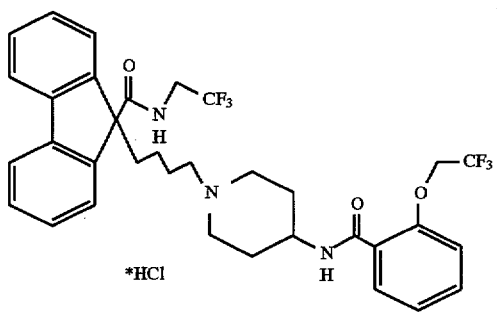

9-[4-[4-[[2-(2,2,2-Trifluoromethoxy)benzoyl]amino]-1-piperidinyl]butyl]-N-(2,2,2-trifluoromethyl)-9H-fluorene-9-carboxamide, monohydrochloride.

MS (electrospray, +ions) m/z 648 (M+H)

EXAMPLE 22

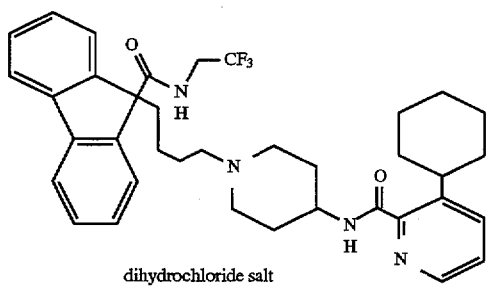

9-[4-[4-[[(3-Cyclohexyl-2-pyridinyl)carbonyl]amino]-1-piperidinyl]butyl]-N-(2,2,2-trifluoroethyl)-9H-fluorene-9-carboxamide, dihydrochloride.

MS (ESI, +ions) m/z 633 (M+H)⁺; (ESI, −ions) m/z 631 (M−H)⁻ Elemental Anal. Calc'd for $C_{37}H_{42}F_3N_4O_2$+2 HCl+ 1.5 H₂O+0.25 Et₂O: C, 60.69; H, 6.60; N, 7.45; F, 7.58; Cl, 9.43 Found: C, 60.89; H, 6.98; N, 7.51; F, 7.25; Cl, 9.83

EXAMPLE 23

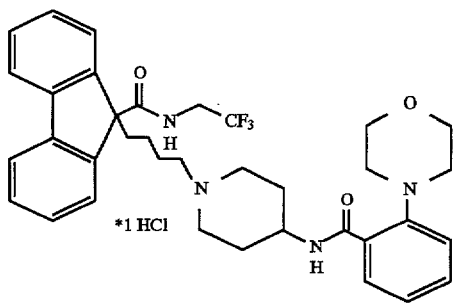

9-[4-[4-[[2-(4-Morpholinyl)benzoyl]amino]-1-piperidinyl]butyl]-N-(2,2,2-trifluoroethyl)-9H-fluorene-9-carboxamide, monohydrochloride.

MS (electrospray, +ions) m/z 635 (M+H)

EXAMPLE 24

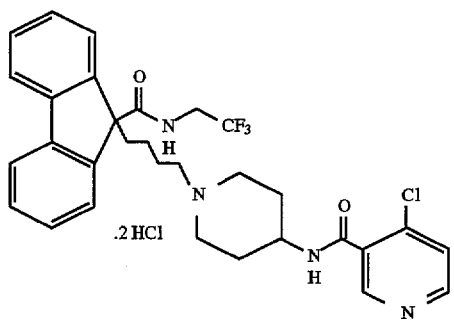

9-[4-[4-[(4-Chloro-3-pyridinyl)carbonyl]amino]-1-piperidinyl]butyl]-N-(2,2,2-trifluoroethyl)-9H-fluorene-9-carboxamide, dihydrochloride.

M.P. 165°–73° C. MS (ESI, +ions) m/z 585 (M+H)

EXAMPLE 25

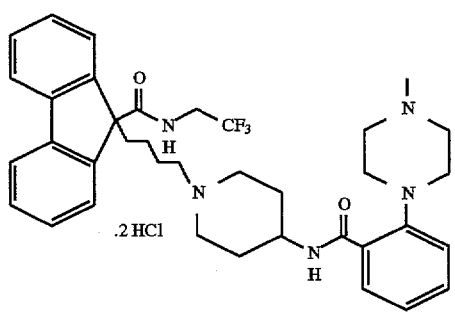

9-[4-[4-[[2-(4-Methyl-1-piperazinyl)benzoyl]amino]-1-piperidinyl]butyl]-N-(2,2,2-trifluoromethyl)-9H-fluorene-9-carboxamide, dihydrochloride.

MS (electrospray, +ions) m/z 648 (M+H)

EXAMPLE 26

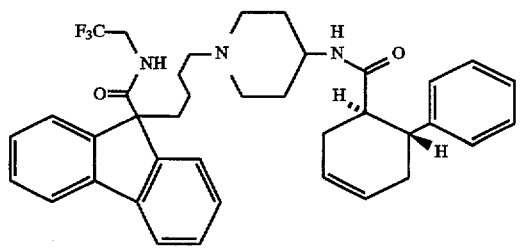

trans-9-[4-[4-[[(1-Phenyl-3-cyclohexen-1-yl)carbonyl]amino]-1-piperidinyl]butyl]-N-(2,2,2-trifluoroethyl)-9H-fluorene-9-carboxamide, monohydrochloride.

M.P. 160°–163° C. MS (electrospray, +ions) m/z 630 (M+H)

EXAMPLE 27

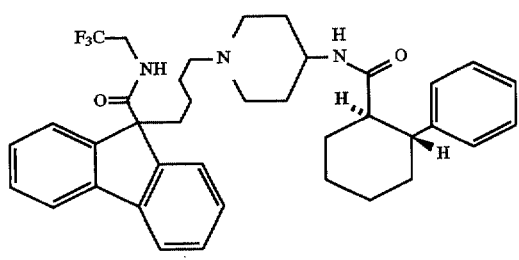

trans-9-[4-[4-[[(2-Phenylcyclohexyl)carbonyl]amino]-1-piperidinyl]butyl]-N-(2,2,2-trifluoroethyl)-9H-fluorene-9-carboxamide, monohydrochloride.

M.P. 156°–159° C. MS (electrospray, +ions) m/z 632 (M+H)

EXAMPLE 28

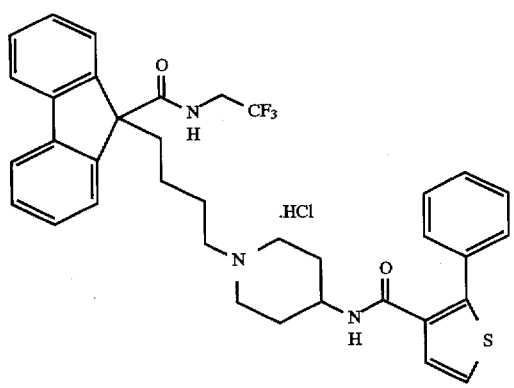

9-[4-[4-[[(2-Phenyl-3-thienyl)carbonyl]amino]-1-piperidinyl]butyl]-N-(2,2,2-trifluoroethyl)-9H-fluorene-9-carboxamide, monohydrochloride.

MS (ES, +ions) m/z 632 (M+H)

EXAMPLE 29

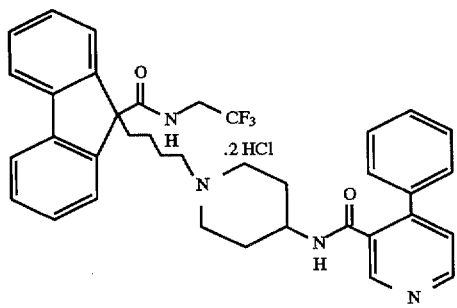

9-[4-[4-[(4-Phenyl-3-pyridinyl)carbonyl]amino]-1-piperidinyl]butyl]-N-(2,2,2-trifluoroethyl)-9H-fluorene-9-carboxamide, dihydrochloride.

M.P. 144°–50° C. MS (ESI, +ions) m/z 627 (M+H)
Elemental Anal. Calc'd for $C_{37}H_{37}F_3N_4O_2$+2 HCl+1.2 $H_2O$:
C, 61.62; H, 5.79; N, 7.77 Found: C, 61.64; H, 5.80; N, 7.32

EXAMPLE 30

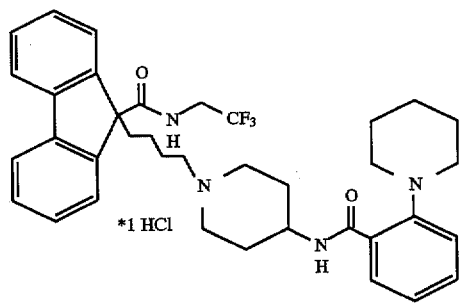

9-[4-[4-[[2-(1- Piperidinyl)benzoyl]amino]-1-piperidinyl]butyl]-N-(2,2,2-trifluoroethyl)-9H-fluorene-9-carboxamide, monohydrochloride.

MS (electrospray, +ions) m/z 633 (M+H)

EXAMPLE 31

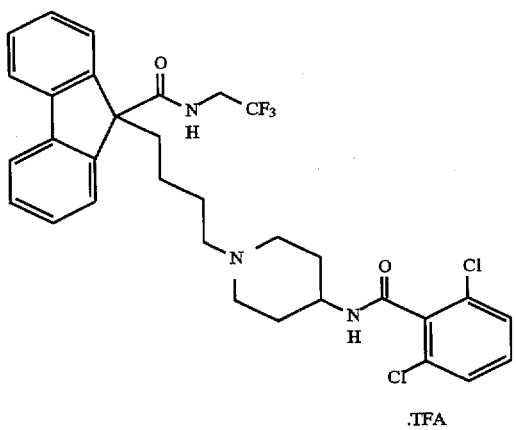

MS (ESI, +ions) m/z 618 (M+H)

EXAMPLE 32

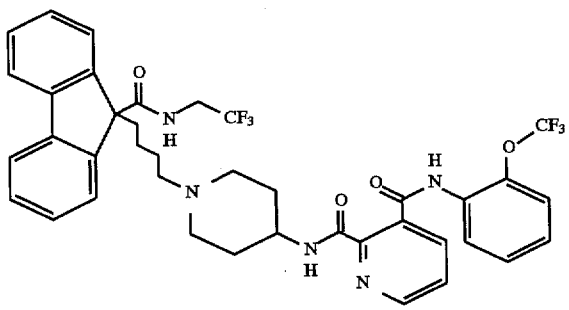

MS (ESI, +ions) m/z 754 (M+H)

EXAMPLE 33

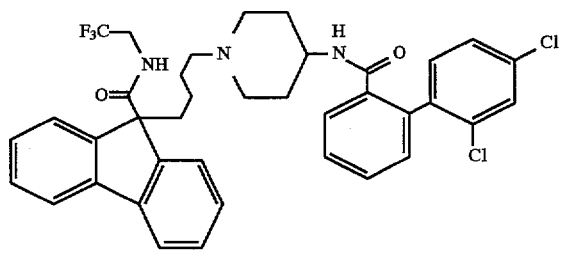

9-[4-[4-[[2-(2,4-Dichlorophenyl)benzoyl]amino]-1-piperidinyl]butyl]-N-(2,2,2-trifluoroethyl)-9H-fluorene-9-carboxamide, monohydrochloride.

M.P. 123°–128° C. MS (electrospray, –ions) m/z 694 (M+H)

EXAMPLE 34

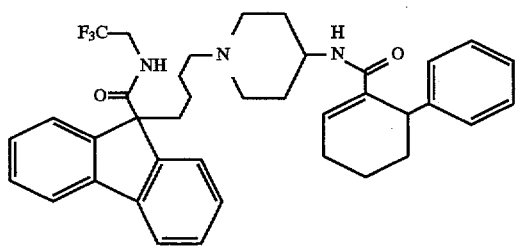

9-[4-[4-[[(6-Phenyl-1-cyclohexen-1-yl)carbonyl]amino]-1-piperidinyl]butyl]-N-(2,2,2-trifluoroethyl)-9H-fluorene-9-carboxamide, monohydrochloride.

M.P. 110°–114° C. MS (electrospray, –ions) m/z 630 (M+H)

EXAMPLE 35

9-[4-[4-[(2,5-Difluorobenzoyl)amino]-1-piperidinyl]butyl]-N-(2,2,2-trifluoroethyl)-9H-fluorene-9-carboxamide, monohydrochloride.

M.P. 80°–84° C. MS (ESI, +ions) m/z 586 (M+H)
Elemental Anal. Calc'd for $C_{32}H_{32}F_5N_3O_2 + 1$ HCl + 1.2 $H_2O$:
C, 59.71; H, 5.54; N, 6.53 Found: C, 59.68; H, 5.53; N, 6.44

EXAMPLE 36

9-[4-[4-[[[2-[2,2,2-Trifluoro-1-(2,2,2-trifluoromethyl)ethoxy]-3-pyridinyl]carbonyl]amino]-1-piperidinyl]butyl]-N-(2,2,2-trifluoroethyl)-9H-fluorene-9-carboxamide, dihydrochloride.

MS (ESI, +ions) 717 (M+H); (–ions) 715 (M–H)

EXAMPLE 37

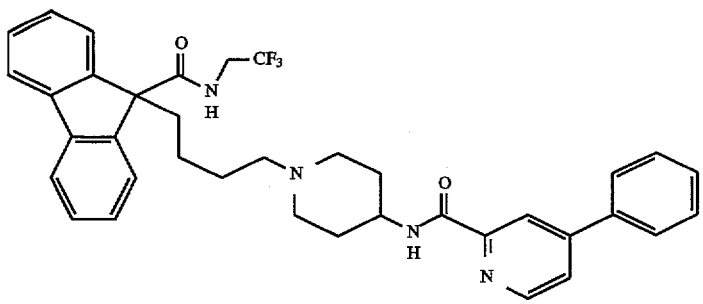

dihydrochloride salt

9-[4-[4-[[(4-Phenyl-2-pyridinyl)carbonyl]amino]-1-piperidinyl]butyl]-N-(2,2,2-trifluoroethyl)-9H-fluorene-9-carboxamide, dihydrochloride.

MS (ESI, +ions) m/z 627 (M+H)⁺; (ESI, −ions) m/z 625 (M−H) Elemental Anal. Calc'd for $C_{37}H_{37}F_3N_4O_2$+2 HCl+ 0.44 Et₂O+3.0 H₂O: C, 59.21; H, 6.33; N, 7.13; F, 7.25; Cl, 9.02 Found: C, 59.59; H, 6.01; N, 6.97; F, 7.10; Cl, 9.17

EXAMPLE 38

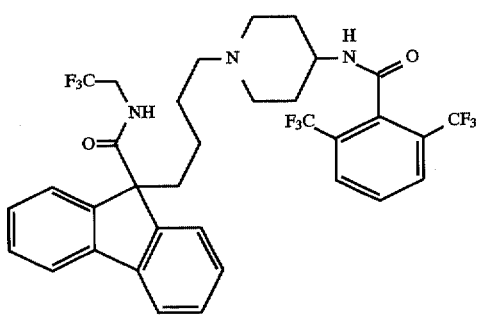

9-[4-[4-[[2,6-Bis(trifluoromethyl)benzoyl]amino]-1-piperidinyl]butyl]-N-(2,2,2-trifluoroethyl)-9H-fluorene-9-carboxamide, monohydrochloride.

M.P. 145°–150° C. MS (electrospray, −ions) m/z 686 (M+H)

EXAMPLE 39

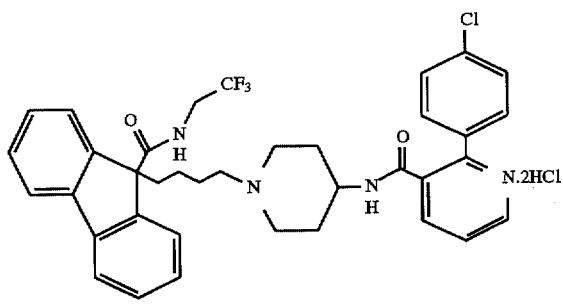

contains 0.05 mole of ethyl ether

9-[4-[4-[[[2-(4-Chlorophenyl)-3-pyridinyl]carbonyl]amino]-1-piperidinyl]butyl]-N-(2,2,2-trifluomethyl)-9H-fluorene-9-carboxamide, dihydrochloride.

MS (ESI-NH₃, +ions) (M+H) 661

EXAMPLE 40

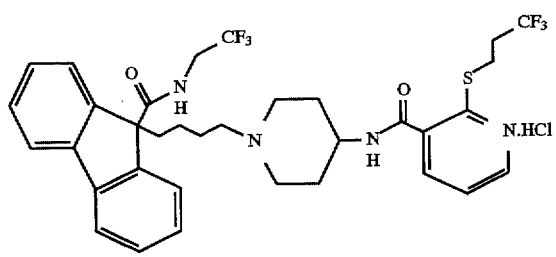

contains 0.12 mole of ethyl ether

N-(2,2,2-Trifluoroethyl)-9-[4-[4-[[[2-[(3,3,3-trifluoropropyl)thio]-3-pyridinyl]carbonyl]amino]-1-piperidinyl]butyl]-9H-fluorene-9-carboxamide, monohydrochloride.

MS (ESI-NH₃, +ions) (M+H) 679

EXAMPLE 41

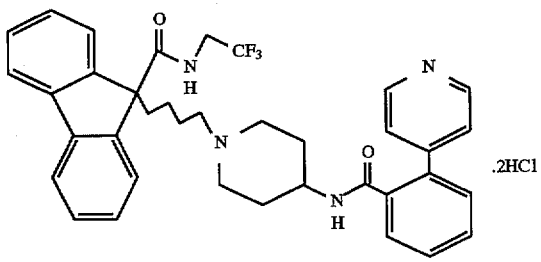

9-[4-[4-[[2-(4-Pyridinyl)benzoyl]amino]-1-piperidinyl]butyl]-N-(2,2,2-trifluoroethyl)-9H-fluorene-9-carboxamide, dihydrochloride.

M.P. 140°–150° C. (shrinking commencing at 115° C.) MS (electrospray, −ions) m/z 627 (M+H)⁺

Elemental Anal. Calc'd for $C_{37}H_{37}F_3N_4O_2$·2 HCl·2.14 H₂O: C, 60.21; H, 5.91; N, 7.59; Cl, 9.60; F, 7.72 Found: C, 60.21; H, 6.08; N, 8.01; Cl, 9.23; F, 7.37

EXAMPLE 42

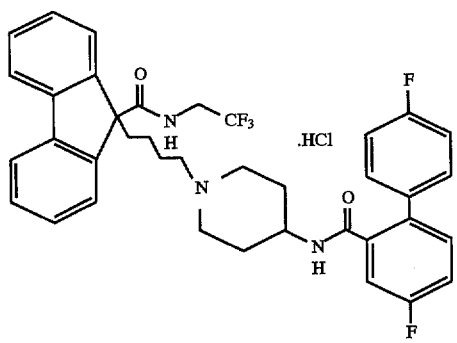

9-[4-[4-[[(4,4'-Difluoro[1,1'-biphenyl]-2-yl)carbonyl]amino]-1-piperidinyl]butyl]-N-(2,2,2-trifluomethyl)-9H-fluorene-9-carboxamide, monohydrochloride.

M.P. 131°–34° C. MS (ESI, +ions) m/z 662 (M+H)

Elemental Anal. Calc'd for $C_{38}H_{36}F_5N_3O_2$+HCl+1.7 H₂O: C, 62.63; H, 5.59; N, 5.77 Found: C, 62.59; H, 5.29; N, 5.82

EXAMPLE 43

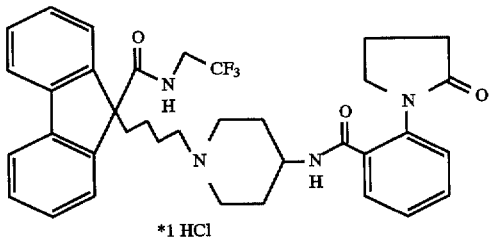

9-[4-[4-[[2-(2-Oxo-1-pyrrolidinyl)benzoyl]amino]-1-piperidinyl]butyl]-N-(2,2,2-trifluoroethyl)-9H-fluorene-9-carboxamide, monohydrochloride.

MS (electrospray, +ions) m/z 633 (M+H)

EXAMPLE 44

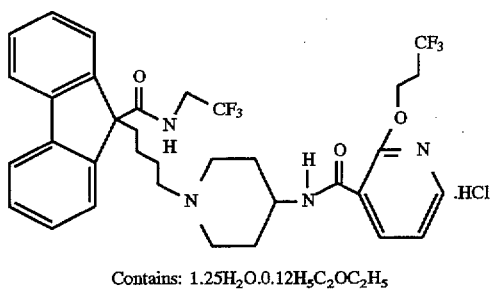

Contains: 1.25H₂O.0.12H₅C₂OC₂H₅

N-(2,2,2-Trifluoromethyl)-9-[4-[4-[[[2-(3,3,3-trifluoropropoxy)-3-pyridinyl]carbonyl]amino]-1-piperidinyl]butyl]-9H-fluorene-9-carboxamide, monohydrochloride.

MS (ESI, +ion) m/z 663 (M+H); (−ion) 661 (M−H)

Elemental Anal. Calc'd for $C_{34}H_{36}N_4O_3F_6 \cdot HCl \cdot 1.25\ H_2O \cdot 0.12\ H_5C_2OC_2H_5$ C, 56.69; H, 5.62; N, 7.67; Cl, 4.85; F, 15.60 Found: C, 56.98; H, 5.52; N, 7.63; Cl, 4.74; F, 15.31

EXAMPLE 45

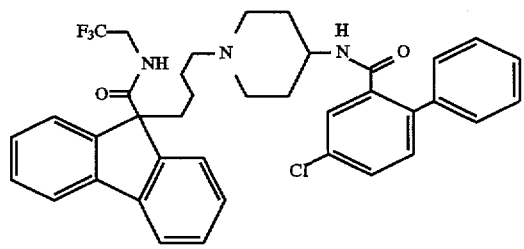

9-[4-[4-[[(4-Chloro[1,1-biphenyl]-2-yl)carbonyl]amino]-1-piperidinyl]butyl]-N-(2,2,2-trifluoroethyl)-9H-fluorene-9-carboxamide, monohydrochloride.

M.P. 123°–128° C. MS (electrospray, −ions) m/z 661 (M+H)

EXAMPLE 46

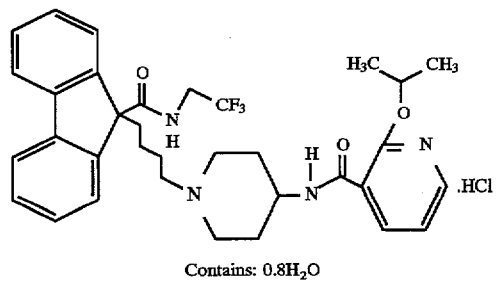

Contains: 0.8H₂O

9-[4-[4-[[[2-(1-Methylethoxy)-3-pyridinyl]carbonyl]amino]-1-piperidinyl]butyl]-N-(2,2,2-trifluoroethyl)-9H-fluorene-9-carboxamide, monohydrochloride.

MS (ESI, +ion) m/z 609 (M+H); (−ion) 607 (M−H)

Elemental Anal. Calc'd for $C_{34}H_{39}N_4O_3F_3 \cdot HCl \cdot 0.8\ H_2O$: C, 61.91; H, 6.36; N, 8.49; Cl, 5.38; F, 8.64 Found: C, 61.63; H, 6.45; N, 8.31; Cl, 5.80; F, 8.50

EXAMPLE 47

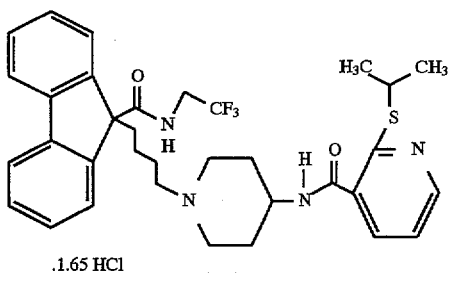

.1.65 HCl

Contains: 1.5H₂O

9-[4-[4-[[[2-[(1-Methylethyl)thio]-3-pyridinyl]carbonyl]amino]-1-piperidinyl]butyl]-N-(2,2,2-trifluoroethyl)-9H-fluorene-9-carboxamide, dihydrochloride.

MS (ESI, +ion)m/z 625 (M+H); (−ion) 623 (M−H)

Elemental Anal. Calc'd for $C_{34}H_{39}N_4O_2SF_3 \cdot 1.65\ HCl \cdot 1.5\ H_2O$: C, 57.36; H, 6.18; N, 7.87; Cl, 8.22; F, 8.01; S, 4.50 Found: C, 57.56; H, 6.37; N, 7.74; Cl, 8.12; F, 8.06 S. 4.47

EXAMPLE 48

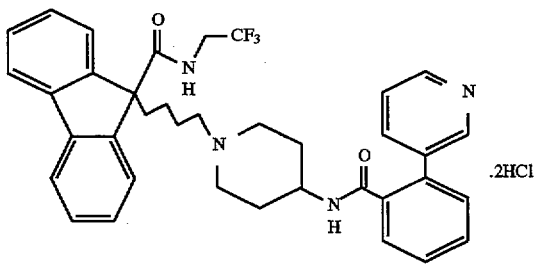

contains 2.14 moles H₂O
Eff. Mol Wt. = 738.105

9-[4-[4-[[2-(3-Pyridinyl)benzoyl]amino]-1-piperidinyl]butyl]-N-(2,2,2-trifluoroethyl)-9H-fluorene-9-carboxamide, dihydrochloride.

M.P. 120°–130° C. (shrinking commencing at 110° C.) MS (electrospray, −ions) m/z (M+H)⁺=627

Elemental Anal. Calc'd for $C_{37}H_{37}F_3N_4O_2 \cdot 2\ HCl \cdot 2.14\ H_2O$: C, 60.21; H, 5.91; N, 7.59; Cl, 9.60; F, 7.72; Found: C, 60.26; H, 6.26; N, 7.04; Cl, 9.09; F, 7.15

EXAMPLE 49

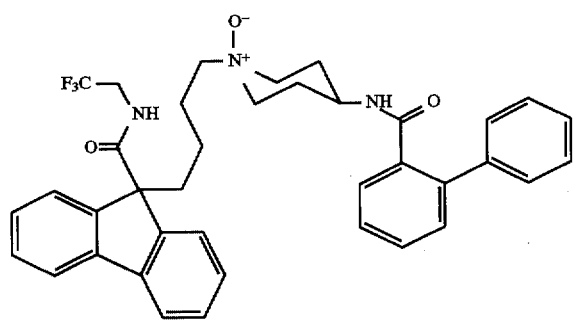

9-[4-[4-[[(1,1-Biphenyl]-4-ylcarbonyl)amino]-1-piperidinyl]-3,3-difluorobutyl]-N-(2,2,2-trifluoroethyl)-9H-fluorene-9-carboxamide, N-oxide.

M.P. 185°–188° C. MS (electrospray) (M+H)$^+$ 642; (M–H)$^-$ 640

EXAMPLE 50

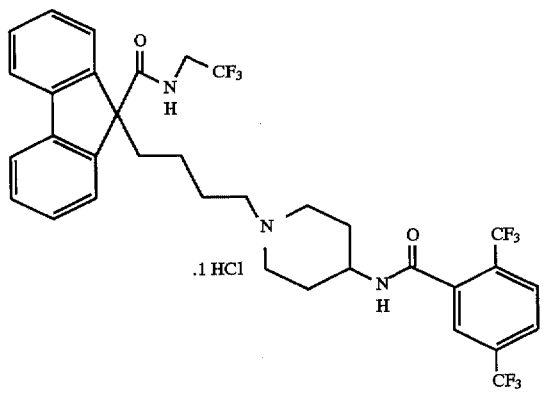

9-[4-[4-[[2,5-Bis(trifluoromethyl)benzoyl]amino]-1-piperidinyl]butyl]-N-(2,2,2-trifluomethyl)-9H-fluorene-9-carboxamide, monohydrochloride.

MS (electrospray, +ions) m/z 686 (M+H)

EXAMPLE 51

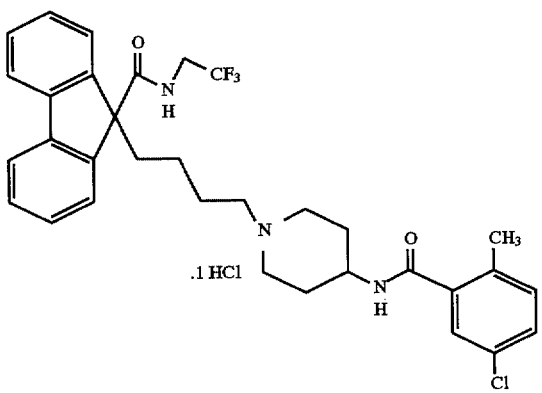

9-[4-[4-[(5-Chloro-2-methylbenzoyl)amino]-1-piperidinyl]butyl]-N-(2,2,2-trifluoroethyl)-9H-fluorene-9-carboxamide, monohydrochloride.

MS (electrospray, +ions) m/z 598 (M+H)

EXAMPLE 52

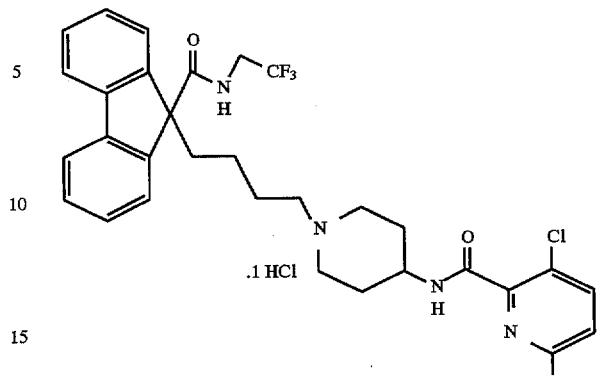

9-[4-[4-[[(3,6-Dichloro-2-pyridinyl)carbonyl]amino]-1-piperidinyl]butyl]-N-(2,2,2-trifluoroethyl)-9H-fluorene-9-carboxamide, monohydrochloride.

MS (electrospray, +ions) m/z 619 (M+H) [2 Cl isotope pattern]

EXAMPLE 53

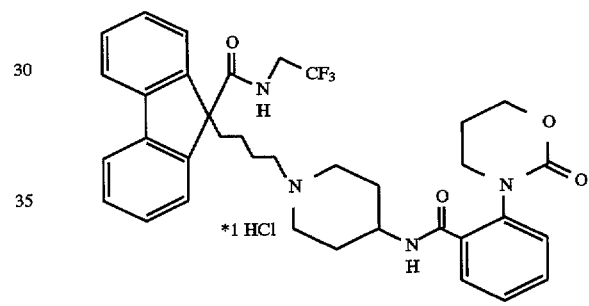

9-[4-[4-[[2-(Tetrahydro-2-oxo-2H-1,3-oxazin-3-yl)benzoyl]amino]-1-piperidinyl]butyl]-N-(2,2,2-trifluoroethyl)-9H-fluorene-9-carboxamide, monohydrochloride.

EXAMPLE 54

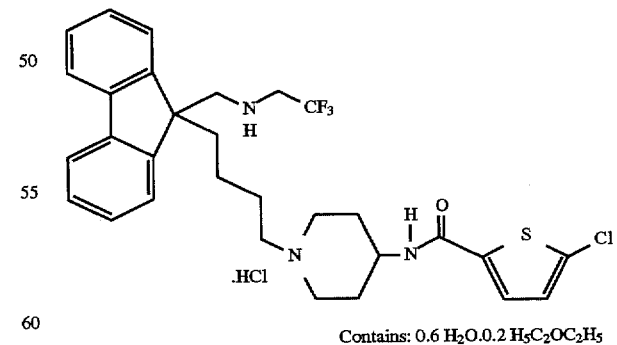

Contains: 0.6 H$_2$O.0.2 H$_5$C$_2$OC$_2$H$_5$

9-[4-[4-[[(5-Chloro-2-thienyl)carbonyl]amino]-1-piperidinyl]butyl]-N-(2,2,2-trifluoroethyl)-9H-fluorene-9-carboxamide, monohydrochloride.

MS (ESI, +ion)m/z 590 (M+H) 1 Cl Isotope Pattern

Elemental Anal. Calc'd for $C_{30}H_{31}N_3O_2ClSF_3 \cdot HCl \cdot 0.6$ $H_2O \cdot 0.2\ H_5C_2OC_2H_5$: C, 56.72; H, 5.44; N, 6.44; Cl, 10.87; F, 8.74 S, 4.92 Found: C, 56.43; H, 5.37; N, 6.38; Cl, 10.70; F, 8.73 S, 5.36

EXAMPLE 55

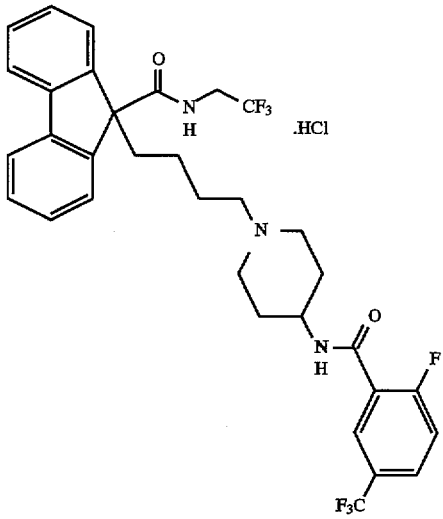

9-[4-[4-[[2-Fluoro-5-(trifluoromethyl)benzoyl]amino]-1-piperidinyl]butyl]-N-(2,2,2-trifluoroethyl)-9H-fluorene-9-carboxamide, monohydrochloride.

$(M+H)^+$ 636; $(M-H)^-$ 634

EXAMPLE 56

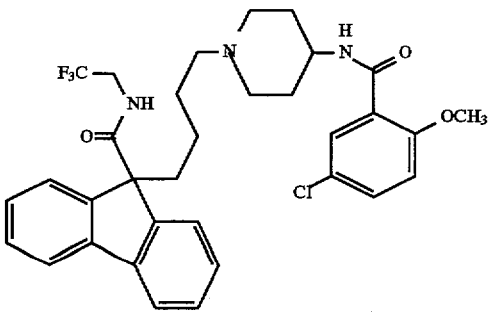

9-[4-[4-[(5-Chloro-2-methoxybenzoyl)amino]-1-piperidinyl]butyl]-N-(2,2,2-trifluoroethyl)-9H-fluorene-9-carboxamide, monohydrochloride.

M.P. 108°14 113° C. MS (electrospray, −ions) m/z 615 (M+H)

EXAMPLE 57

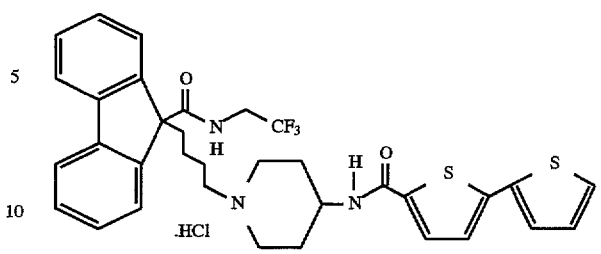

Contains: $H_2O$. 0.15 $H_5C_2OC_2H_5$

9-[4-[4-[[(2:2'-Bithiophen-5-yl)carbonyl]amino]-1-piperidinyl]butyl]-N-(2,2,2-trifluoroethyl)-9H-fluorene-9-carboxamide, monohydrochloride.

MS (ESI, +ion) m/z 638 (M+H)

Elemental Anal. Calc'd for $C_{34}H_{34}N_3O_2S_2F_3 \cdot HCl \cdot H_2O \cdot 0.15\ H_5C_2OC_2H_5$: C, 59.08; H, 5.52; N, 5.97; Cl, 5.04; F, 8.10 S, 9.12 Found: C, 58.88; H, 5.41; N, 5.90; Cl, 4.97; F, 8.24 S, 9.22

EXAMPLE 58

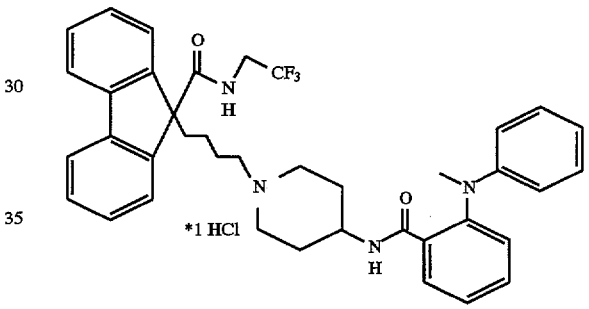

9-[4-[4-[[2-(Phenylmethylamino)benzoyl]amino]-1-piperidinyl]butyl]-N-(2,2,2-trifluoroethyl)-9H-fluorene-9-carboxamide, monohydrochloride.

ESI $(M+H)^+$ 655

EXAMPLE 59

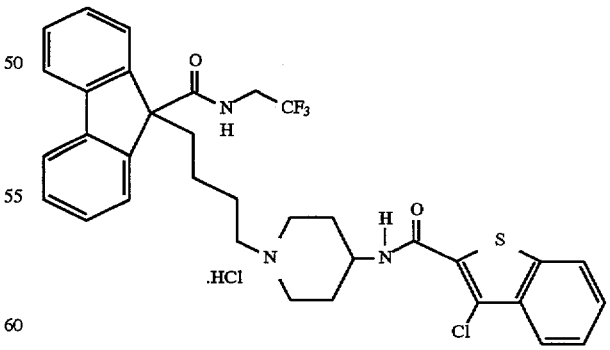

9-[4-[4-[[(3-Chlorobenzo[b]thiophen-2-yl)carbonyl]amino]-1-piperidinyl]butyl]-N-(2,2,2-trifluoroethyl)-9H-fluorene-9-carboxamide, monohydrochloride.

MS (ESI, +ions) m/z 640 (M+H) 1 Cl Isotope pattern

EXAMPLE 60

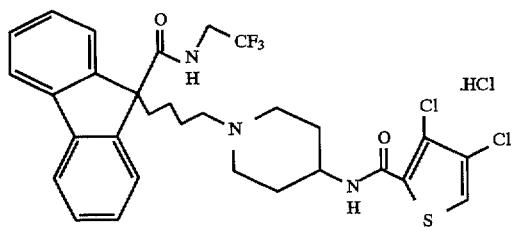

9-[4-[4-[[(3,4-Dichloro-2-thienyl)carbonyl]amino]-1-piperidinyl]butyl]-N-(2,2,2-trifluoroethyl)-9H-fluorene-9-carboxamide, monohydrochloride.

M.P. 110°–120° C. (shrinking commencing at 95° C. MS (electrospray, –ions) m/z (M+H) 624; 2 Cl isotope pattern

EXAMPLE 61

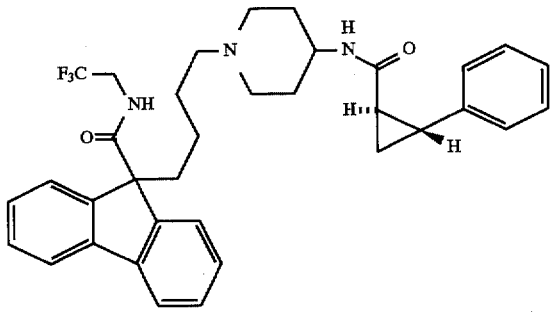

trans-9-[4-[4-[[(2-Phenylcyclopropyl)carbonyl]amino]-1-piperidinyl]butyl]-N-(2,2,2-trifluoromethyl)-9H-fluorene-9-carboxamide, monohydrochloride.

M.P. 118°–126° C. MS (electrospray, –ions) m/z 590 (M+H)

Elemental Anal. Calc'd for $C_{35}H_{38}F_3N_3O_2$+HCl+0.82 $H_2O$+0.36 dioxane C, 65.07; H, 6.52; N, 6.25; Cl, 5.27; F, 8.47 Found: C, 65.07; H, 6.50; N, 6.12; Cl, 5.36; F, 8.25

EXAMPLE 62

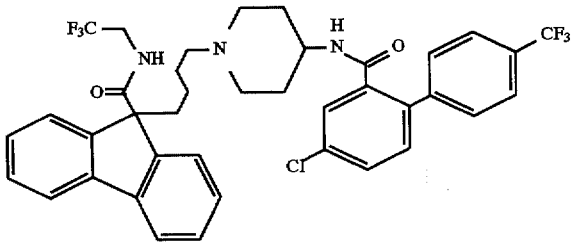

9-[4-[4-[[[4-Chloro-4'-(trifluoromethyl)[1,1'-biphenyl]-2-yl]-carbonyl]amino]-1-piperidinyl]butyl]-N-(2,2,2-trifluomethyl)-9H-fluorene-9-carboxamide, monohydrochloride M.P. 123°–128° C. MS (electrospray, –ions) m/z 728 (M+H)

Elemental Anal. Calc'd for $C_{39}H_{36}ClF_6N_3O_2$+HCl+0.5 $H_2O$: C, 60.55; H, 4.95; N, 5.43; Cl, 9.17 Found: C, 60.54; H, 4.84; N, 5.22; Cl, 8.91

EXAMPLE 63

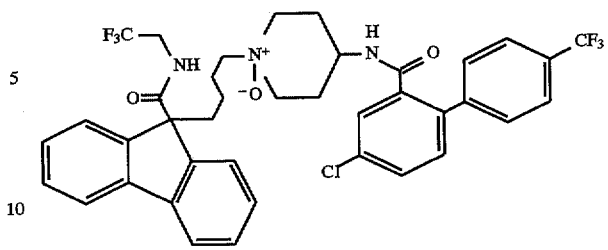

9-[4-[4-[[[4-Chloro-4'-(trifluoromethyl)[1,1'-biphenyl]-2-yl]carbonyl]amino]-1-piperidinyl]butyl]-N-(2,2,2-trifluoroethyl)-9H-fluorene-9-carboxamide, N-oxide.

M.P. 142°–144° C. MS (electrospray, –ions) m/z 743 (M–H)

Elemental Anal. Calc'd for $C_{39}H_{36}ClF_6N_3O_3$+0.88 $H_2O$: C, 61.63; H, 5.01; N, 5.53; Cl, 4.66 Found: C, 61.64; H, 5.05; N, 5.42; Cl, 5.02

EXAMPLE 64

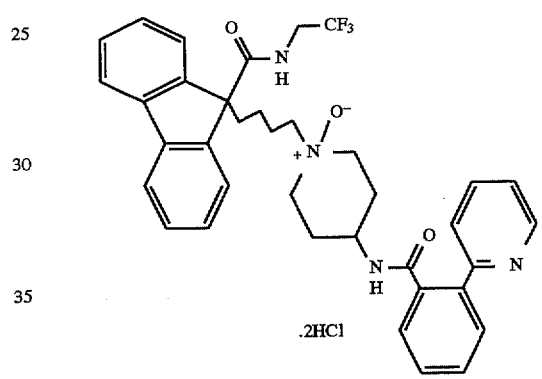

9-[4-[4-[(2-Pyridinylbenzoyl)amino]-1-piperidinyl]butyl]-N-(2,2,2-trifluomethyl)-9H-fluorene-9-carboxamide, N-oxide, dihydrochloride.

MS (M+H)$^+$ 643; (M–H)$^–$ 641

Elemental Anal. Calc'd for $C_{37}H_{37}F_3N_4O_3$+2 HCl+1.94 $H_2O$: C, 59.21; H, 5.76; N, 7.46; F, 7.59; Cl, 9.45 Found: C, 59.61; H, 5.81; N, 7.25; F, 7.19; Cl, 9.05

EXAMPLE 65

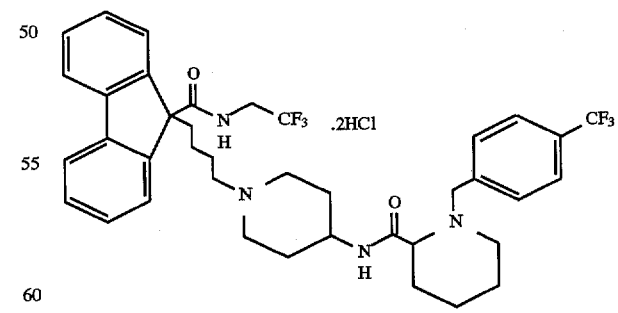

N-(2,2,2-Trifluoroethyl)-9-[4-[4-[[[1-[[4-(trifluoromethyl)phenyl]methyl]-2-piperidinyl]carbonyl]amino]-1-piperidinyl]butyl]-9H-fluorene-9-carboxamide, dihydrochloride.

MS (ES, +ions) m/z 715 [M+H]

Elemental Anal. Calc'd for $C_{39}H_{44}F_6N_4O_2+2\ H_2O+2$ HCl: C, 56.87; H, 6.12; N, 6.80 Found: C, 57.01; H, 6.01; N, 6.74

EXAMPLE 66

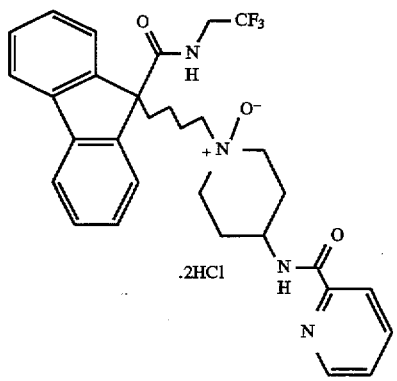

N-[1-[4-[9-[[(2,2,2-Trifluoroethyl)amino]carbonyl]-9H-fluoren-9-yl]butyl]-4-piperidinyl]-2-pyridinecarboxamide, N-oxide, dihydrochloride.
MS $(M+H)^+$ @ 567; $(M-H)^-$ @ 565; $(2M+H)^+$ @ 1133

Elemental Anal. Calc'd for $C_{31}H_{33}F_3N_4O_3+2\ HCl+1.7\ H_2O$: C, 55.56; H, 5.78; N, 8.36; F, 8.50; Cl, 10.58 Found: C, 55.89; H, 5.81; N, 8.18; F, 8.66; Cl, 10.18

EXAMPLE 67

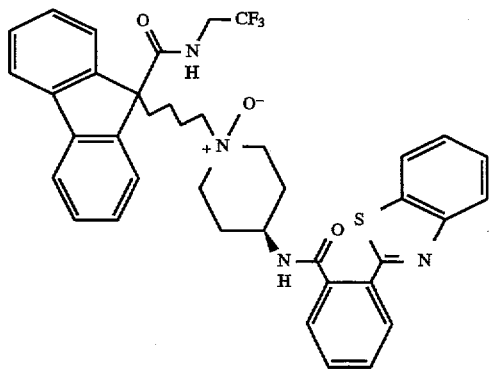

trans-9-[4-[4-[[2-(2-Benzothiazolyl)benzoyl]amino]-1-piperidinyl]butyl]-N-(2,2,2-trifluomethyl)-9H-fluorene-9-carboxamide, N-oxide. MS $(M+H)^+$ @ 699; $(M-H)^-$ @ 697

Elemental Anal. Calc'd for $C_{39}H_{37}F_3N_4O_3S+1.5\ H_2O+0.3\ C_6H_{14}$: C, 65.19; H, 5.93; N, 7.45; F, 7.58; Cl, 4.27 Found: C, 65.12; H, 5.85; N, 7.29; F, 7.23; Cl, 4.29

EXAMPLE 68

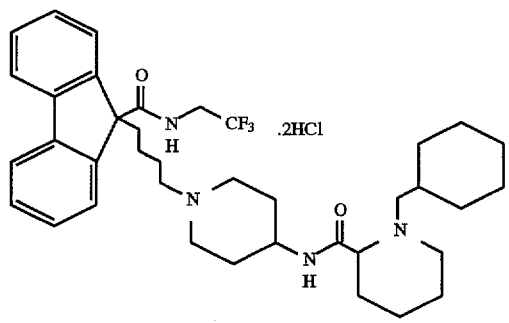

9-[4-[4-[[[1-(Cyclohexylmethyl)-2-piperidinyl]carbonyl]amino]-1-piperidinyl]butyl]-N-(2,2,2-trifluoroethyl)-9H-fluorene-9-carboxamide, dihydrochloride.

MS (ES, +ions) m/z 653 [M+H]

Elemental Anal. Calc'd for $C_{38}H_{53}Cl_2F_3N_4O_2+1.5\ H_2O$: C, 60.63; H, 7.50; N, 7.44; F, 7.57; Cl, 9.42 Found: C, 60.73: H, 7.74; N, 7.65; F, 7.22; Cl, 9.85

EXAMPLE 69

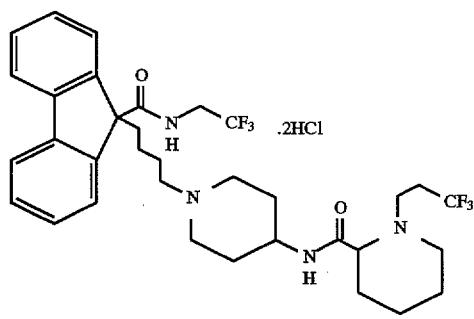

N-(2,2,2-Trifluoroethyl)-9-[4-[4-[[[1-(3,3,3-trifluoropropyl)-2-piperidinyl]carbonyl]amino]-1-piperidinyl]butyl]-9H-fluorene-9-carboxamide, dihydrochloride.

MS (ES, +ions) m/z 653 [M+H]

Elemental Anal. Calc'd for $C_{34}H_{44}Cl_2F_6N_4O_2+1.5\ H_2O$: C, 54.26; H, 6.29; N, 7.44; F, 15.14 Found: C, 54.40; H, 6.21; N, 7.38; F, 15.53

EXAMPLE 70

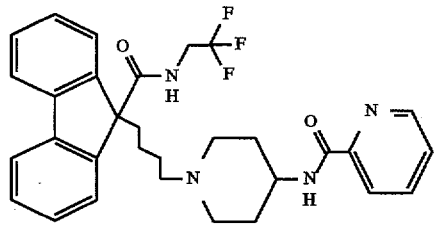

MS (ESI+ions) m/z 551 (M+H)

EXAMPLE 71

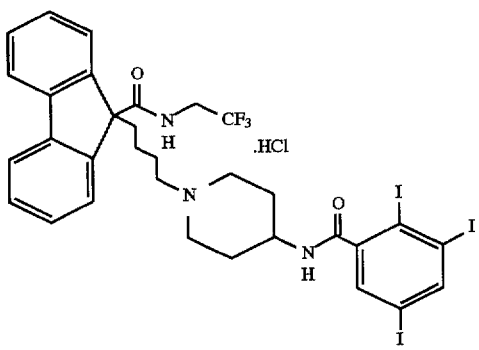

N-(2,2,2-Trifluoroethyl)-9-[4-[4-[(2,3,5-triiodobenzoyl)amino]-1-piperidinyl]butyl]-9H-fluorene-9-carboxamide, monohydrochloride.

M.P. 178°–182° C. MS (ES, +ions) m/z 928 (M+H)

Elemental Anal. Calc'd for $C_{32}H_{32}ClF_3I_3N_3O_2 + 0.5\ H_2O$: C, 39.51; H, 3.42; N, 4.32; Cl, 3.64 Found: C, 39.40; H, 3.25; N, 4.27; Cl, 3.61

EXAMPLE 72

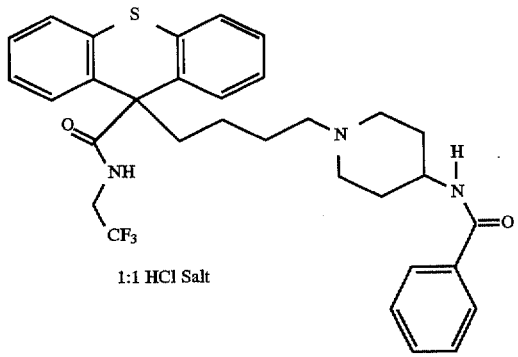

9-[4-[4-(Benzoylamino)-1-piperidinyl]butyl]-N-(2,2,2-trifluoroethyl)-9H-thioxanthene-9-carboxamide, monohydrochloride.

M.P. or B.P. 145°–150° C. MS (ES, +ions) m/z 582 (M+H)

Elemental Anal. Calc'd for $C_{32}H_{34}N_3O_2F_3S + 1.0\ HCl + 0.75\ H_2O$: C, 60.94; H, 5.67; N, 6.66; F, 9.04 Found: C, 60.97; H, 6.00; N, 6.26; F, 9.15.

EXAMPLES 73 TO 159

The following compounds were prepared by robotics procedures as described below.

ROBOTICS PROCEDURES

Robotic Method for the Preparation of Amides

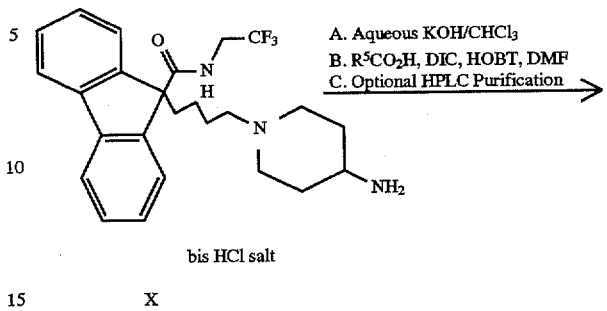

bis HCl salt

X (Example 11 Part C)

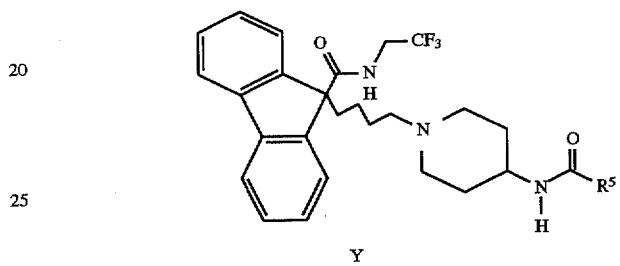

Y

A. Preparation of the diamine starting material:

A solution of the diamine bishydrochloride salt (compound X) (10 g, 19.3 mmol) in chloroform (400 mL) was washed with 1N KOH solution (3×100 mL). The organic layer was washed $H_2O$ (2×100 mL), brine (2×100 mL) and dried over $MgSO_4$. Evaporation gave the free diamine (8.8 g, 100%) as a colorless oil.

B. General Experimental for Robotics Compounds:

The following is a general procedure for the synthesis of amides according to the above equation via the coupling of carboxylic acids with the diamine. These acid-amine couplings and subsequent purifications were carried out using a Zymark Benchmate® Robotic system using an IBM PC to run the operating program and to write the Benchmate procedures.

A 16 mm×100 mm tube was charged with 1.6 mmol, 4 eq $R^5CO_2H$ acid and capped loosely with a plastic cap/column holder. The Benchmate® then carried out the following steps on the tube:

1) Added 1 mL (81 mg, 0.6 mmol, 1.5 eq) of a 81 mg/mL solution of 1-hydroxybenzotriazole hydrate in DMF.

2) Added 1 mL (75 mg, 0.6 mmol, 1.5 eq) of a 75 mg/mL solution of diisopropylcarbodiimide in $CH_2Cl_2$.

3) Added 1 mL (178 mg, 0.4 mmol, 1 eq) of a 178 mg/mL solution of diamine in $CH_2Cl_2$.

4) Washed syringe with 3 mL of $CH_2Cl_2$

5) Mixed tube contents by vortexing at speed 3 for 15 sec.

After 12–48 h the reaction was complete (no starting amine remained as determined by TLC; 10% MeOH+1% $NH_4OH$ in $CH_2Cl_2$, $I_2$).

The reaction mixture contents were then purified by ion exchange chromatography mediated by the Benchmate® Robot. The following is the standard procedure developed for purification of the coupled products by the Benchmate®:

1) Condition a Varian solid phase extraction column (1.5 g, SCX cation exchange) with 10 mL of MeOH at 0.25 ml/sec 2) Load reaction contents onto column at 0.05 mL/sec 3) Wash column with 2×10 mL of MeOH at 0.1 ml/sec 4) Wash column with 10 mL of 0.1M ammonia in MeOH at 0.1 ml/sec 5) Elute column with 4 mL of 2M ammonia in MeOH and collect into a tared receiving tube at 0.1 ml/sec 6) Elute column with 1 mL of 2M ammonia in MeOH and collect into same tared receiving tube at 0.1 ml/sec 7) Rinse syringe with 5 mL of MeOH All solution/solvent deliveries were followed by 1.8 mL of air and 10 sec push delay was used after loading reaction contents onto the ion exchange column.

The product solution was concentrated on a Savant Speed Vac (approx. 2 mm Hg for 5 h) and final solvent remnants were removed by further exposure to high vac (0.015 mm Hg, 14 h) to afford product Y, which was characterized by HPLC and MS.

MS (ES, +ions) m/z 619 (M +H)

C. Preparative HPLC Purification

In cases where the coupling reaction is carried out with carboxylic acids bearing basic substituents (for example, pyridyl or amino), the product Y isolated as above in Part B, is contaminated with the starting acid. These materials were further purified by preparative HPLC.

The samples after elution from the SCX column and speed vac concentration were reconstituted in MeOH and a small amount of trifluoroacetic acid (1 drop) was added to each. The products Y were purified by preparative chromatography using the following conditions:

Solvent A: 10% MeOH, 90% $H_2O$, 0.1% TFA

Solvent B: 90% MeOH, 10% $H_2O$, 0.1% TFA

Column: YMC ODS-A, SH-363-5, 30×250 mm I.D. S-5 µm, 120 A, No. 3025356A.

Starting % B: 0%

Final % B: 100%

Gradient time: 30 min

Flow rate: 25 mL/min

Wavelength: 220 nm

Attenuation: 9 (1.28 AUFS)

Pure fractions were combined and concentrated to afford purified product Y, which was characterized by HPLC+MS.

Please note that in the Examples 73 to 159, for structures bearing only two single bonded substituents to nitrogen, the third substituent is always hydrogen, but it is not shown explicitly in the structures. Also, please note that in the Examples 73 to 159 for structures bearing oxygens and sulfurs with only one single bonded substituent, the second substituent is always hydrogen, but is not shown explicitly in the structures.

EXAMPLE 73

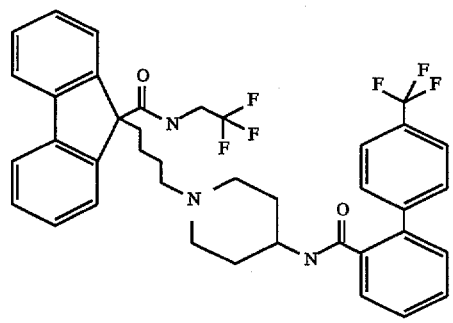

m/z 694 (M+H)

EXAMPLE 74

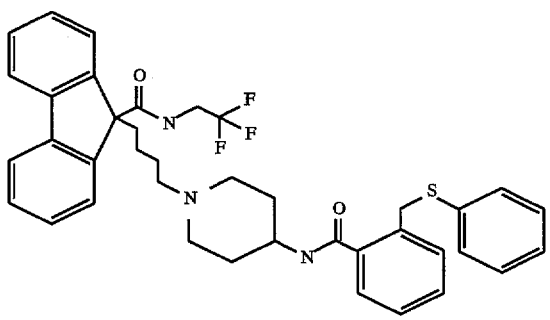

m/z 672 (M+H)

EXAMPLE 75

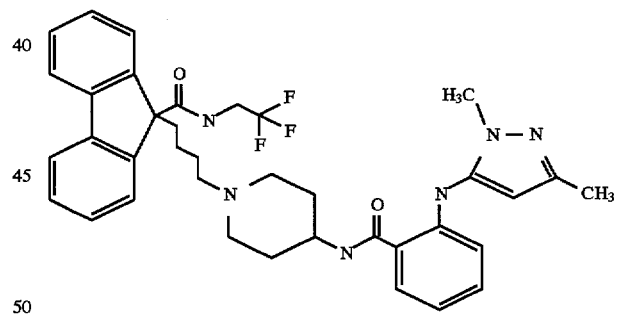

m/z 659 (M+H)

EXAMPLE 76
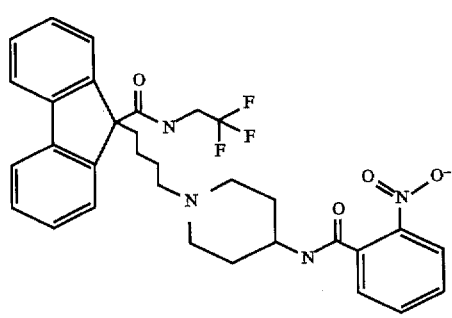
m/z 595 (M+H)
EXAMPLE 77
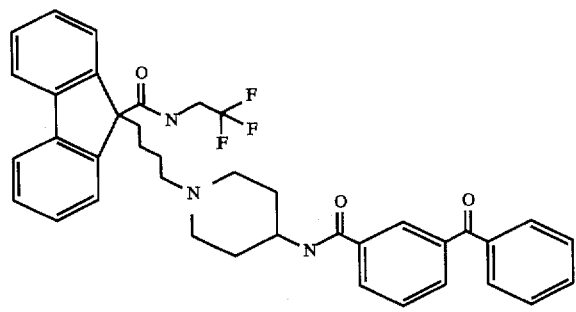
m/z 654 (M+H)
EXAMPLE 78
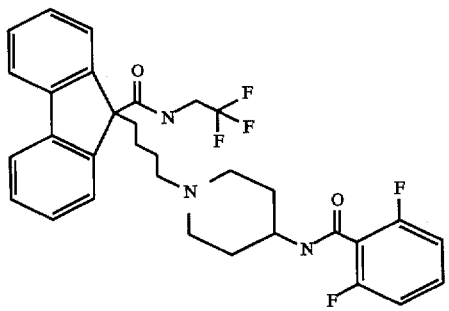
m/z 586 (M+H)
EXAMPLE 79
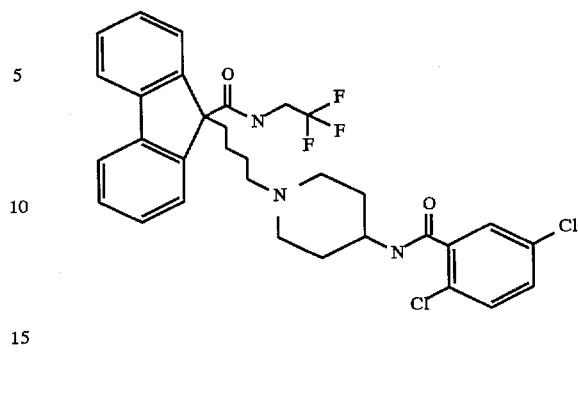
m/z 619 (M+H)
EXAMPLE 80
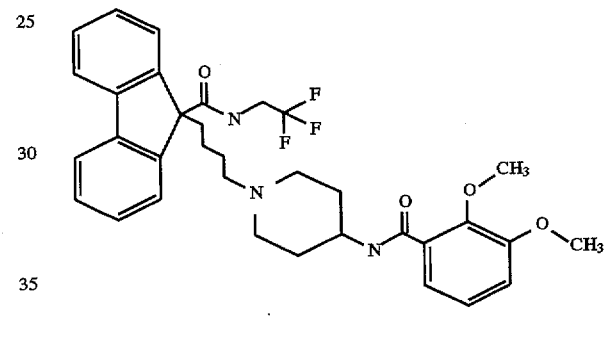
m/z 610 (M+H)
EXAMPLE 81
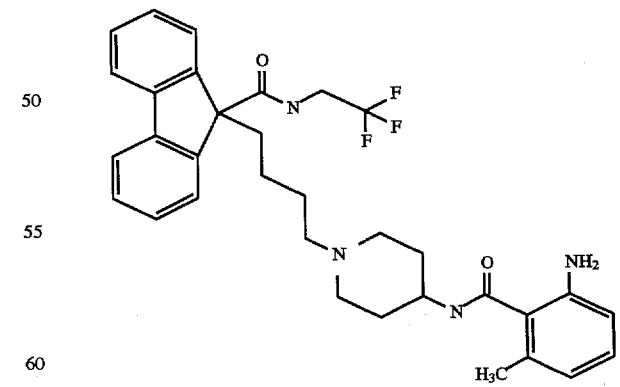
m/z 579 (M+H)

EXAMPLE 82
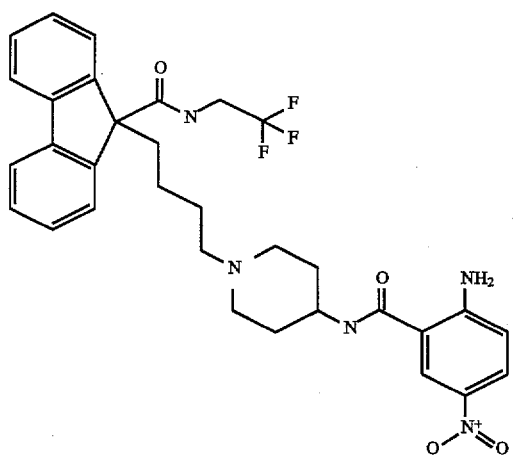
m/z 609 (M+H)
EXAMPLE 83
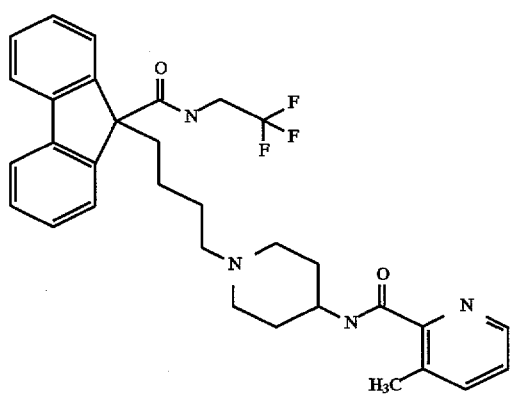
m/z 565 (M+H)
EXAMPLE 84
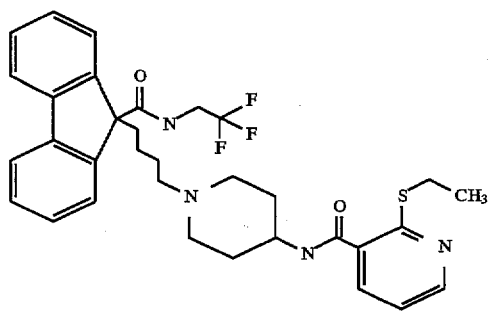
m/z 611 (M+H)
EXAMPLE 85
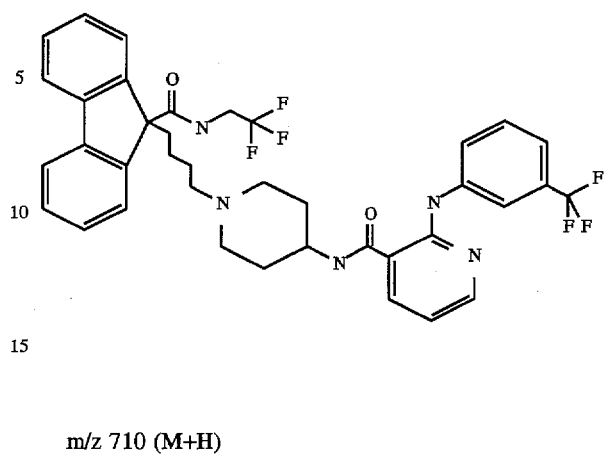
m/z 710 (M+H)
EXAMPLE 86
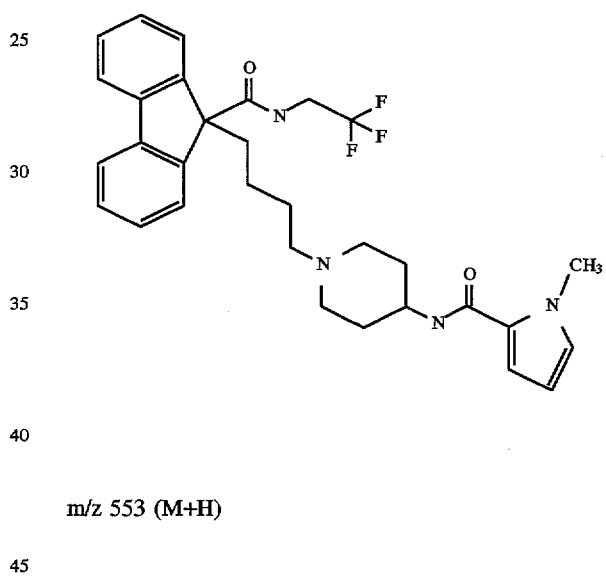
m/z 553 (M+H)
EXAMPLE 87
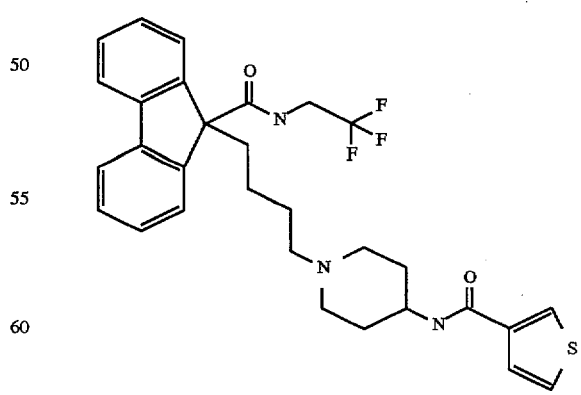
m/z 556 (M+H)

EXAMPLE 88
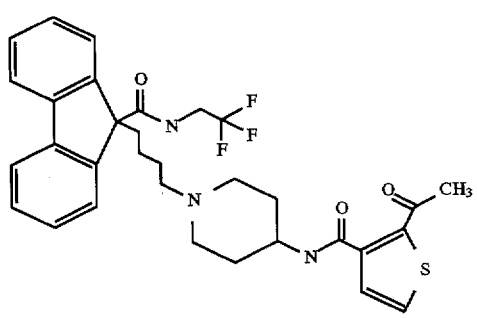
m/z 598 (M+H)
EXAMPLE 89
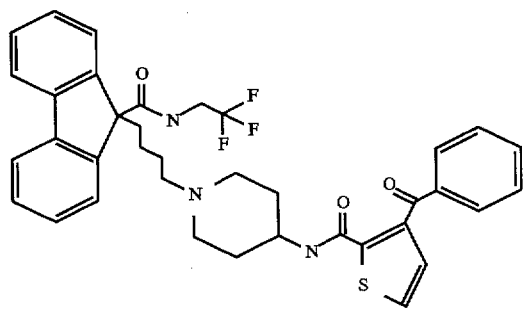
m/z 660 (M+H)
EXAMPLE 90
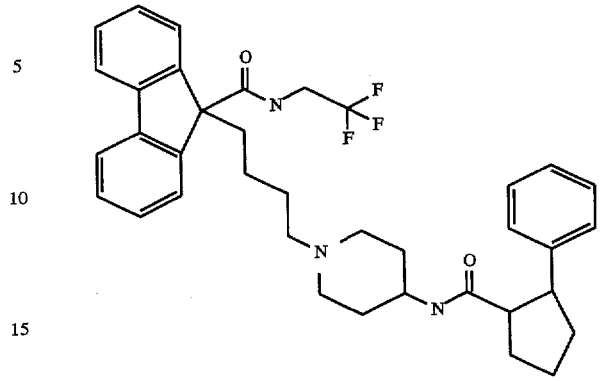
m/z 618 (M+H)
EXAMPLE 91
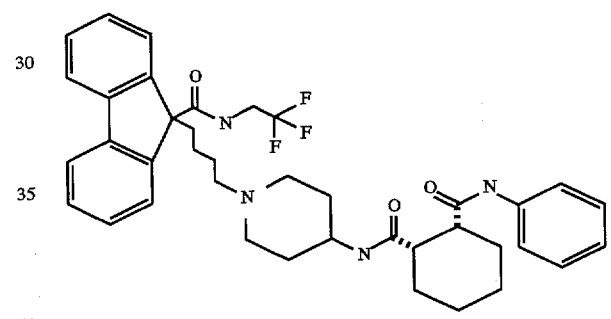
m/z 675 (M+H)
EXAMPLE 92
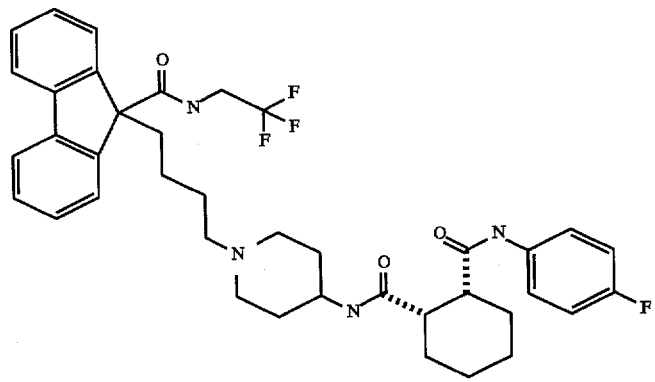

EXAMPLE 93
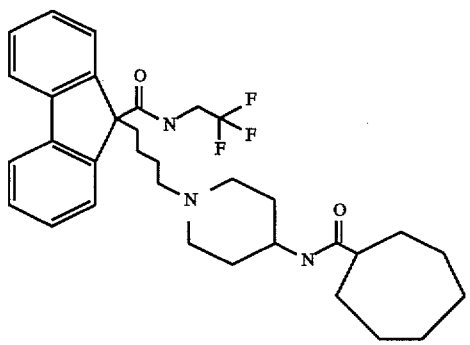
m/z 570 (M+H)
EXAMPLE 94
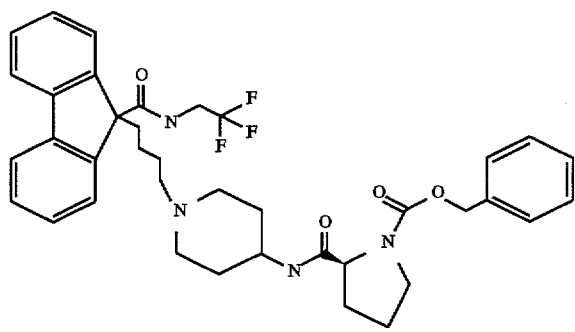
m/z 677 (M+H)
EXAMPLE 95
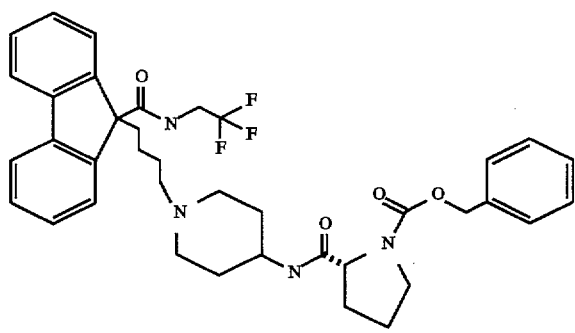
m/z 677 (M+H)
EXAMPLE 96
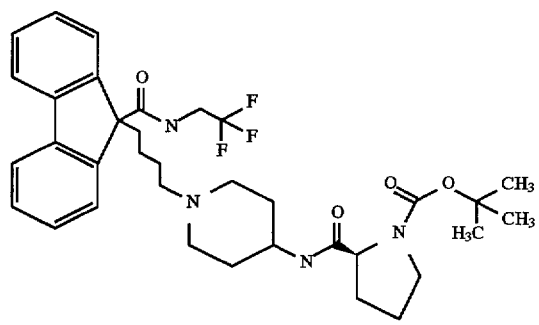
m/z 643 (M+H)
EXAMPLE 97
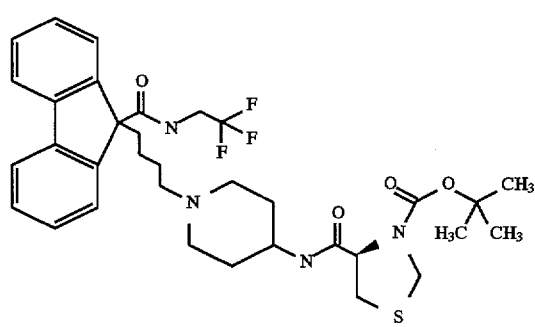
m/z 661 (M+H)
EXAMPLE 98
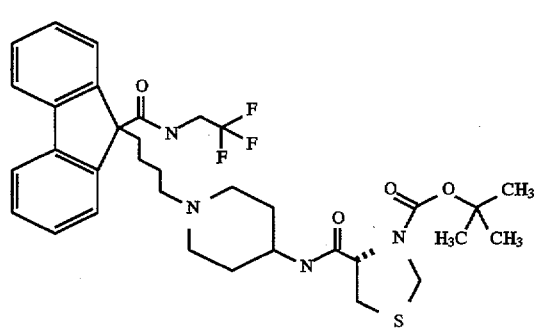
m/z 661 (M+H)

EXAMPLE 99
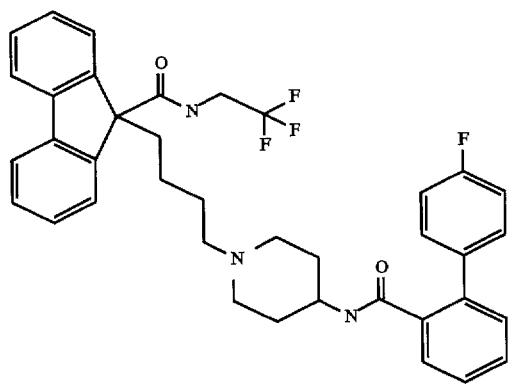
m/z 644 (M+H)
EXAMPLE 100
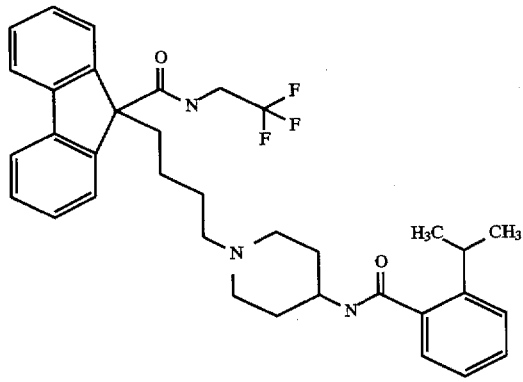
m/z 592 (M+H)
EXAMPLE 101
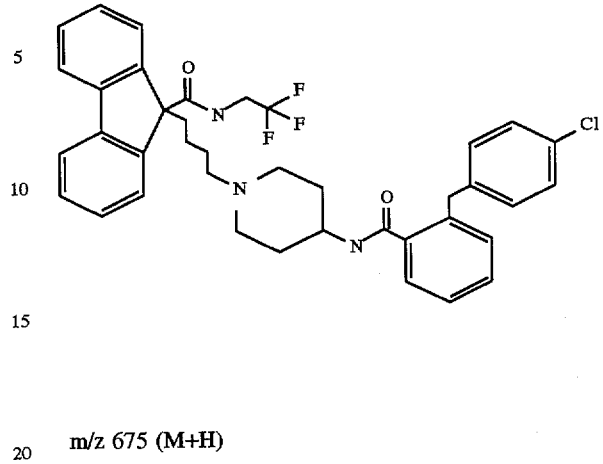
m/z 675 (M+H)
EXAMPLE 102
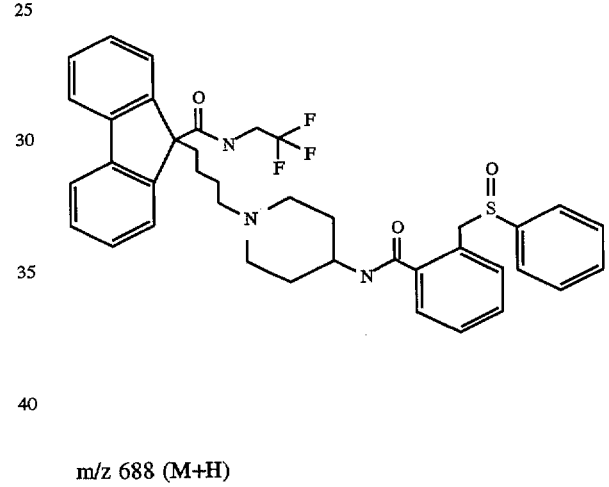
m/z 688 (M+H)
EXAMPLE 103
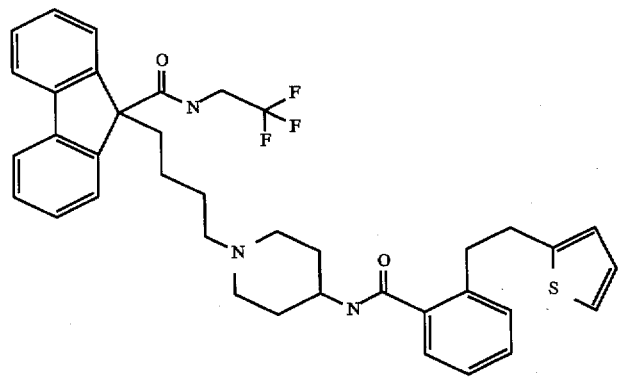

101                    102
m/z 660 (M+H)           EXAMPLE 107
EXAMPLE 104
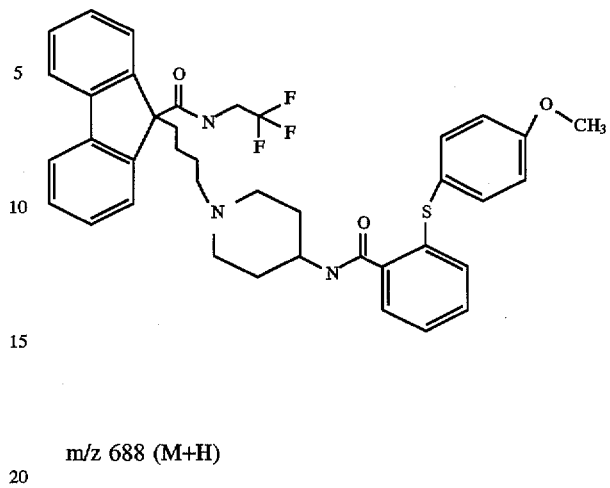
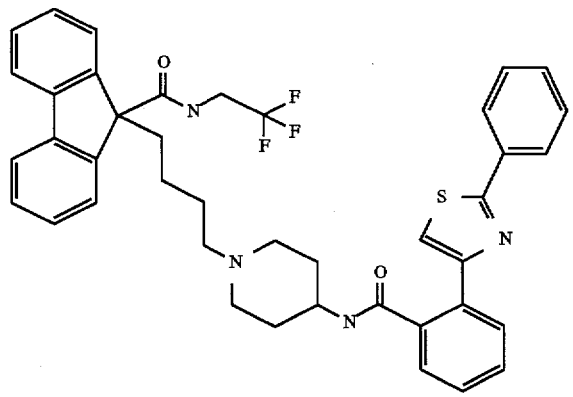
m/z 688 (M+H)
m/z 709 (M+H)
EXAMPLE 105          EXAMPLE 108
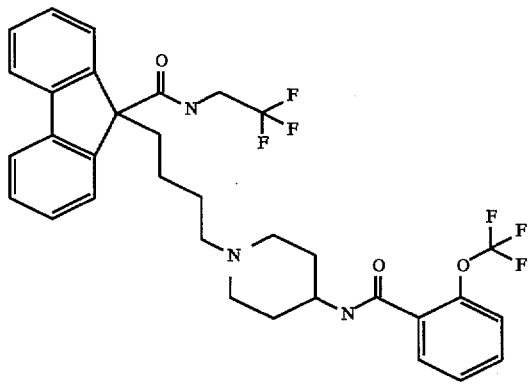 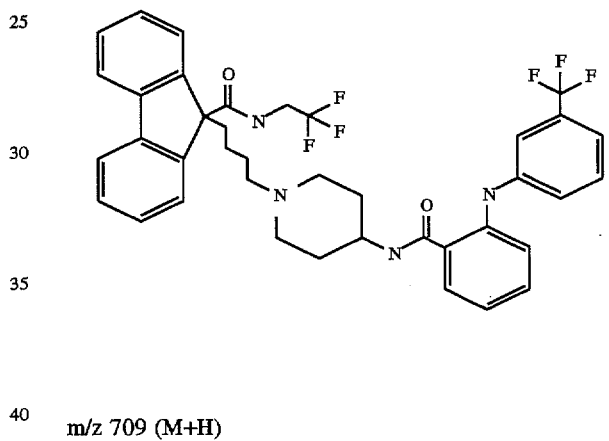
m/z 709 (M+H)
m/z 634 (M+H)
EXAMPLE 106         EXAMPLE 109
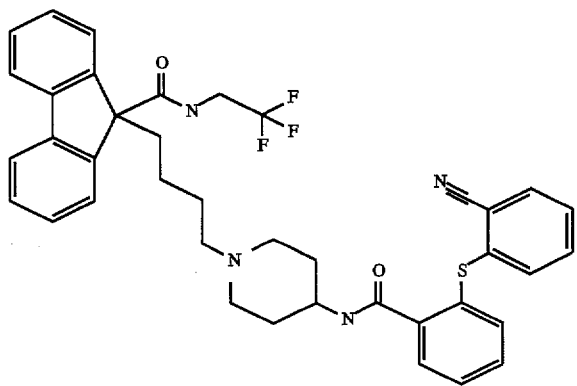 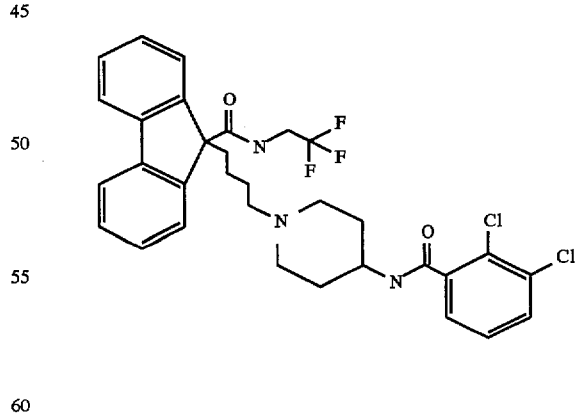
m/z 683 (M+H)          m/z 619 (M+H)

EXAMPLE 110
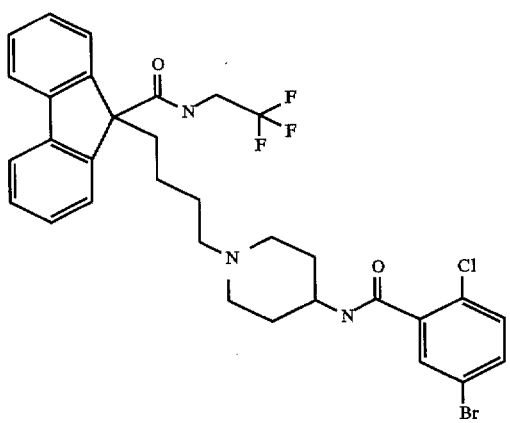
m/z 663 (M+H)
EXAMPLE 111
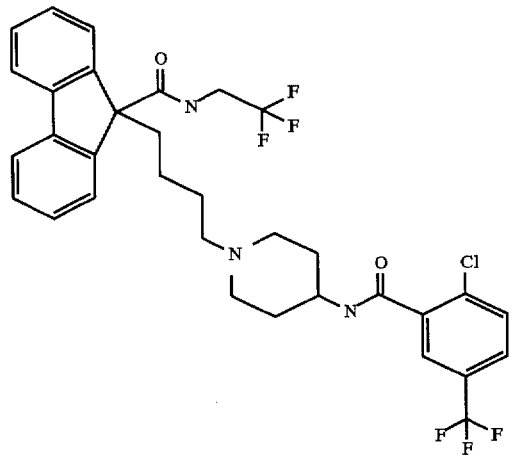
m/z 653 (M+H)
EXAMPLE 112
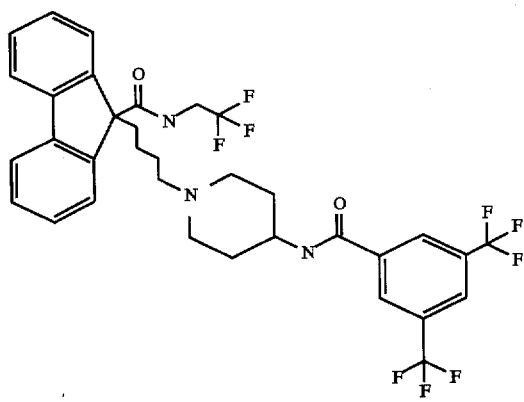
m/z 686 (M+H)
EXAMPLE 113
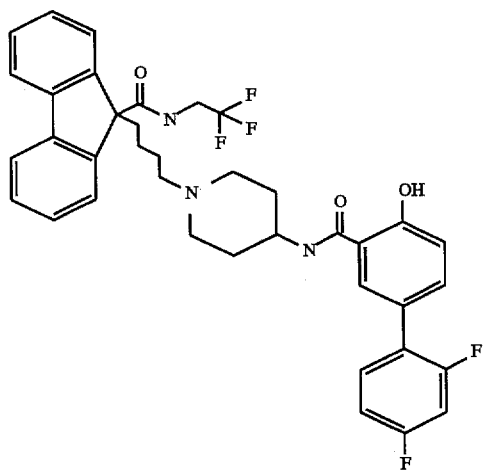
m/z 678 (M+H)
EXAMPLE 114
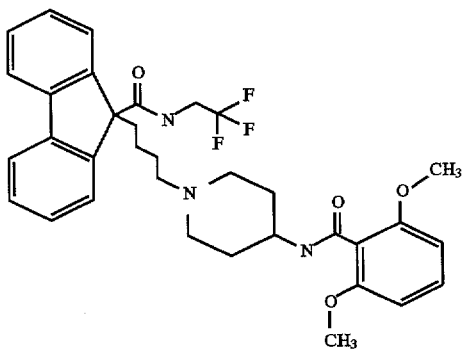
m/z 610 (M+H)
EXAMPLE 115
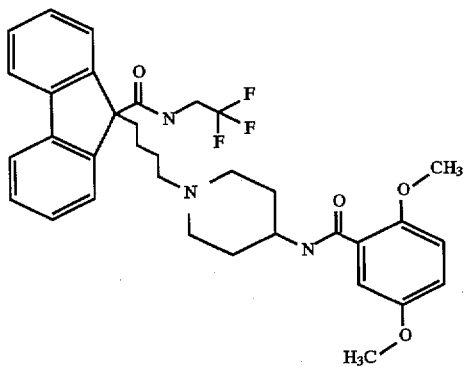
m/z 610 (M+H)

EXAMPLE 116
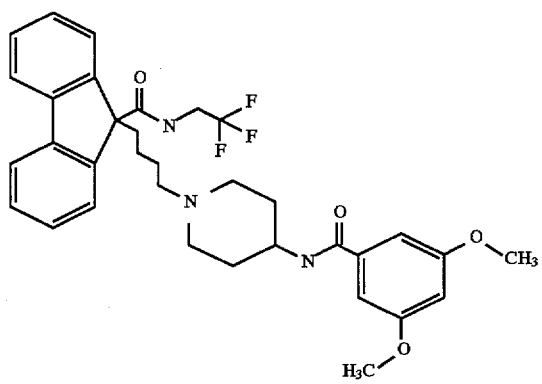
m/z 610 (M+H)
EXAMPLE 117
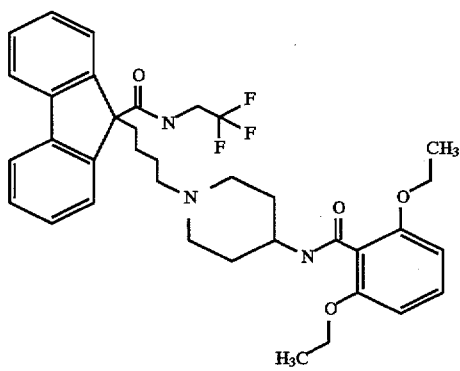
m/z 638 (M+H)
EXAMPLE 118
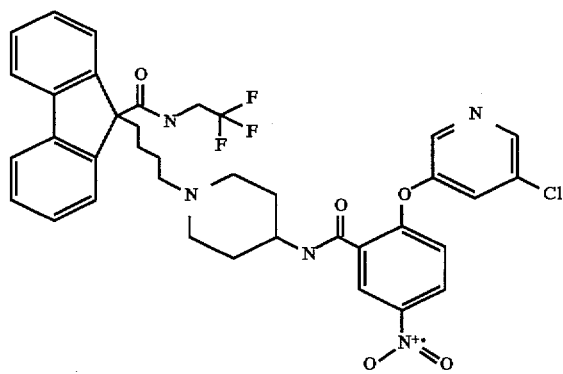
m/z 723 (M+H)
EXAMPLE 119
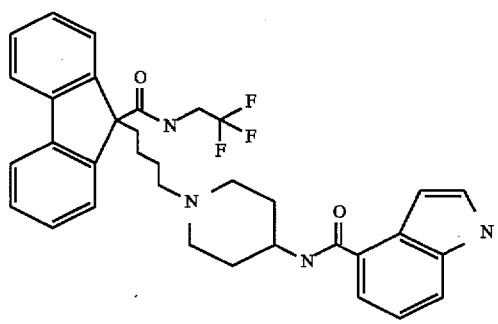
m/z 589 (M+H)
EXAMPLE 120
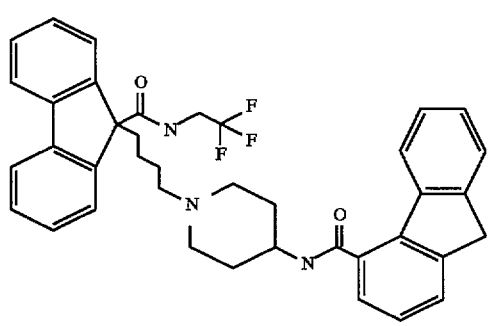
m/z 638 (M+H)
EXAMPLE 121
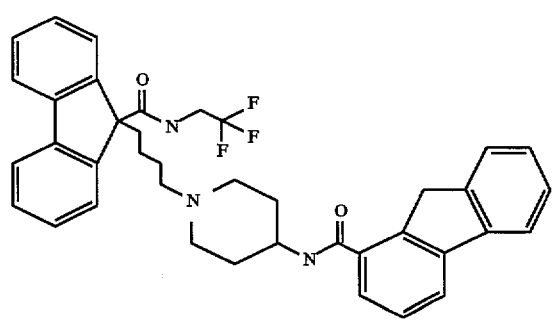
m/z 638 (M+H)

107
EXAMPLE 122
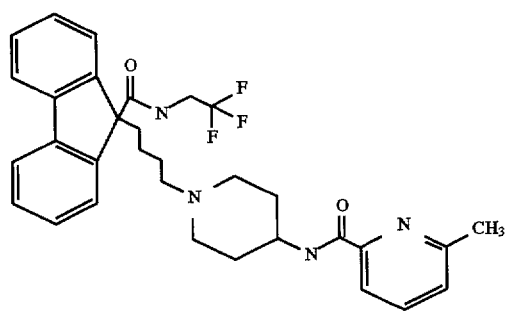
m/z 565 (M+H)
EXAMPLE 123
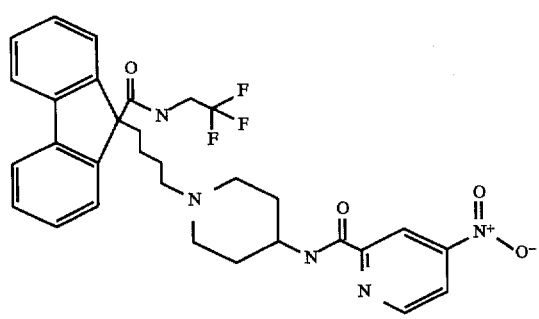
m/z 596 (M+H)
EXAMPLE 124
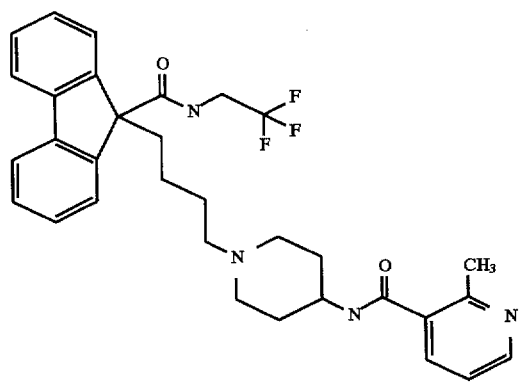
m/z 565 (M+H)
108
EXAMPLE 125
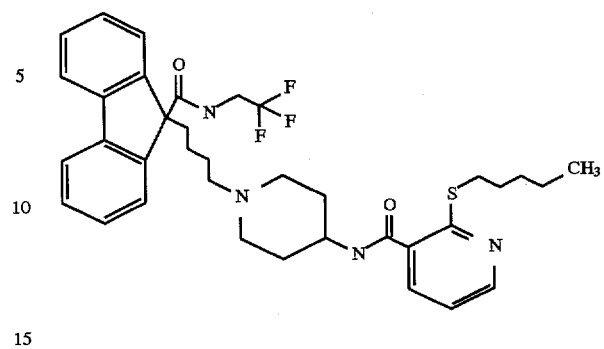
m/z 653 (M+H)
EXAMPLE 126
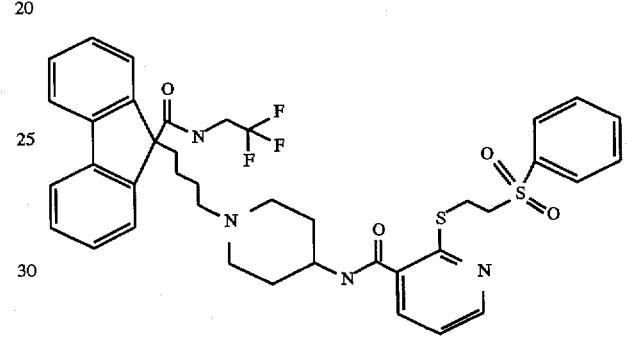
m/z 751 (M+H)
EXAMPLE 127
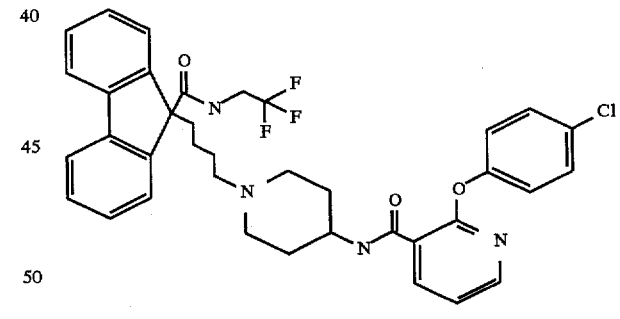
m/z 678 (M+H)

EXAMPLE 128
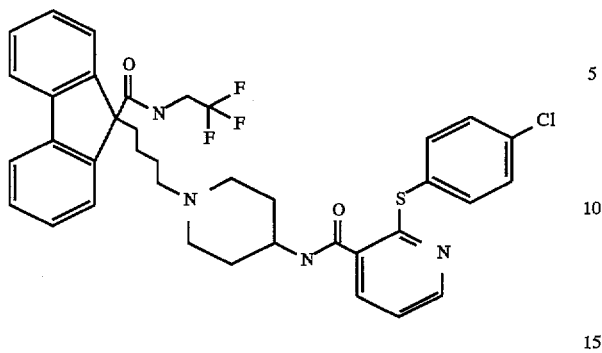
m/z 694 (M+H)
m/z 654 (M+H)
EXAMPLE 129
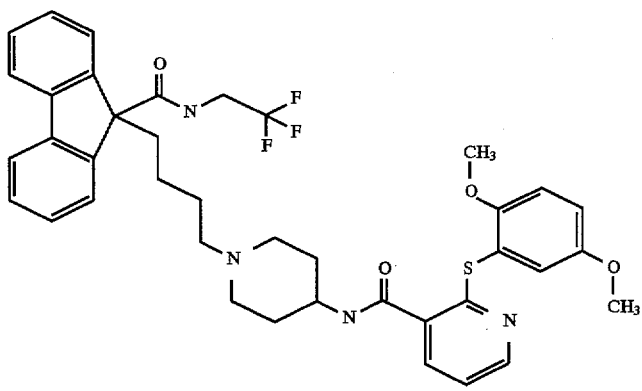
m/z 719 (M+H)
EXAMPLE 130
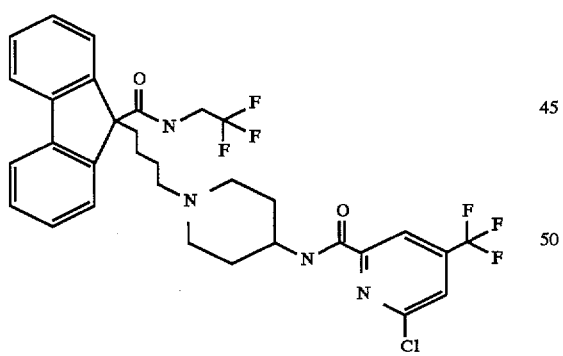

EXAMPLE 131
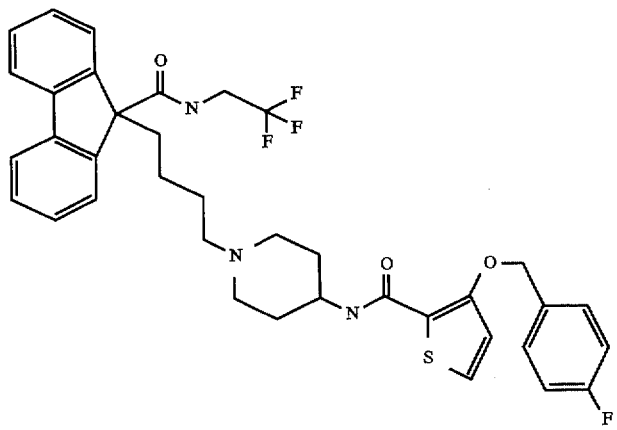
m/z 680 (M+H)
EXAMPLE 132
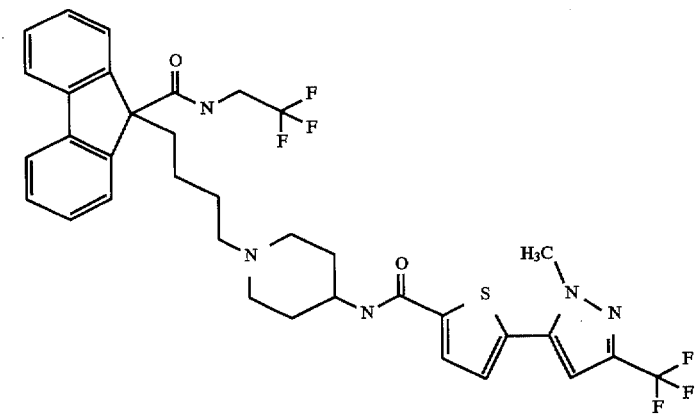
m/z 704 (M+H)
EXAMPLE 133
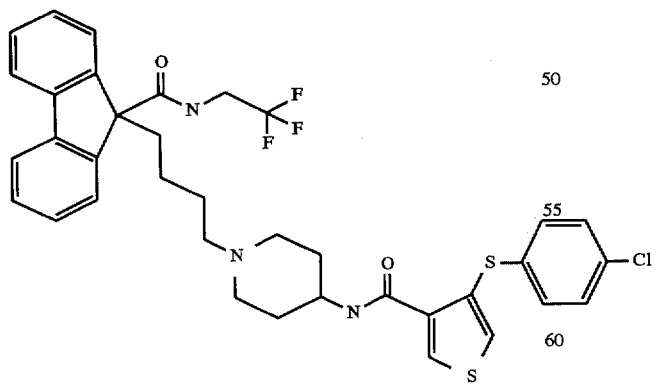
m/z 699 (M+H)

EXAMPLE 134
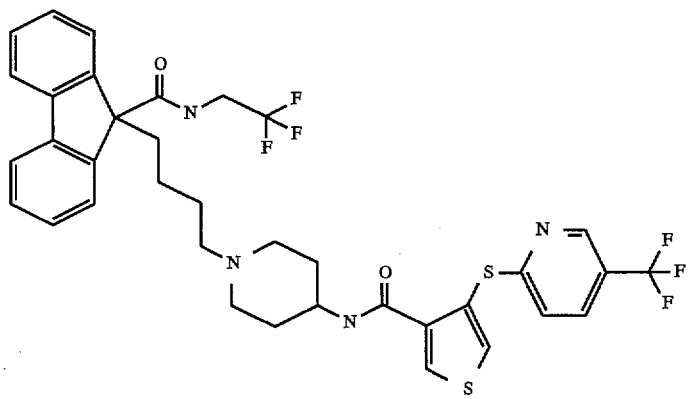
m/z 733 (M+H)
EXAMPLE 135
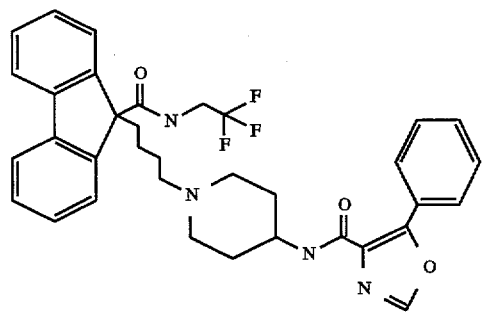
m/z 617 (M+H)
EXAMPLE 136
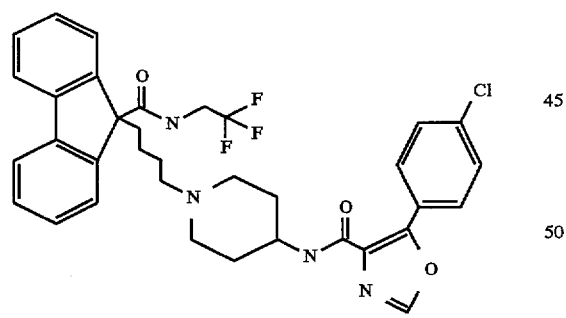
m/z 652 (M+H)
EXAMPLE 137
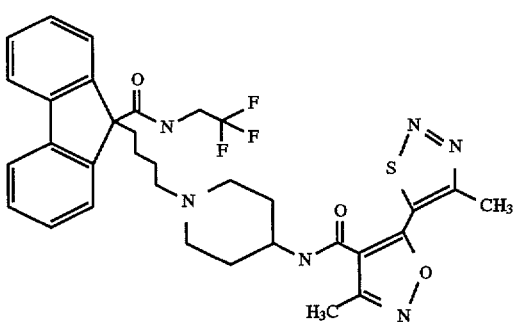
m/z 653 (M+H)

EXAMPLE 138
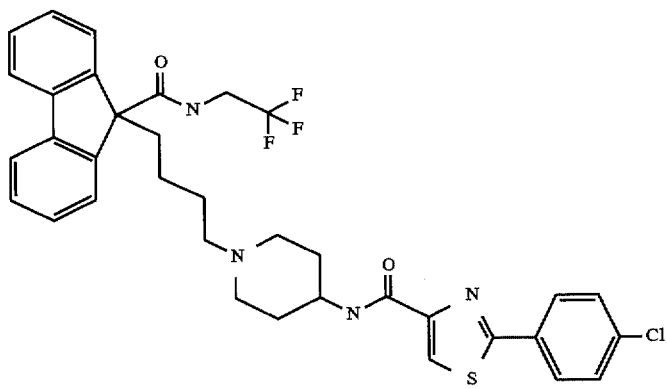
m/z 668 (M+H)
EXAMPLE 139
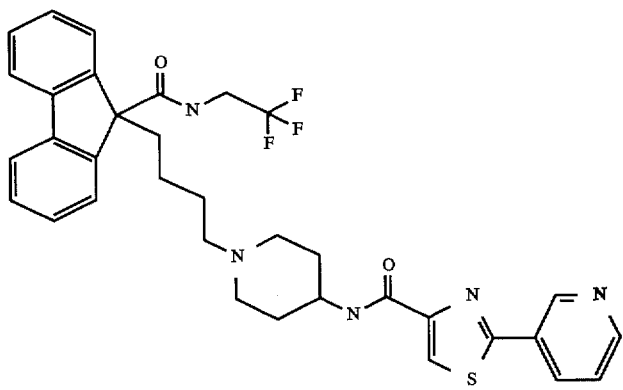
m/z 634 (M+H)
EXAMPLE 140
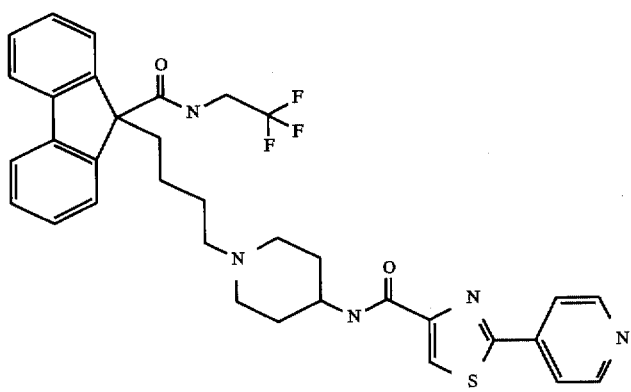
m/z 634 (M+H)

EXAMPLE 141
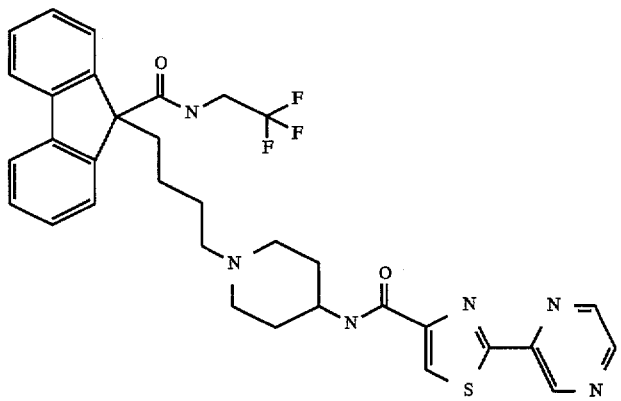
m/z 635 (M+H)
EXAMPLE 142
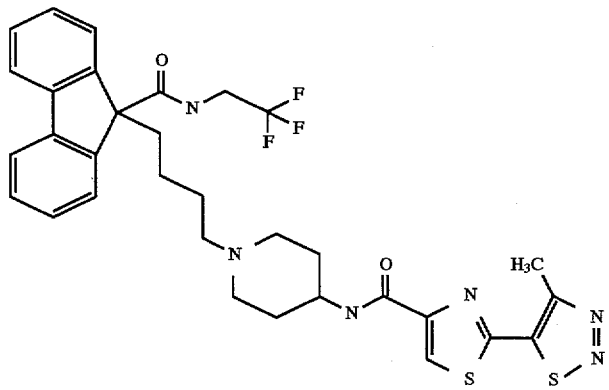
m/z 655 (M+H)
EXAMPLE 143
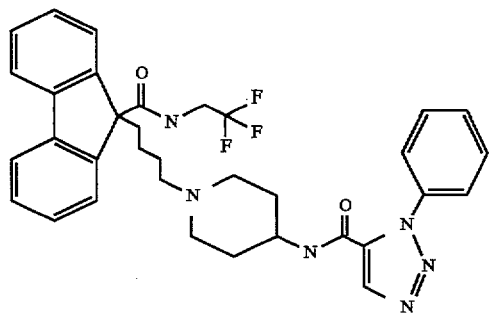
m/z 617 (M+H)
EXAMPLE 144
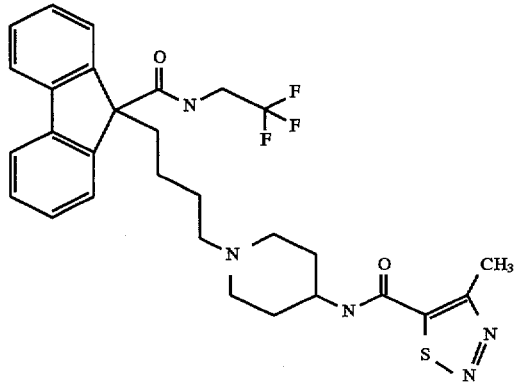
m/z 572 (M+H)

119
EXAMPLE 145
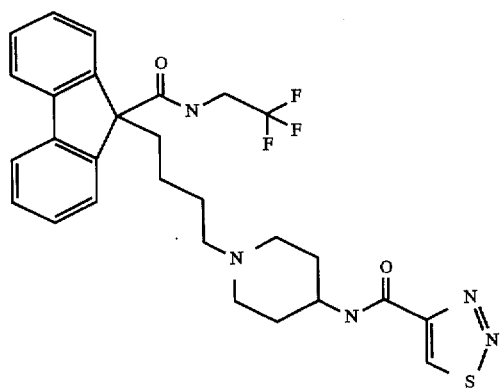
m/z 558 (M+H)
EXAMPLE 146
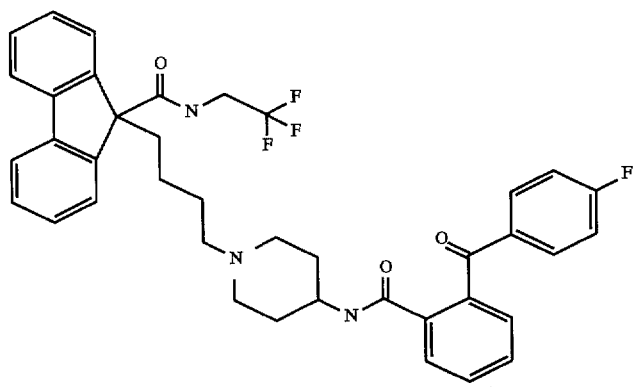
m/z 672 (M+H)
EXAMPLE 147
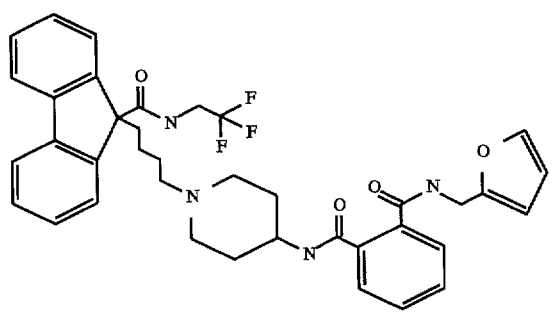
m/z 673 (M+H)
120
EXAMPLE 148
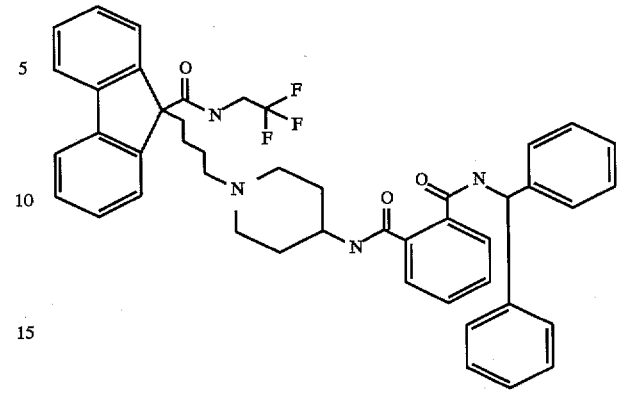
m/z 759 (M+H)
EXAMPLE 149
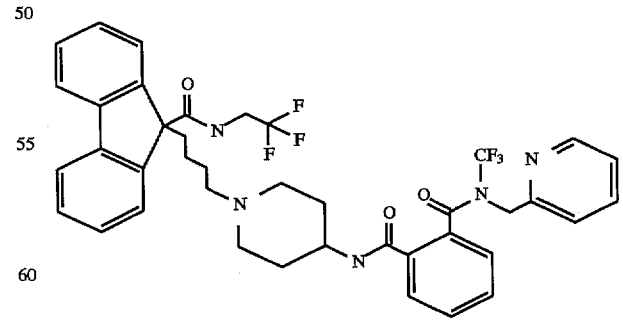
m/z 698 (M+H)

121
EXAMPLE 150
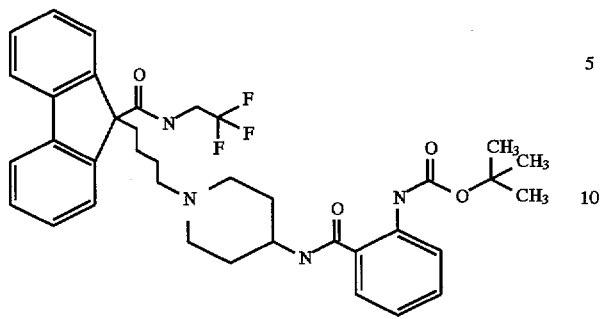
m/z 665 (M+H)
EXAMPLE 151
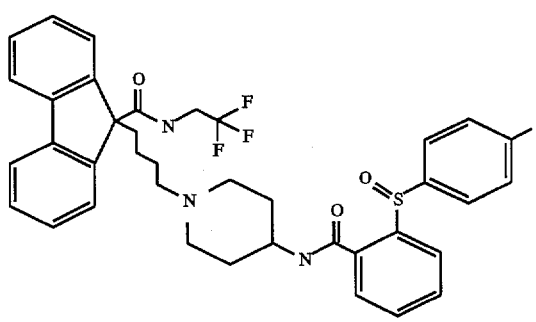
m/z 709 (M+H)
EXAMPLE 152
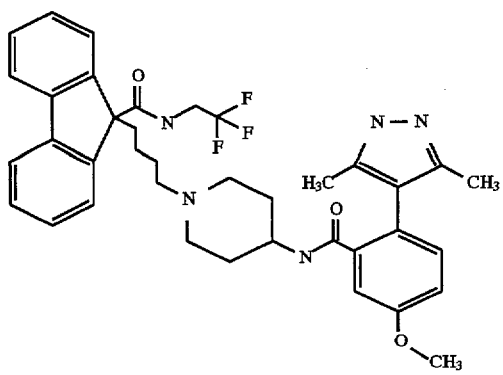
m/z 674 (M+H)
122
EXAMPLE 153
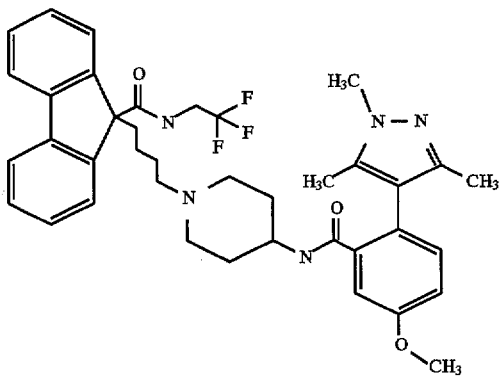
m/z 688 (M+H)
EXAMPLE 154
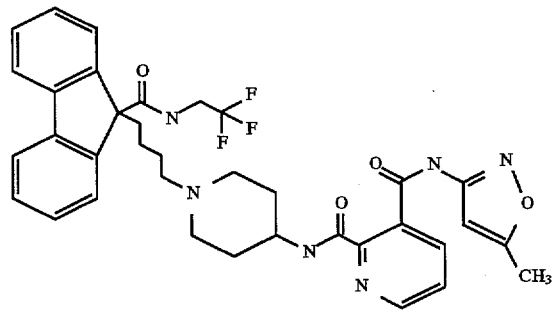
m/z 675 (M+H)
EXAMPLE 155
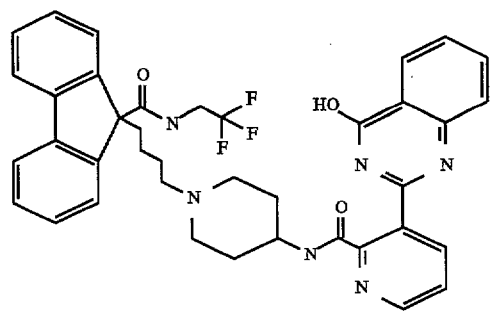
m/z 695 (M+H)

123

EXAMPLE 156

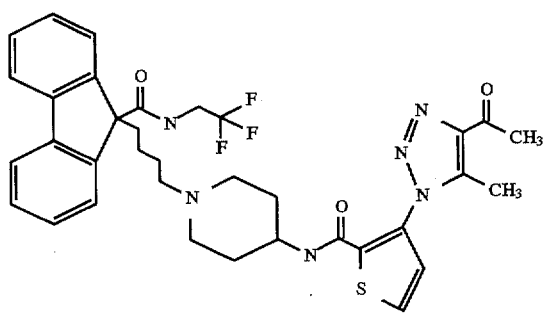

m/z 679 (M+H)

EXAMPLE 157

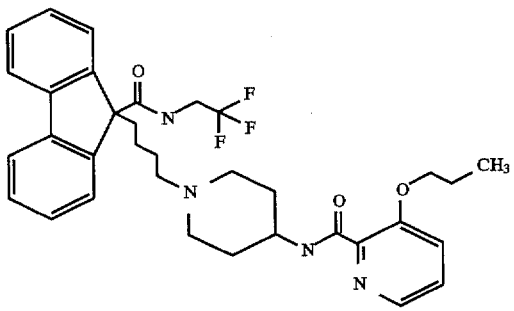

m/z 609 (M+H)

EXAMPLE 158

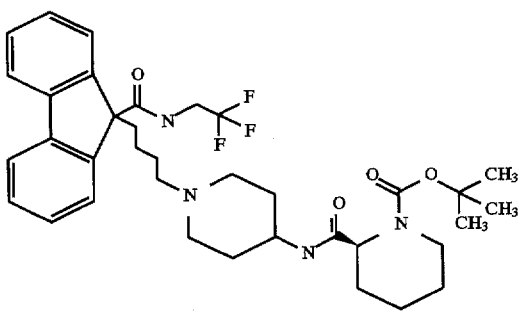

m/z 657 (M+H)

124

EXAMPLE 159

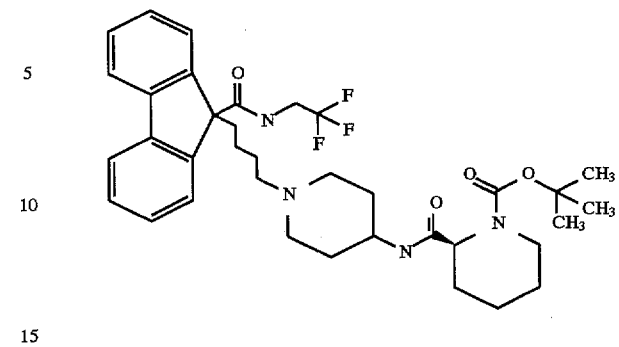

m/z 657 (M+H)

What is claimed is:

1. A compound having the structure

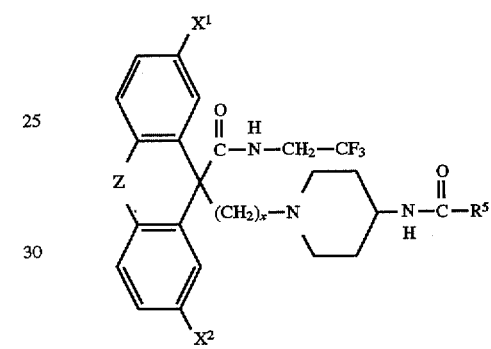

including the piperidine N-oxide thereof or a pharmaceutically acceptable salt thereof, wherein Z is a bond or S;

$X^1$ and $X^2$ are independently selected from H or halo;

x is an integer from 2 to 6, $(CH_2)_x$ is optionally substituted with 1, 2 or 3 substituents which are the same or different and are alkyl or halo;

$R^5$ is heteroaryl, aryl, heterocycloalkyl or cycloalkyl, each $R^5$ group being optionally substituted with 1, 2, 3 or 4 substituents which may be the same or different, wherein one substituents is optionally attached to a ring carbon in the position adjacent to the carbon linked to

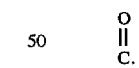

2. The compound as defined in claim 1 wherein Z is a bond.

3. The compound as defined in claim 1 which is a piperidine N-oxide.

4. The compound as defined in claim 1 wherein each of $X^1$ and $X^2$ is H.

5. The compound as defined in claim 1 wherein $(CH_2)_x$ is substituted with 1, 2 or 3 substituents which are the same or different and are alkyl or halo.

6. The compound as defined in claim 5 wherein the halo substituent is F.

7. The compound as defined in claim 1 wherein the substituent on $R^5$ is adjacent to the carbon attached to the

group.

8. The compound as defined in claim 1 wherein $R^5$ is substituted with 1, 2, 3 or 4 substituents which may be the same or different and are bicyclic heteroaryl, aryl, alkylamino, alkyl(aryl)amino, heteroarylamino, arylamino, or acyl.

9. The compound as defined in claim 1 wherein $R^5$ is independently substituted with 1, 2, 3 or 4 of the following I, Cl, F, $CF_3$,

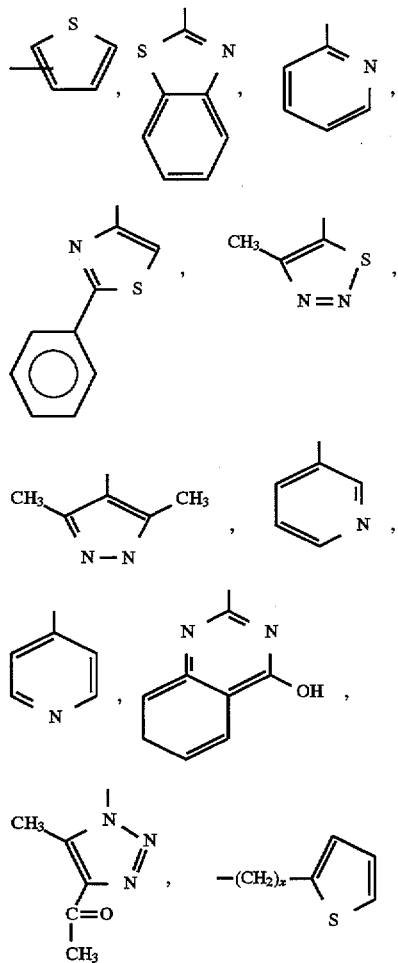

where x is 1 to 5

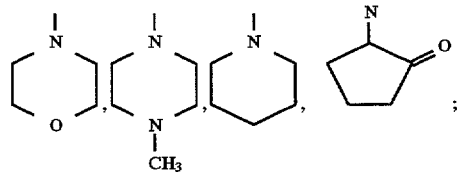

alkyl, phenyl, phenyl substituted with halo, alkyl, $CF_3O$, alkoxy,

$CF_3$, or phenyl;

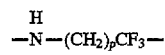

where p is 1 to 5, $-N(CH_3)C_6H_5$; $-S-(CH_2)_pCF_3$ where p is 1 to 5,

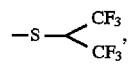

—S—alkyl,

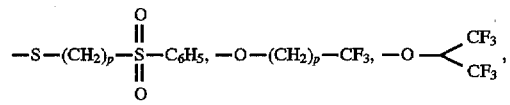

$OCH_3$; cyclohexyl,

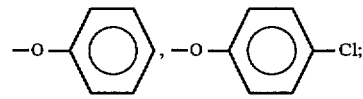

amino;

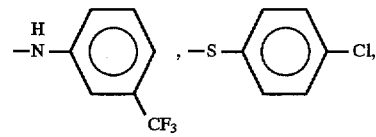

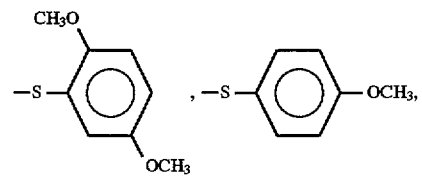

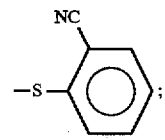

alkanoyl, alkoxycarbonyl, aroyl, heteroarylaminocarbonyl, arylalkyloxycarbonyl, $-CH_2-S-C_6H_5$,

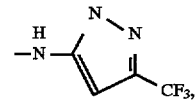

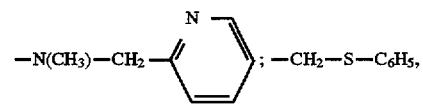

-continued

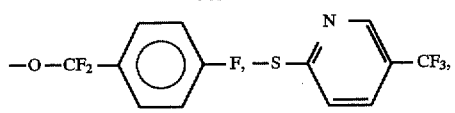, 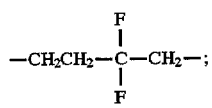

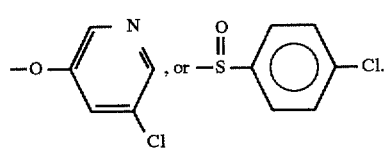

Z is a bond;
$X^1$ and $X^2$ are H;
$R^5$ is aryl, which is substituted with trifluoromethylphenyl, heteroaryl, halo and/or aryl or
$R^5$ is heteroaryl
wherein the $R^5$ includes a substituent attached to a carbon adjacent to the carbon linked to $$\overset{O}{\underset{}{\|}}\\ C.$$

10. The compound as defined in claim 9 wherein $(CH_2)_x$ is $(CH_2)_4$ or

11. The compound as defined in claim 1 which is

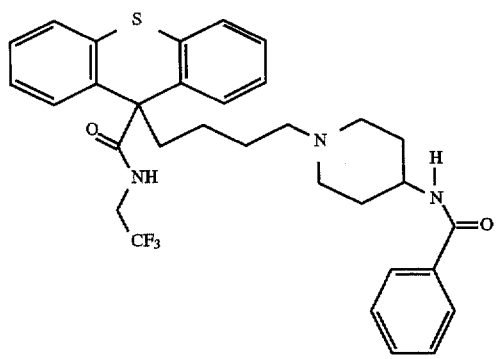

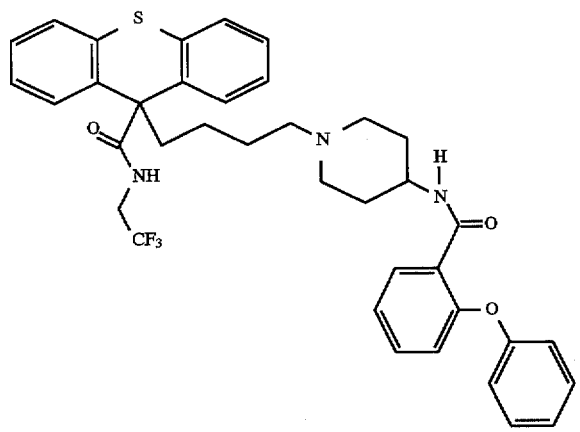

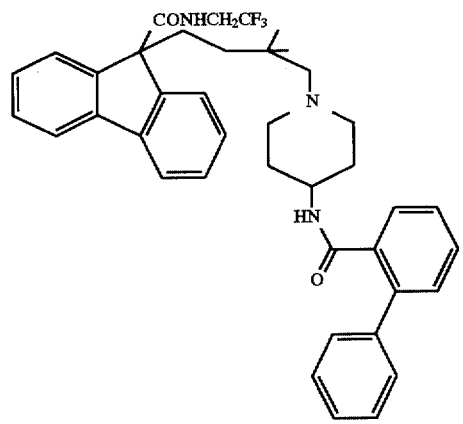

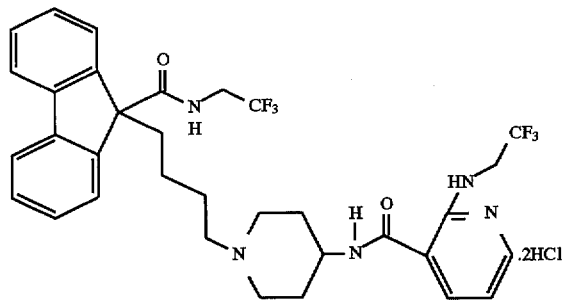

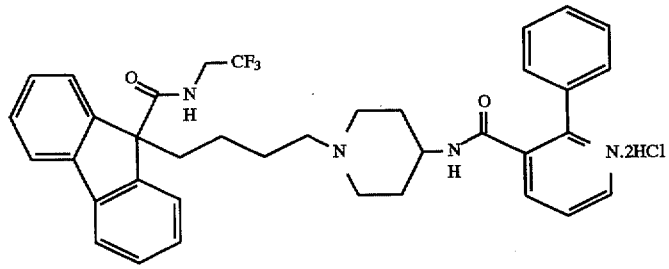

129 130
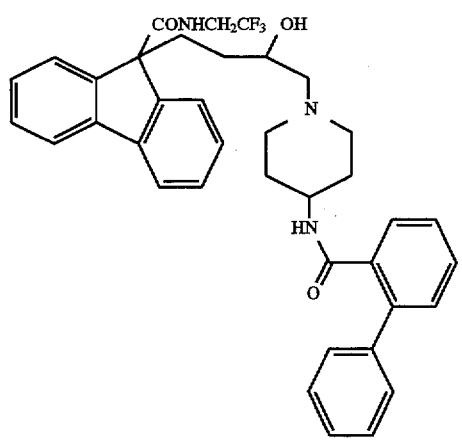
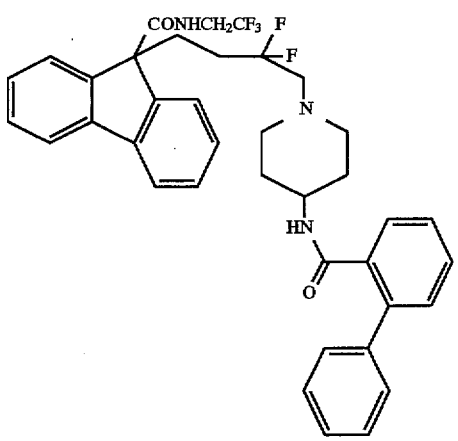
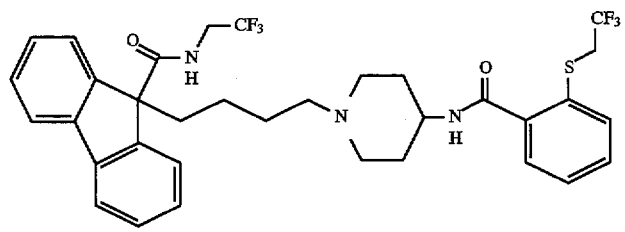
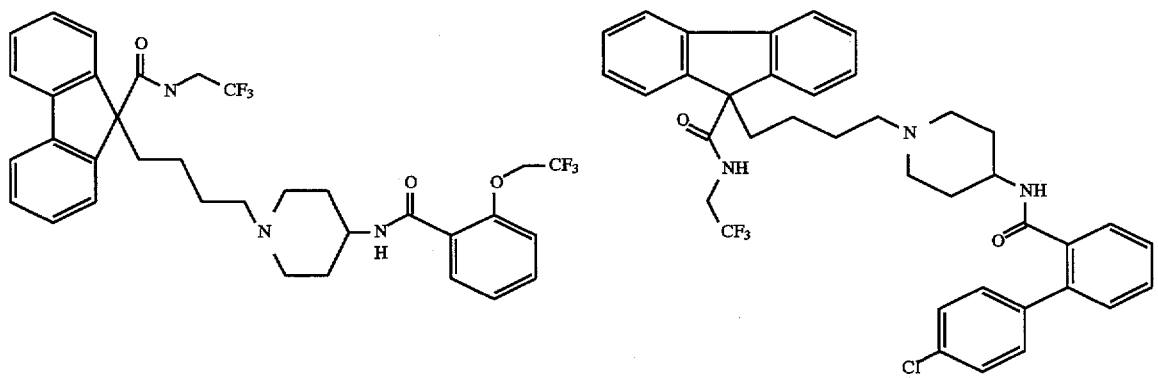
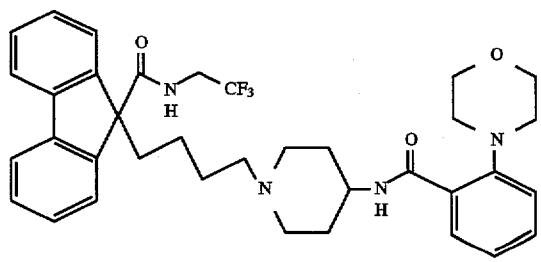
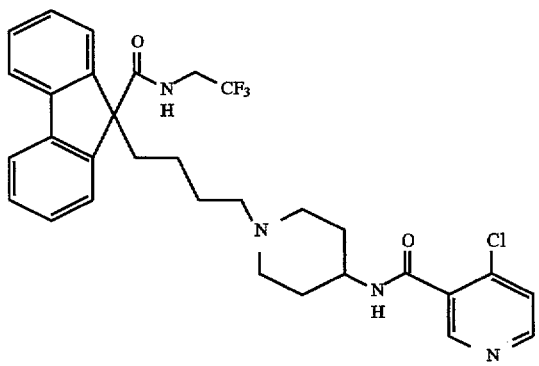

131 132
-continued
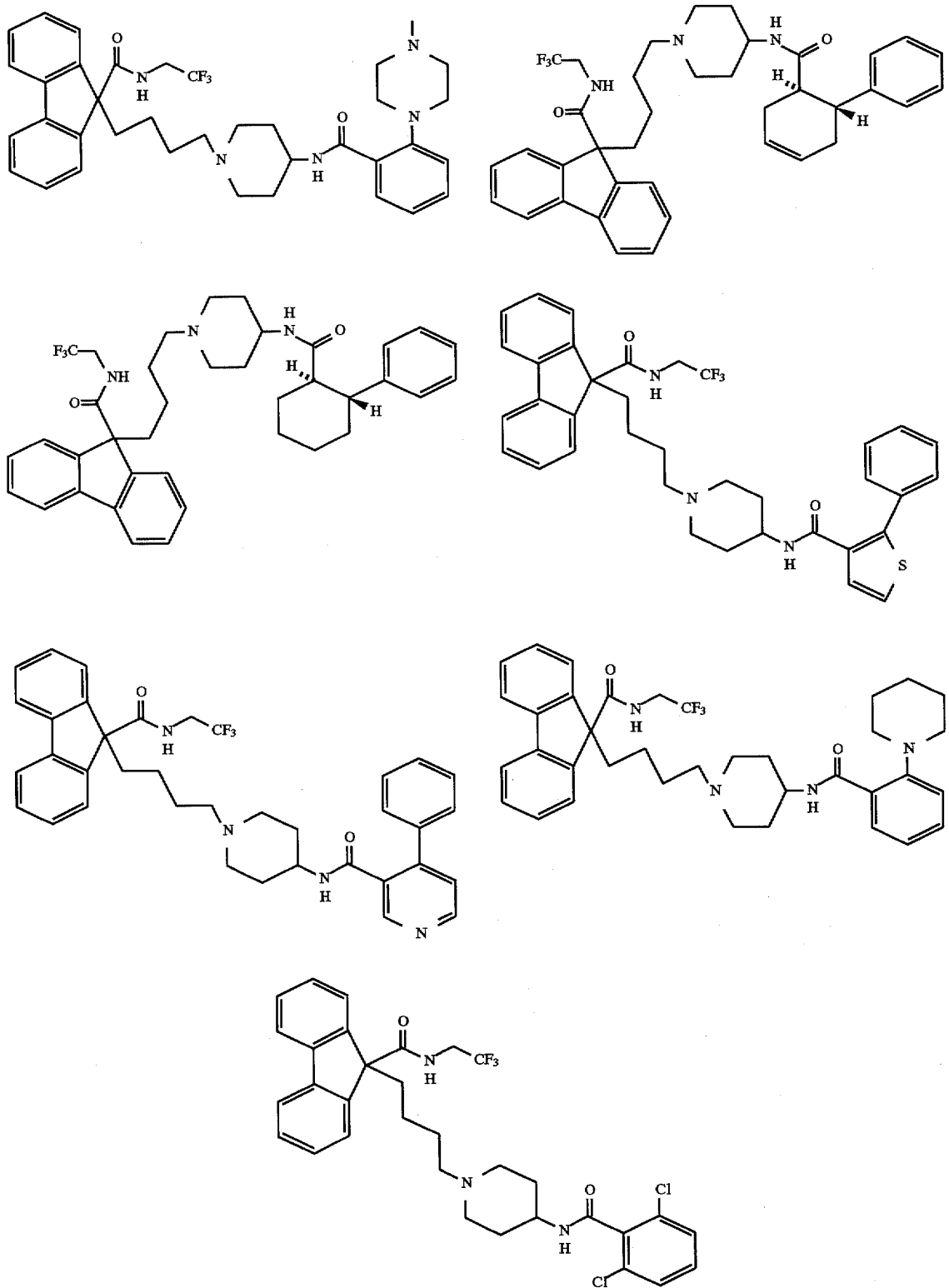

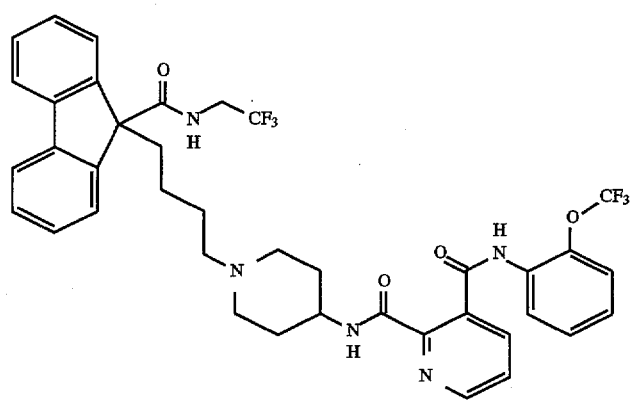
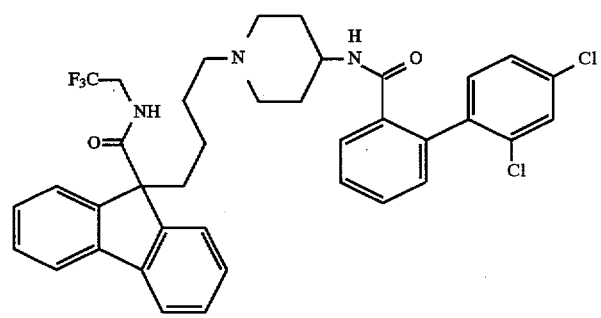
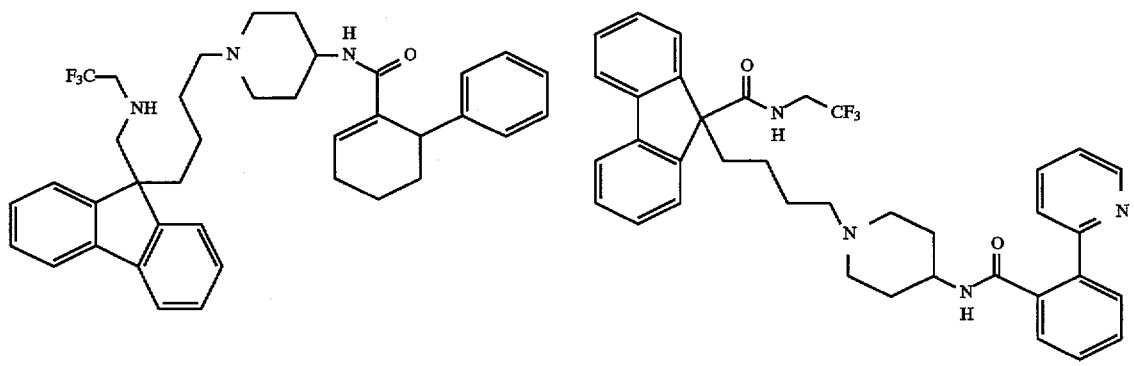
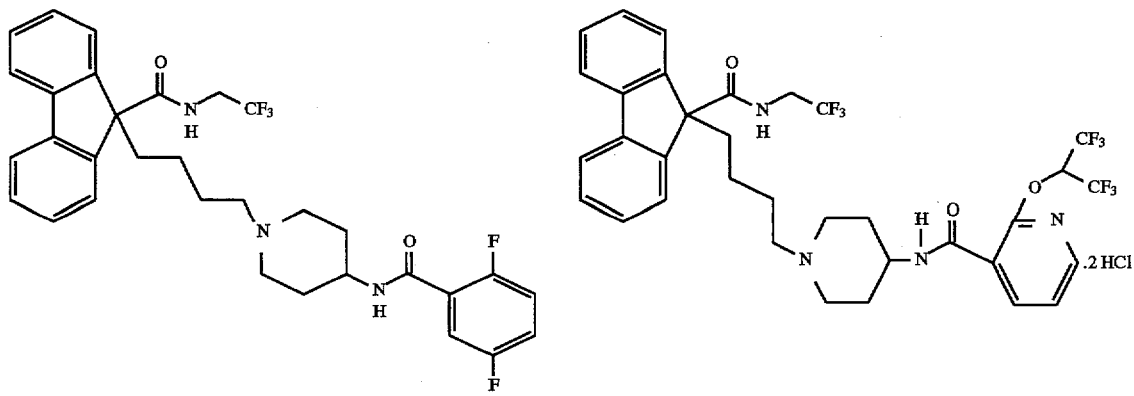

-continued
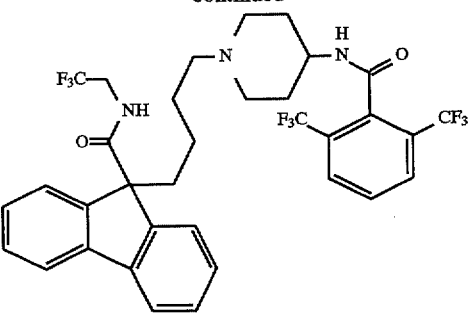
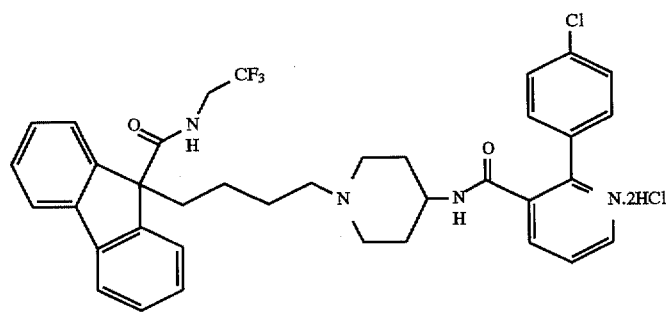
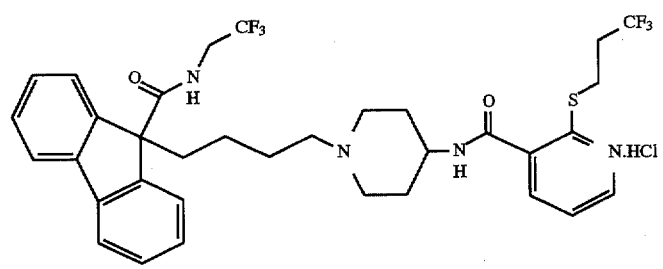
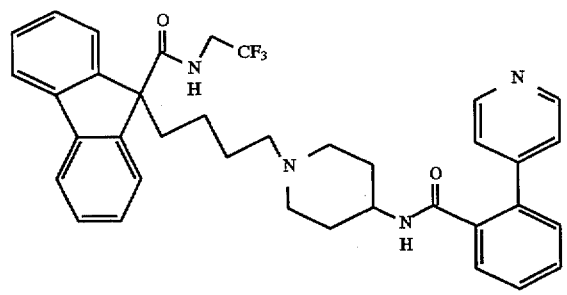
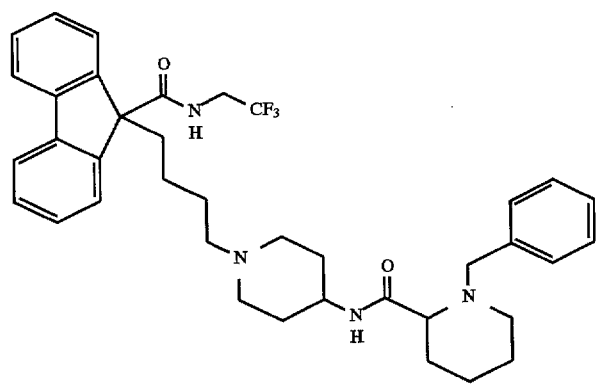

-continued
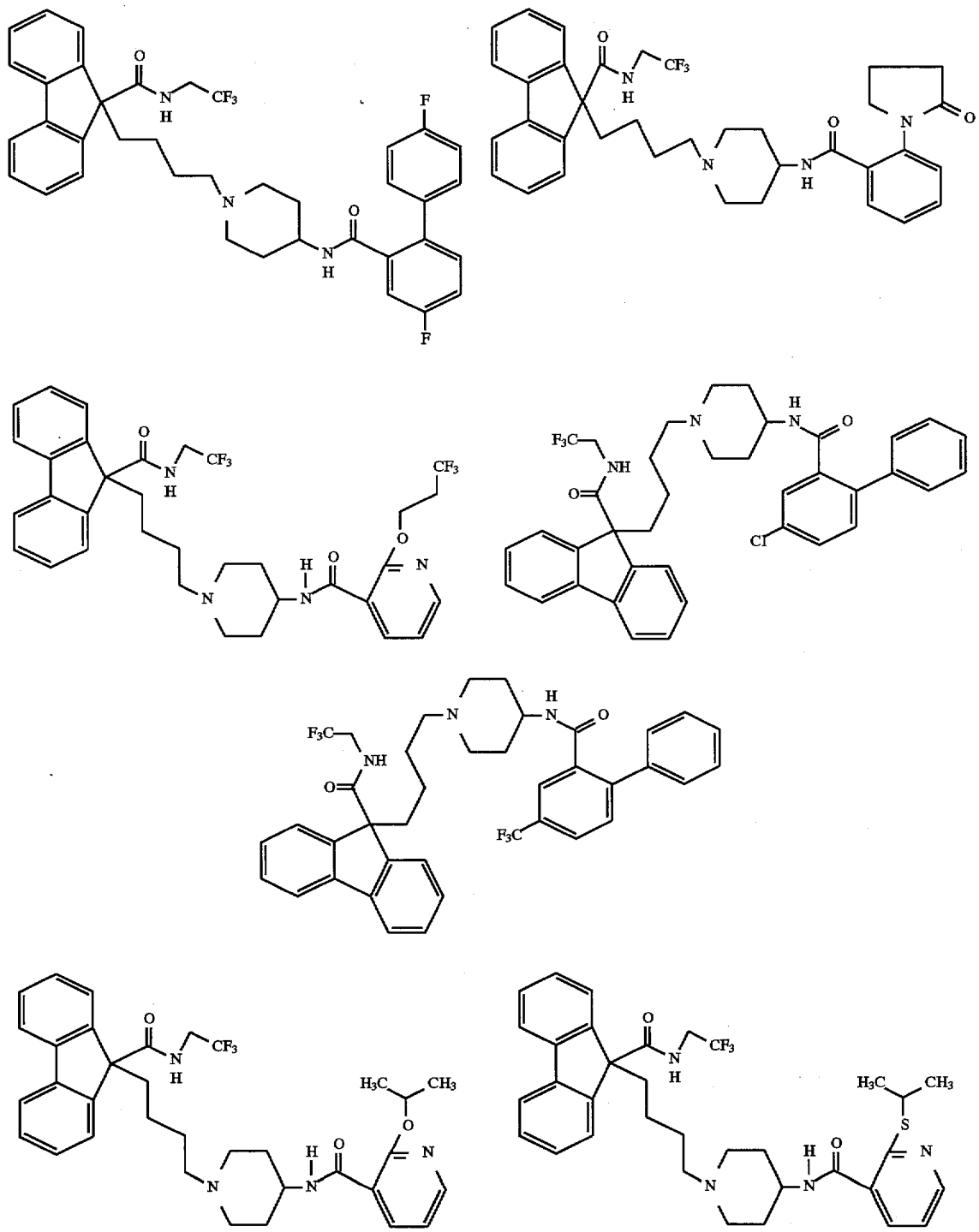

139 140
-continued
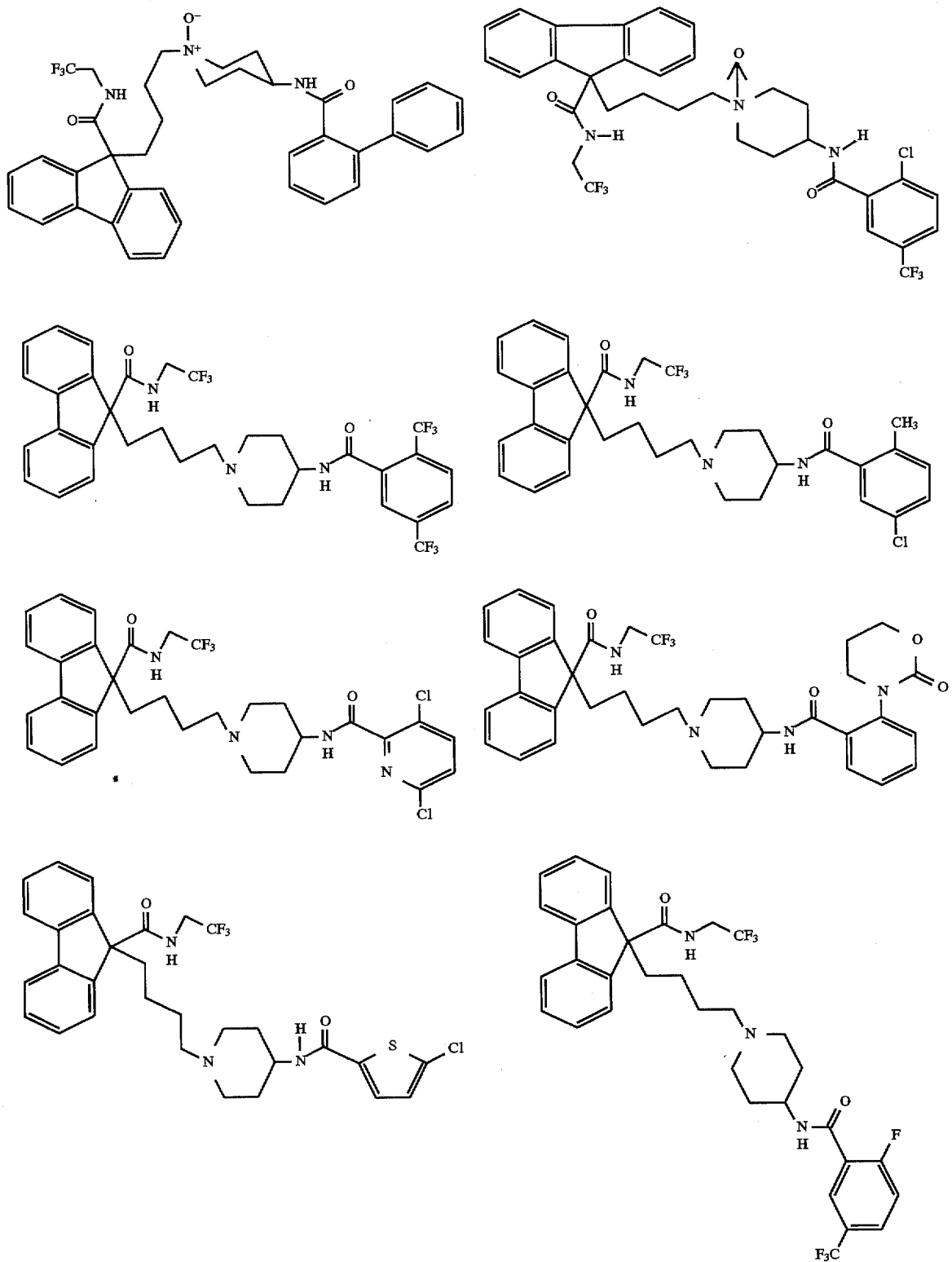

-continued
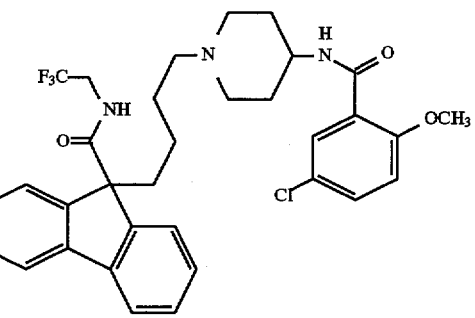
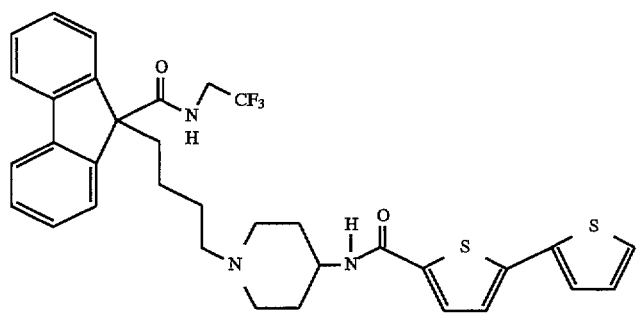
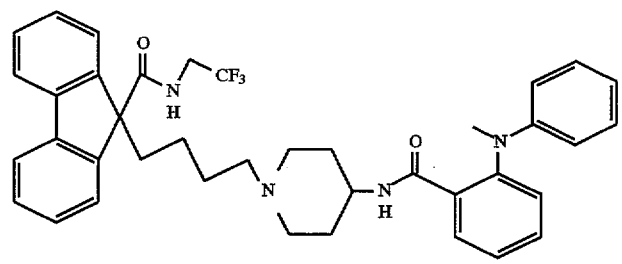
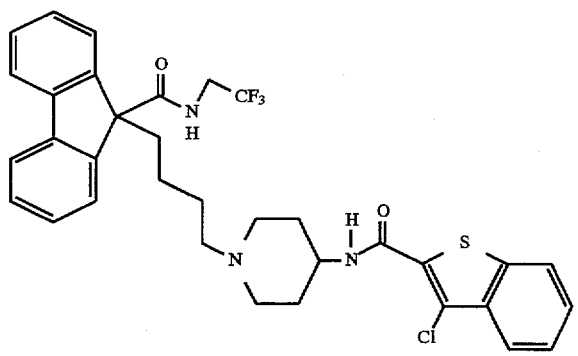
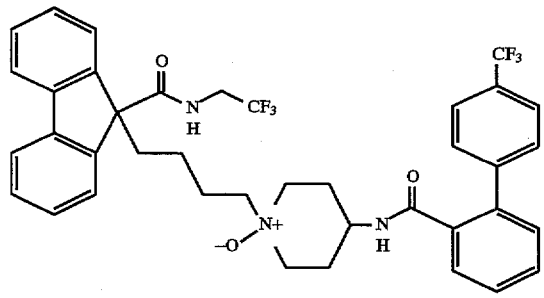

-continued
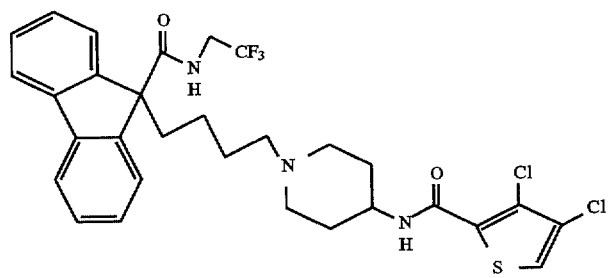
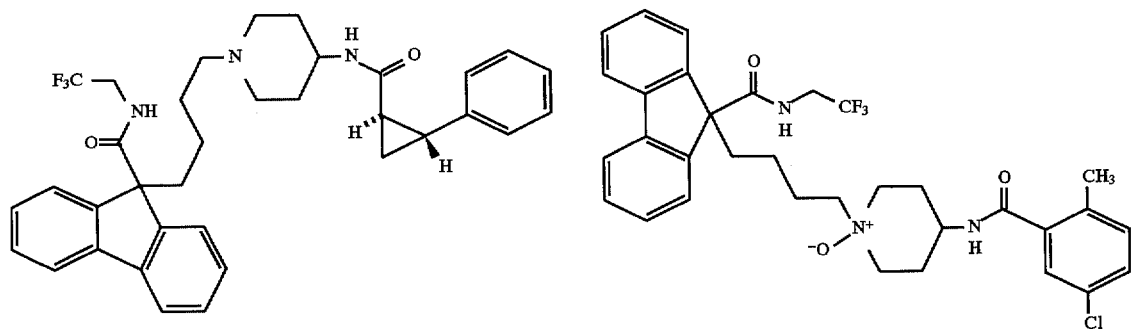
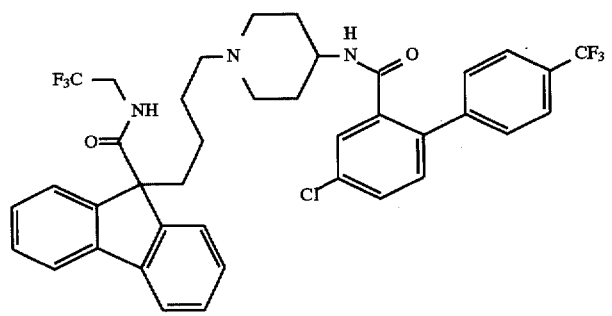
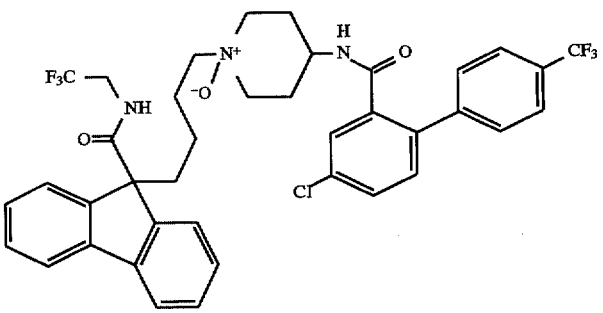
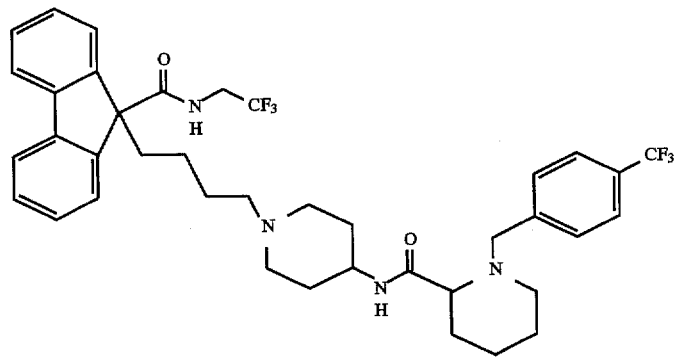

-continued
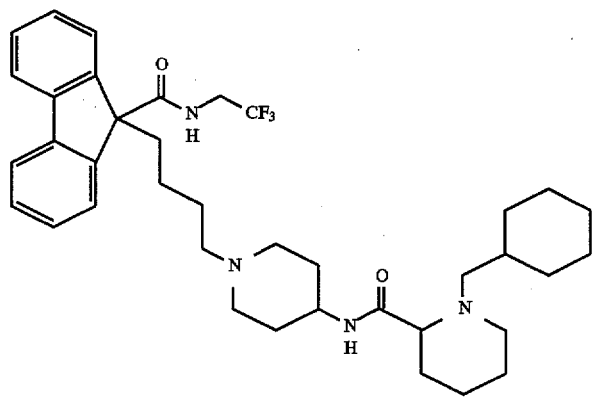
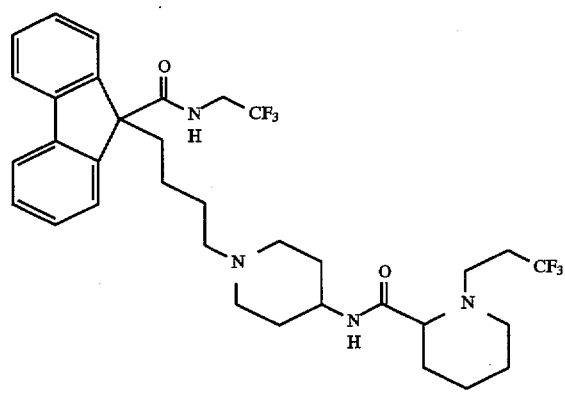
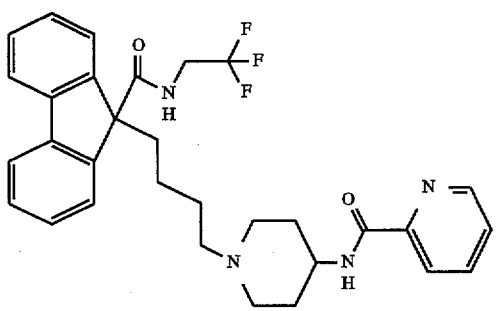
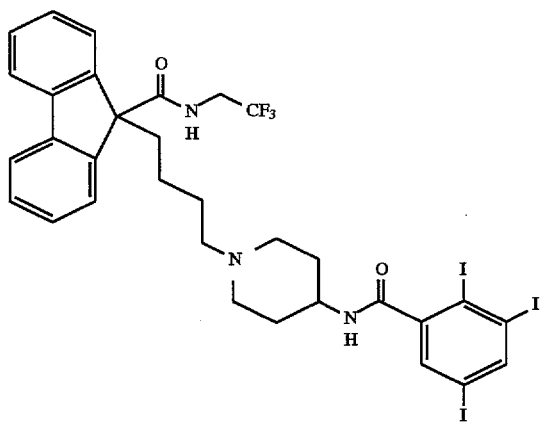
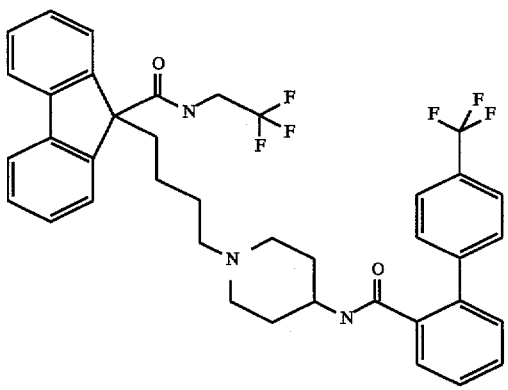
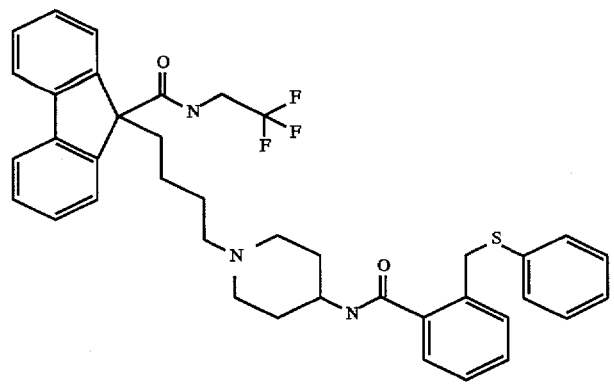

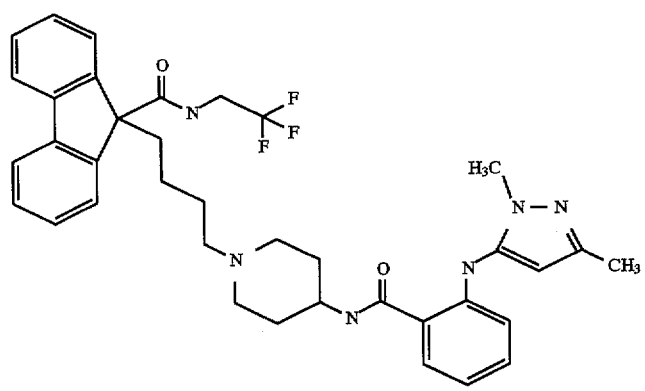
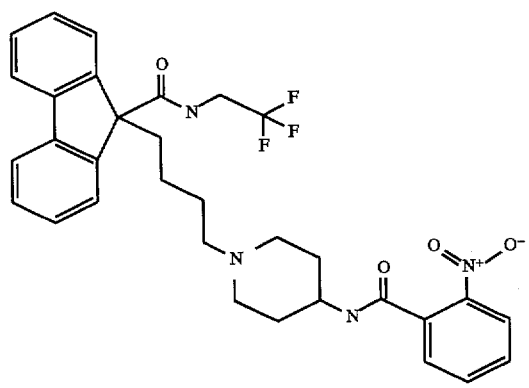
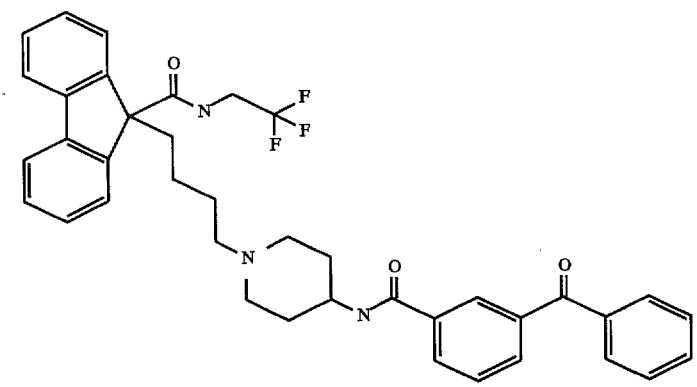
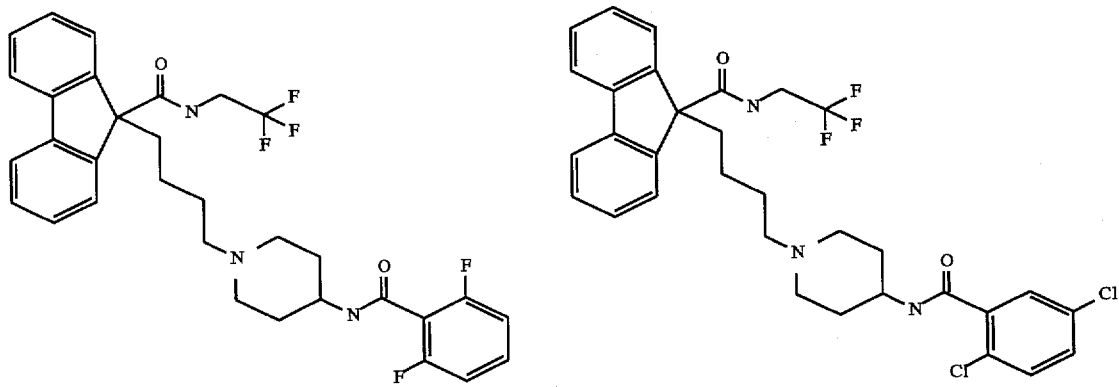

-continued
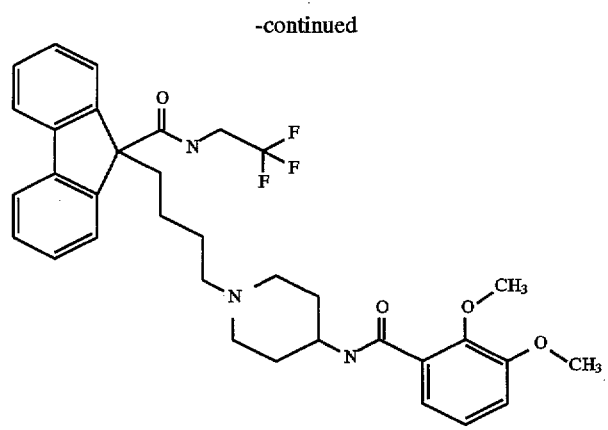
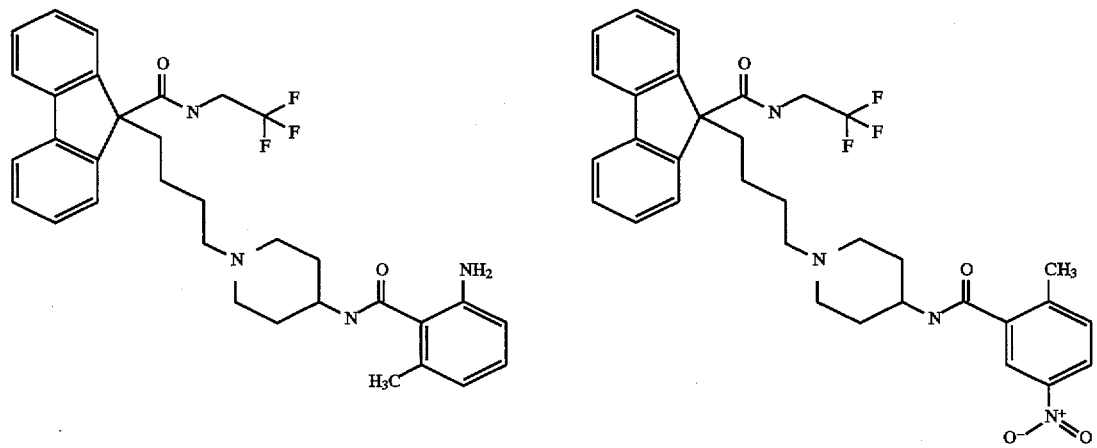
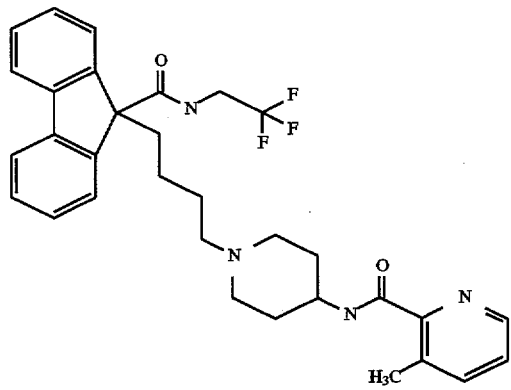
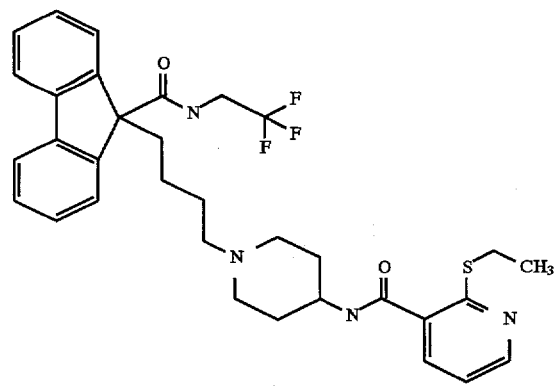

-continued
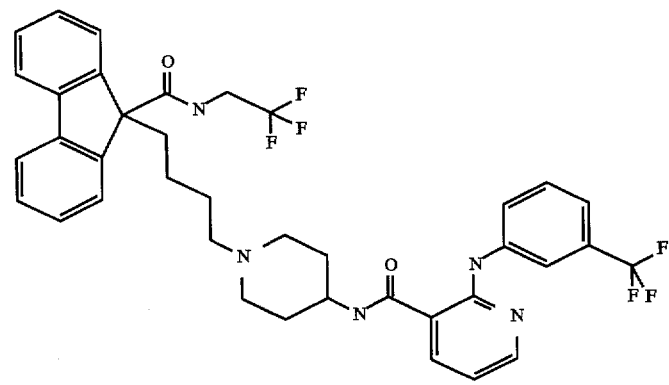
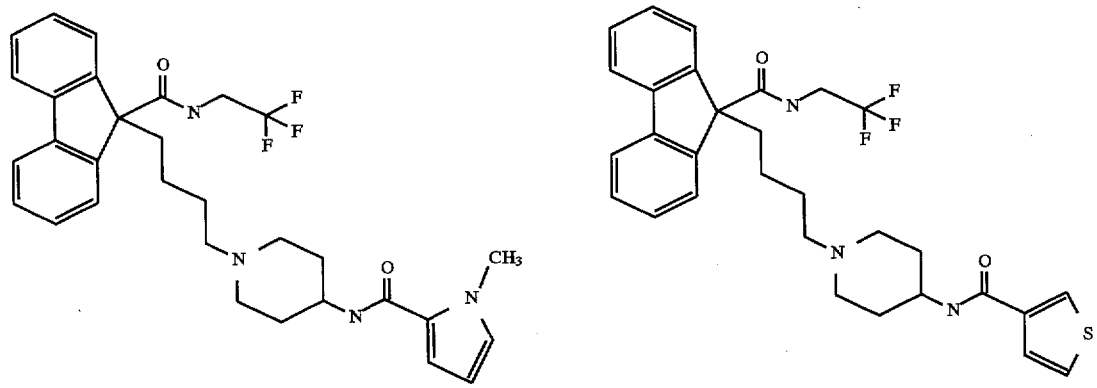
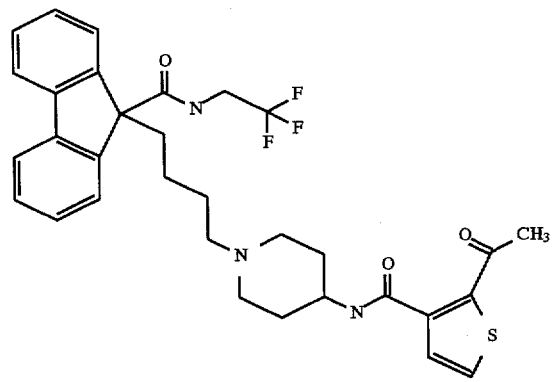
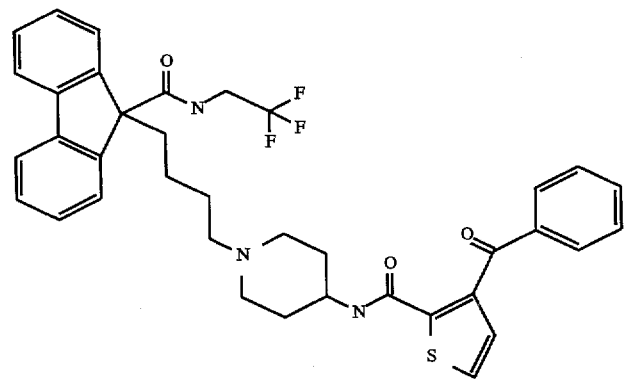

-continued
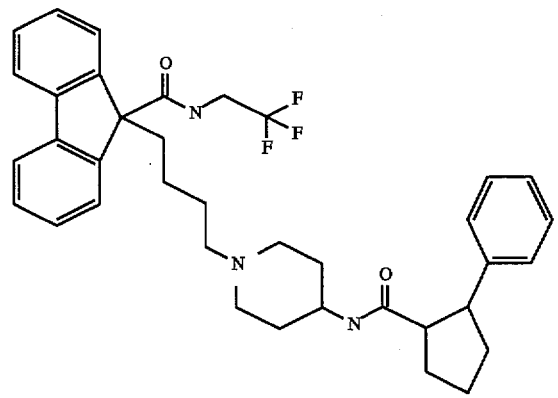
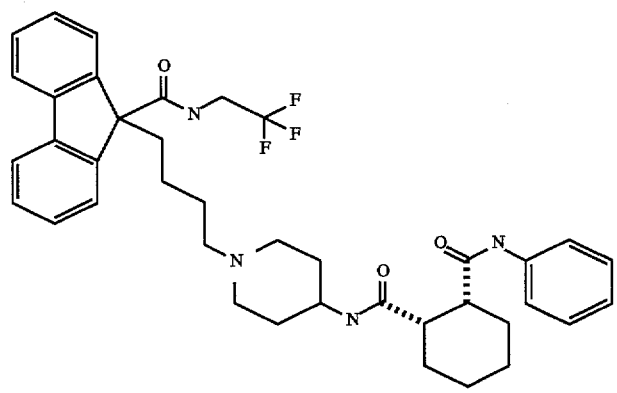
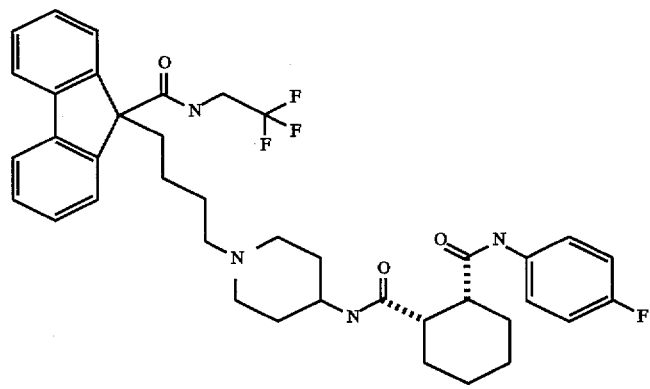
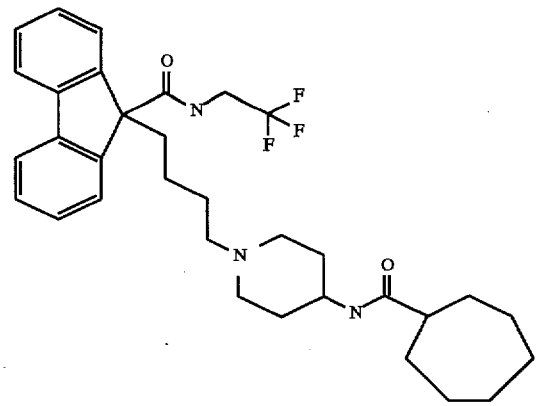

-continued
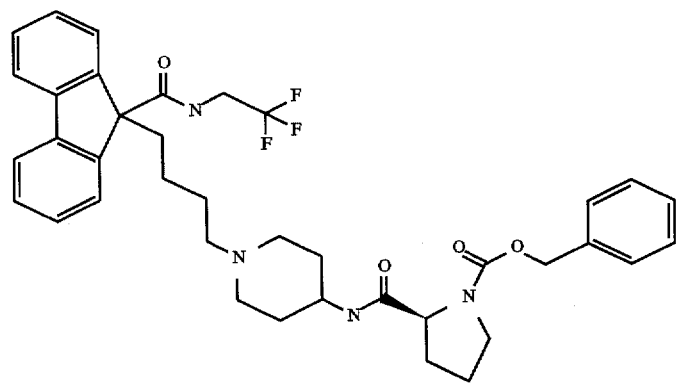
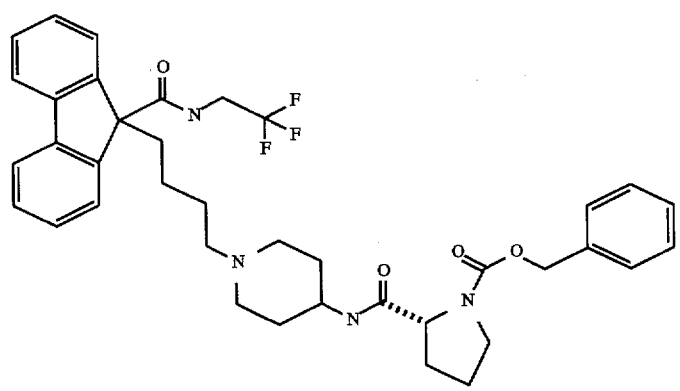
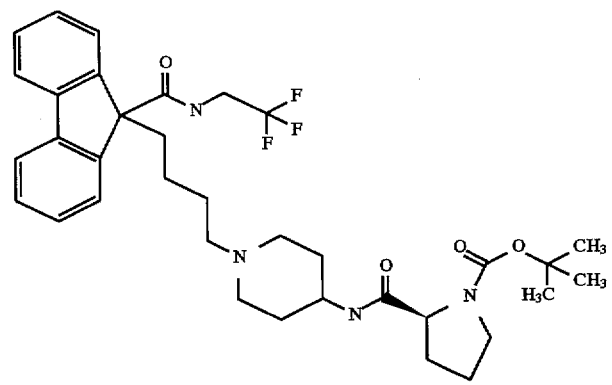
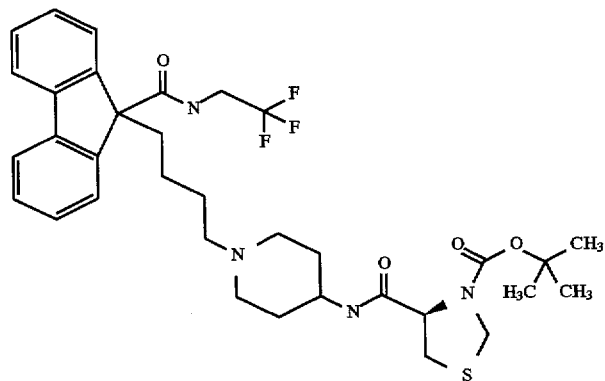

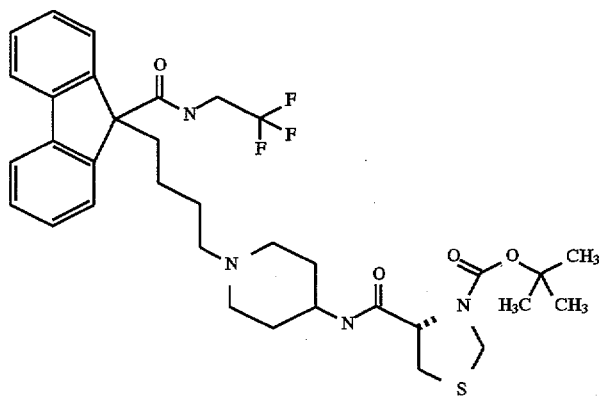
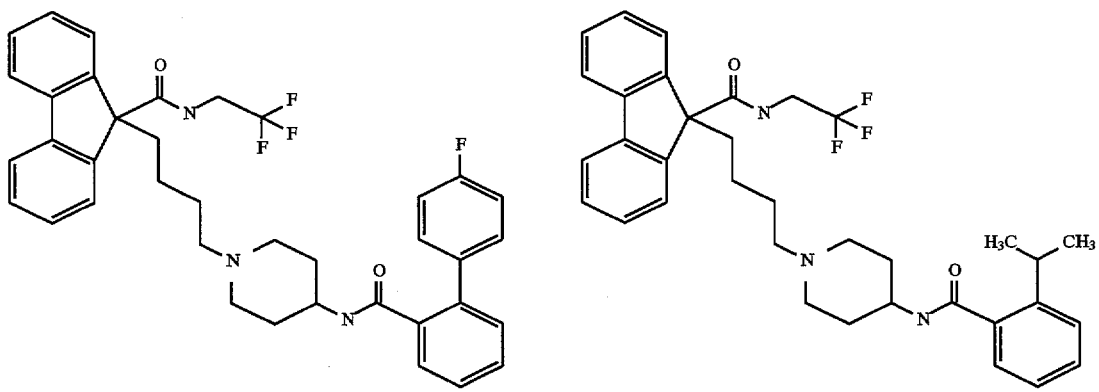
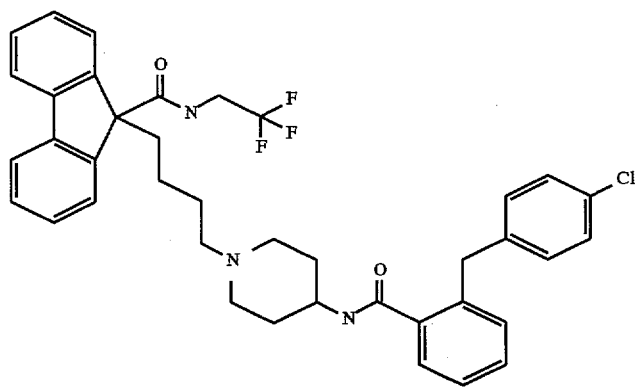
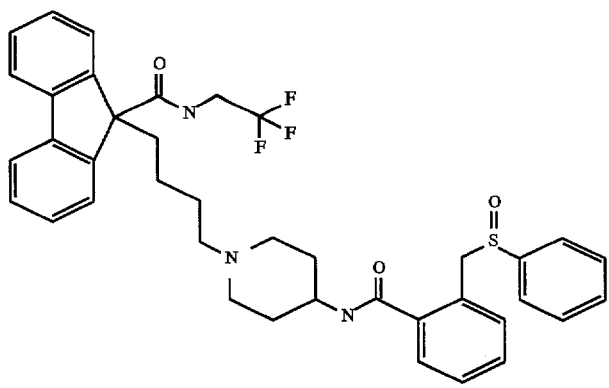

-continued
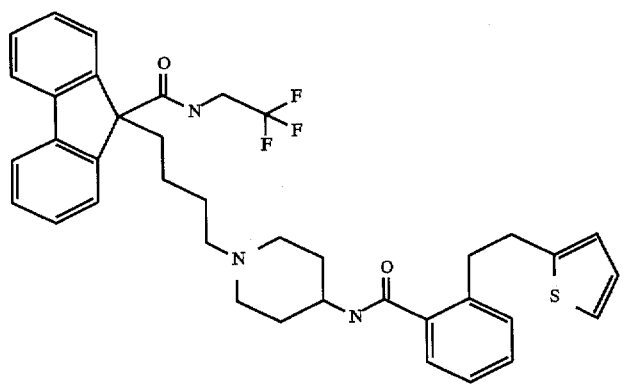
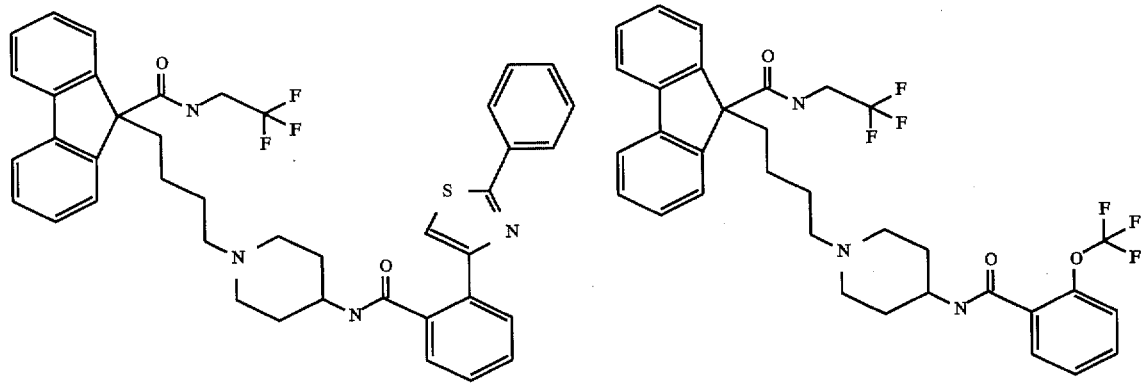
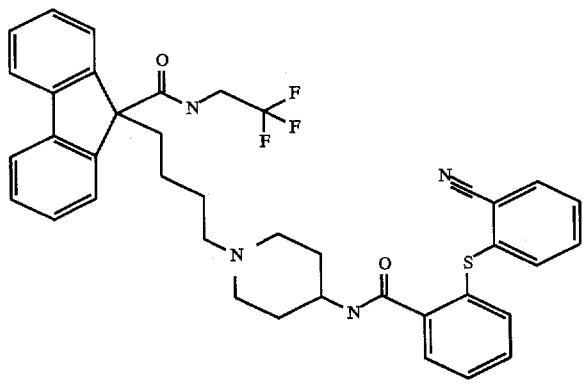
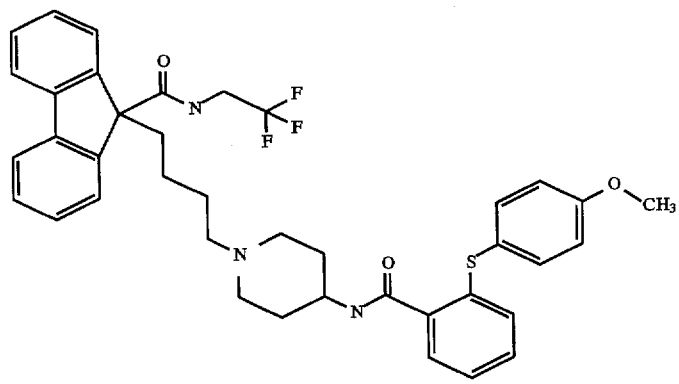

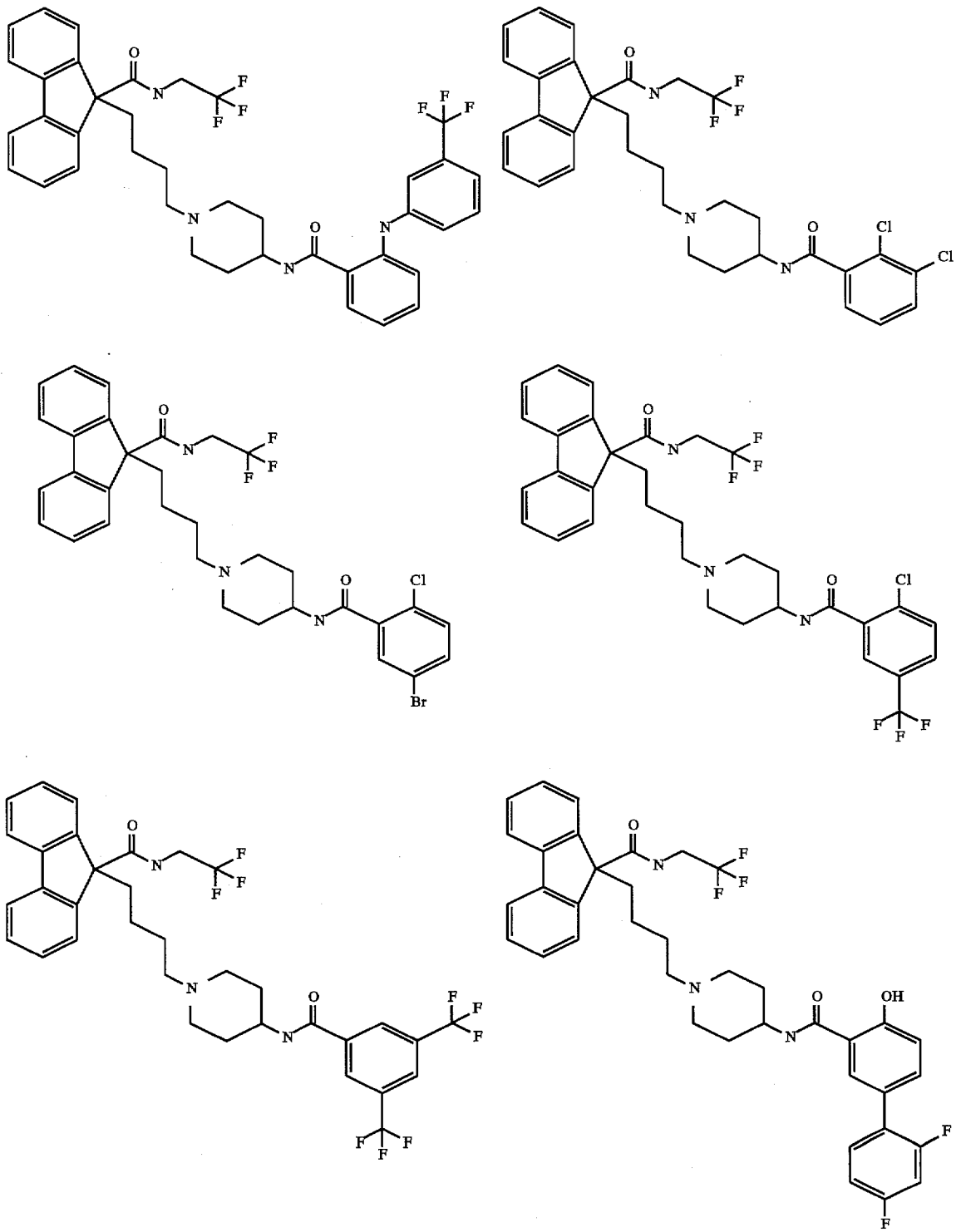

163
164
-continued
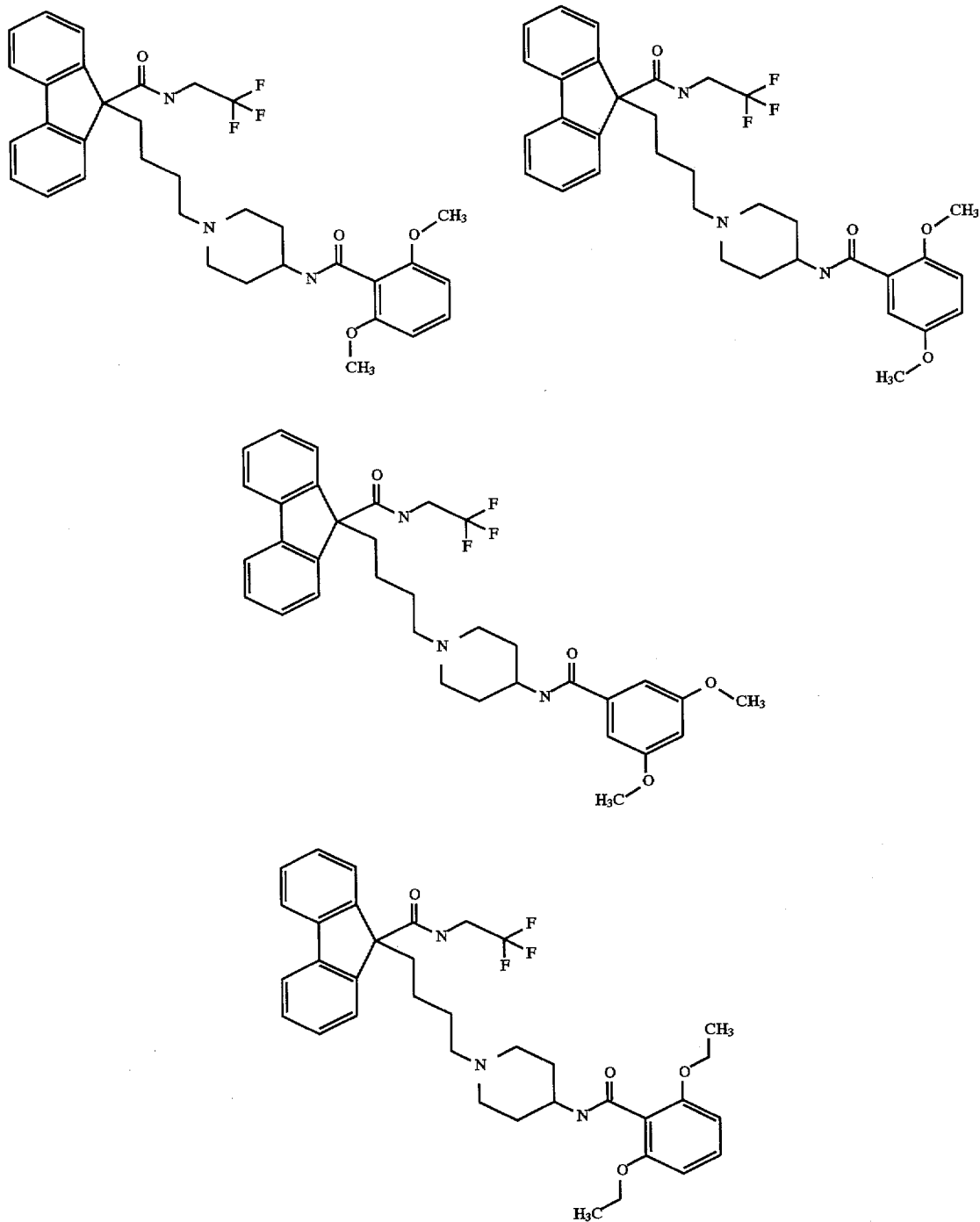

-continued
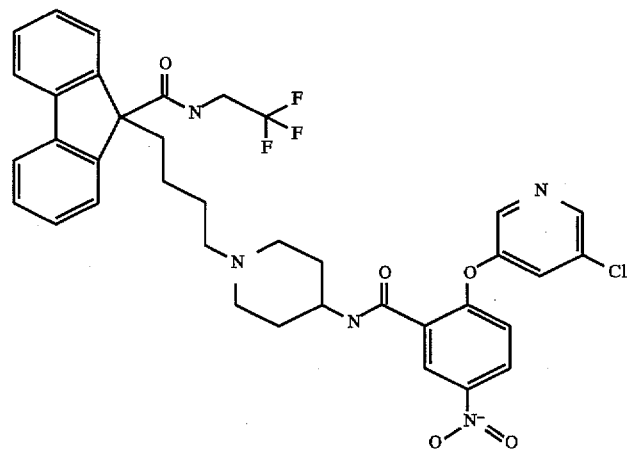
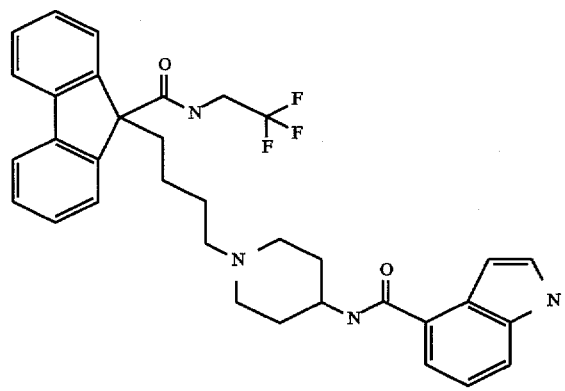
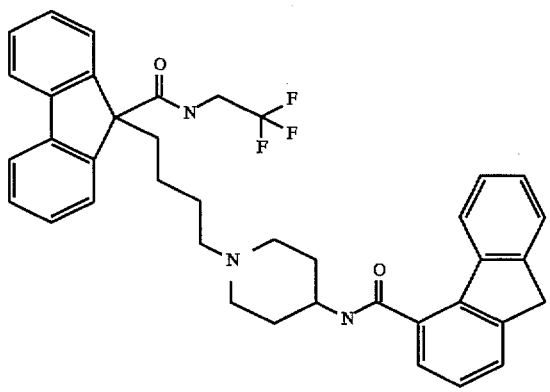
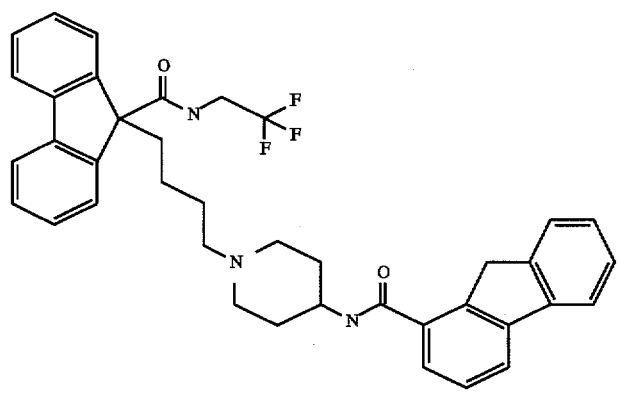
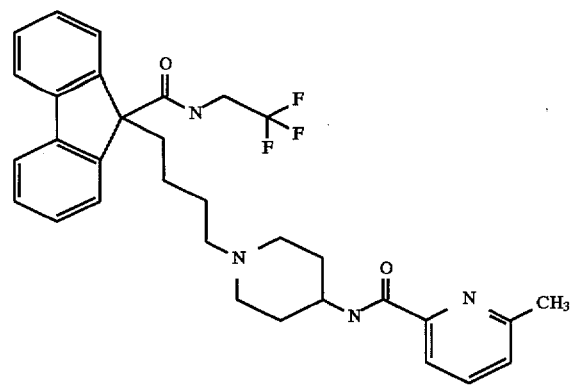

-continued
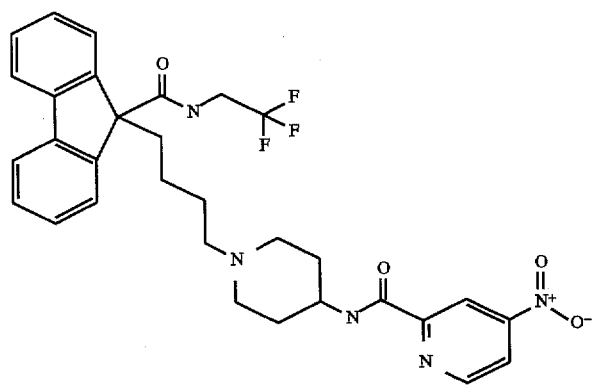
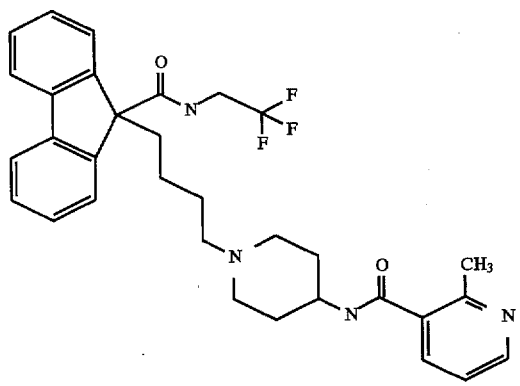
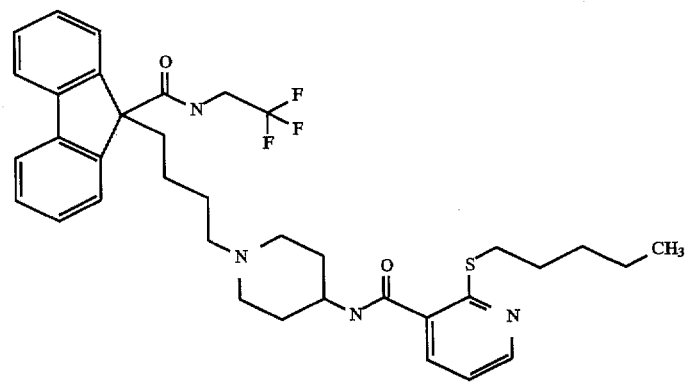
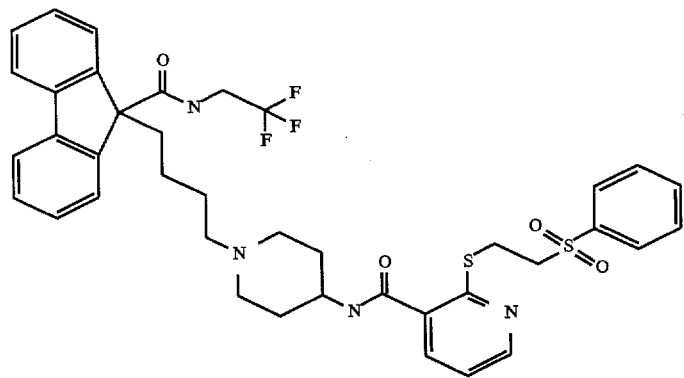

-continued
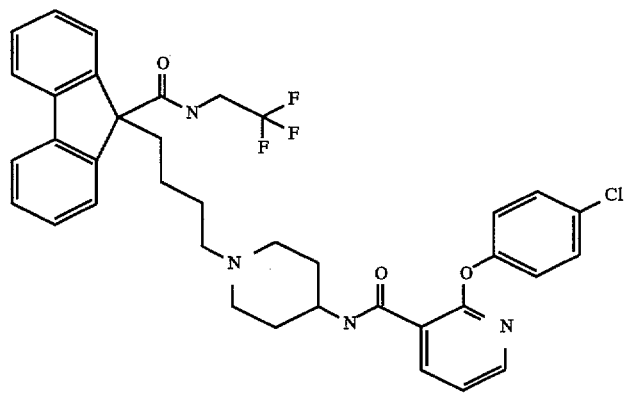
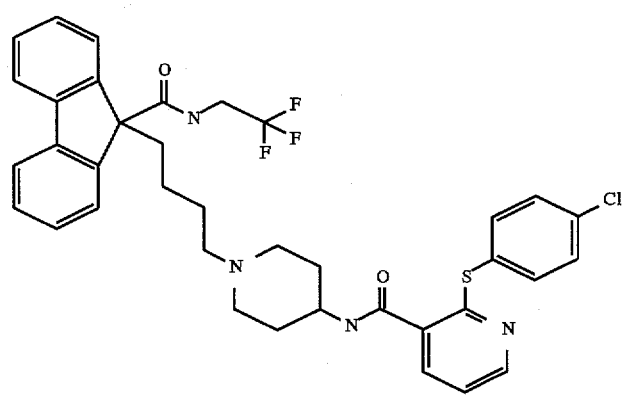
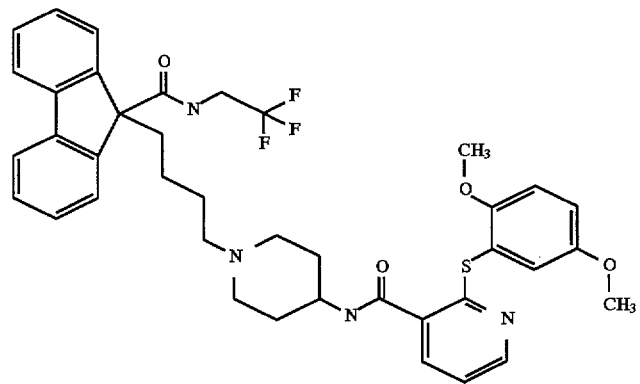
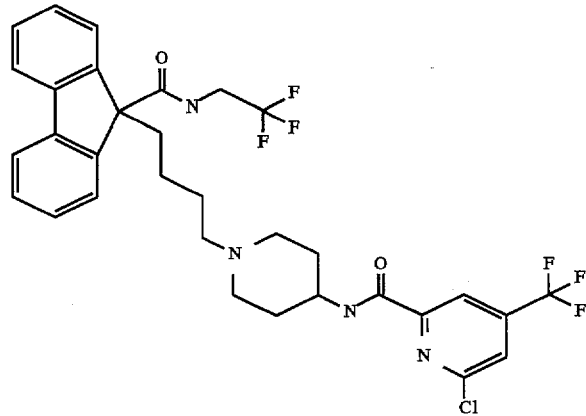

-continued
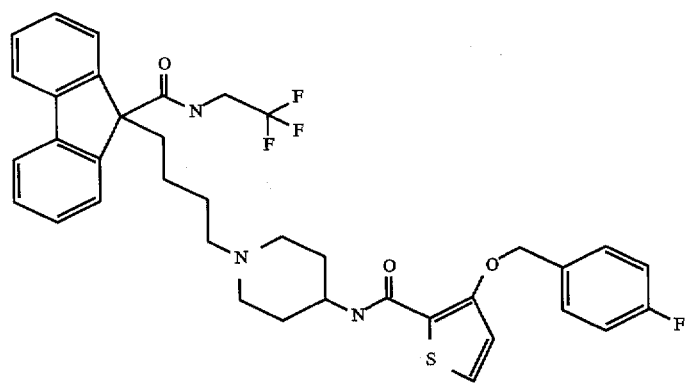
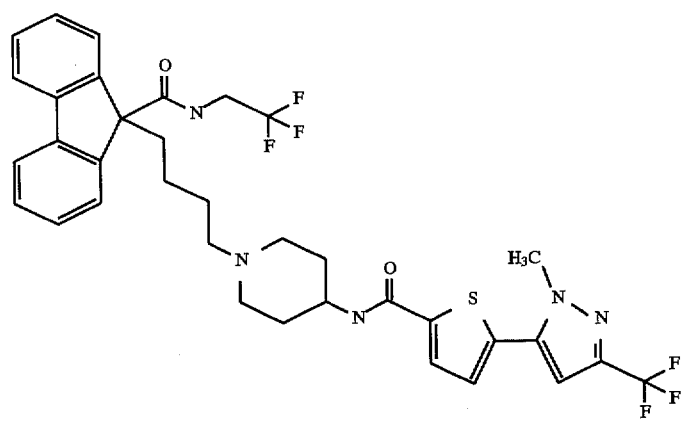
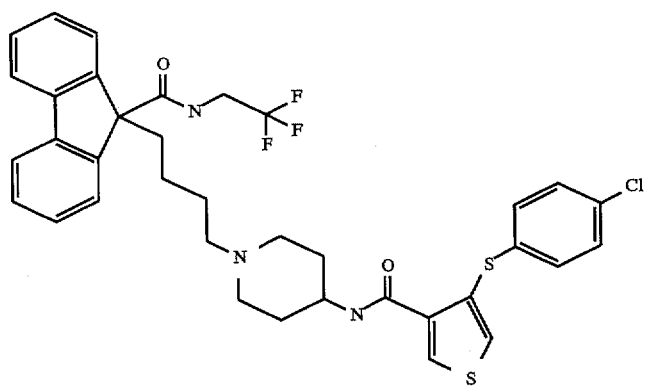
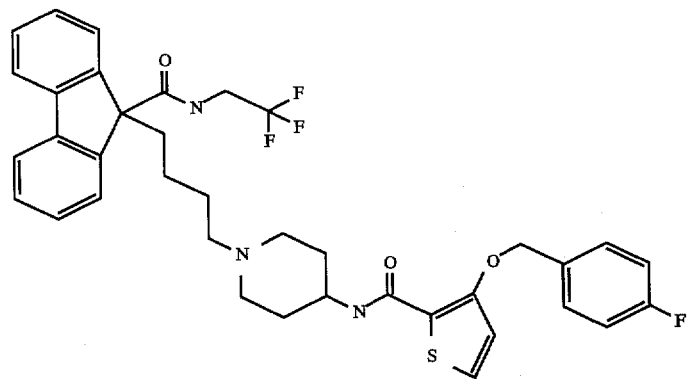

173 174
-continued
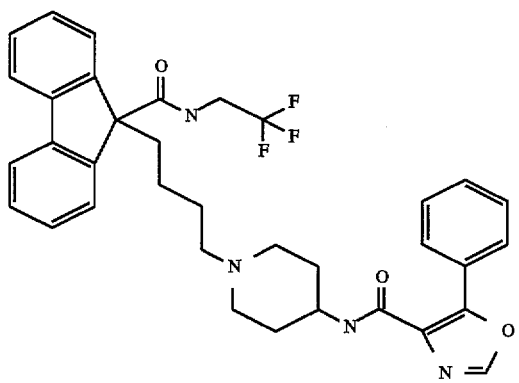
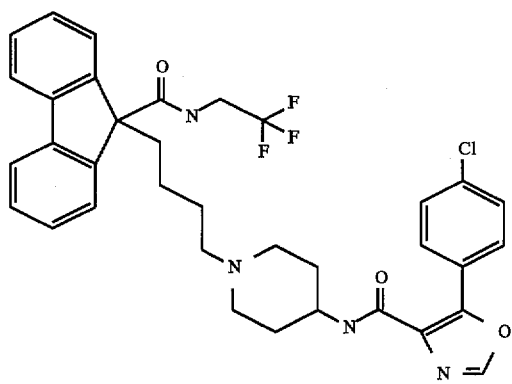
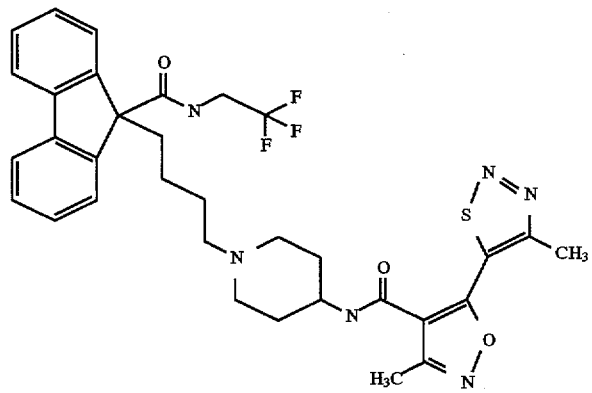
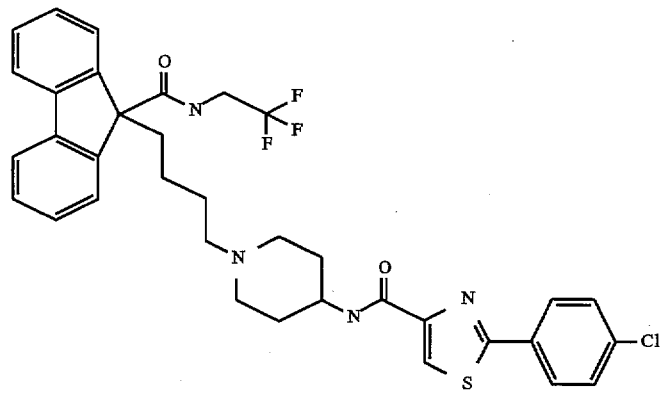
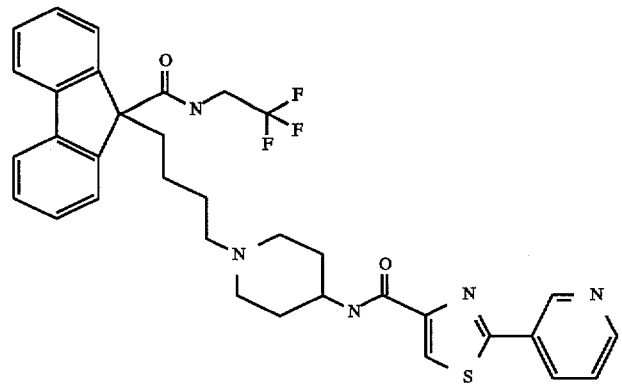

-continued
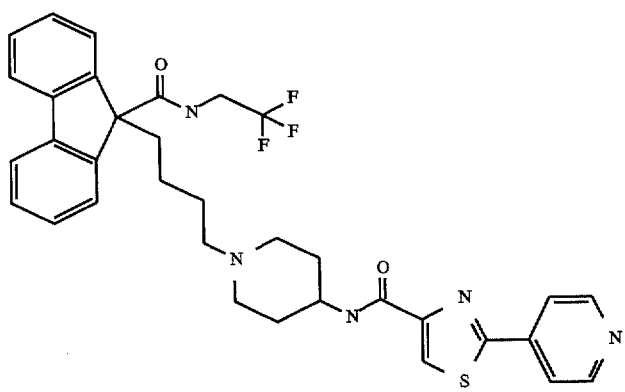
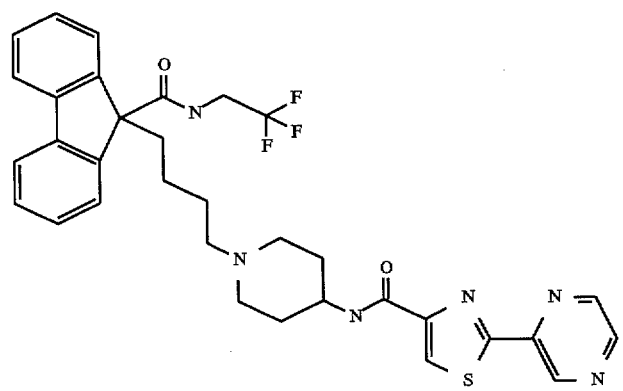
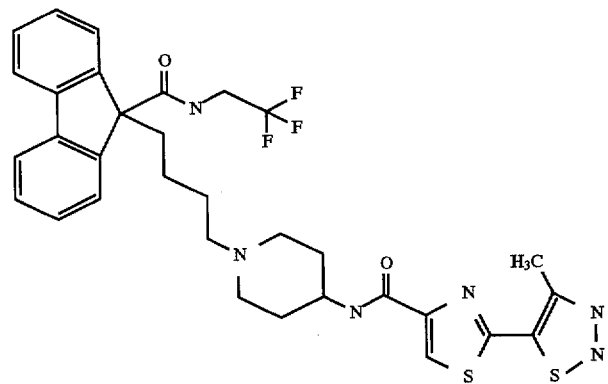
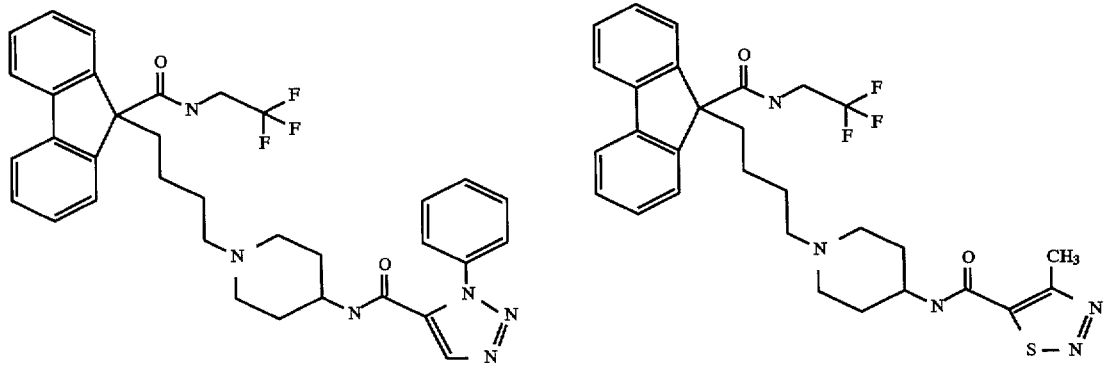

-continued
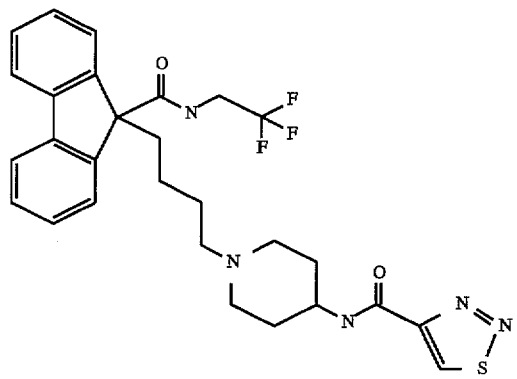
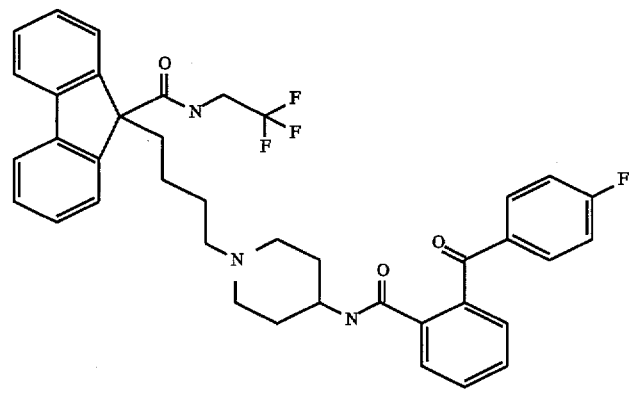
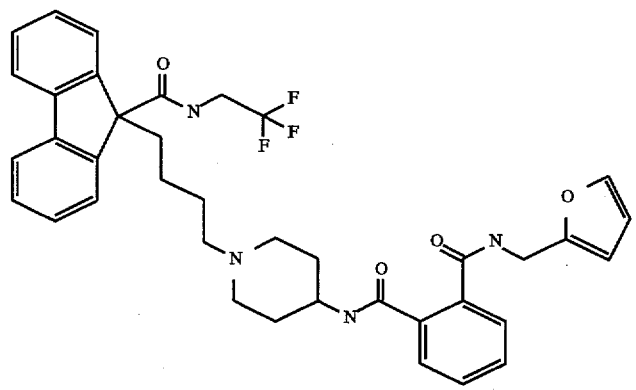
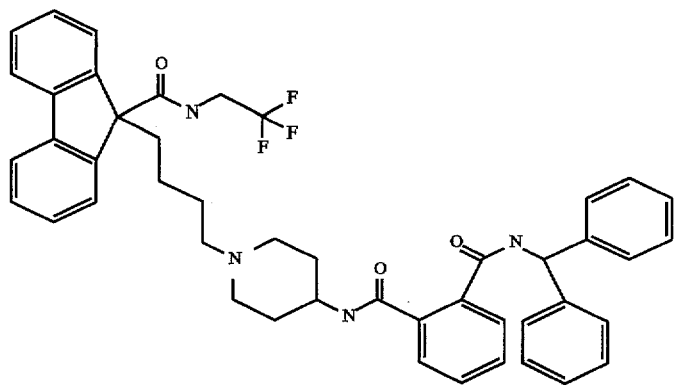

-continued
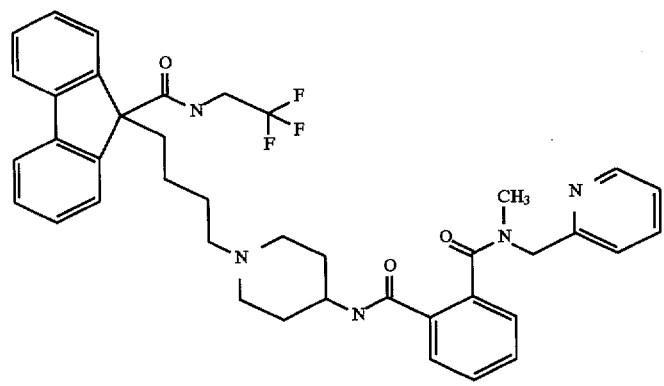
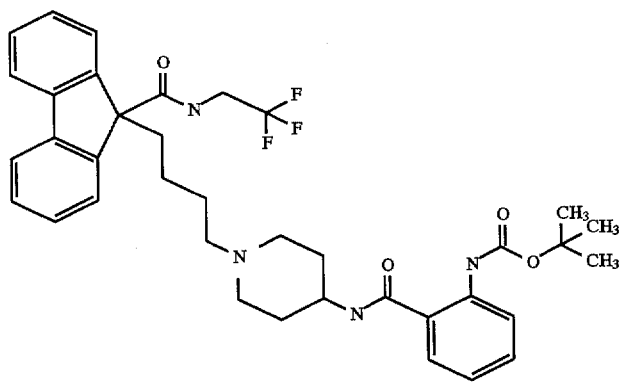
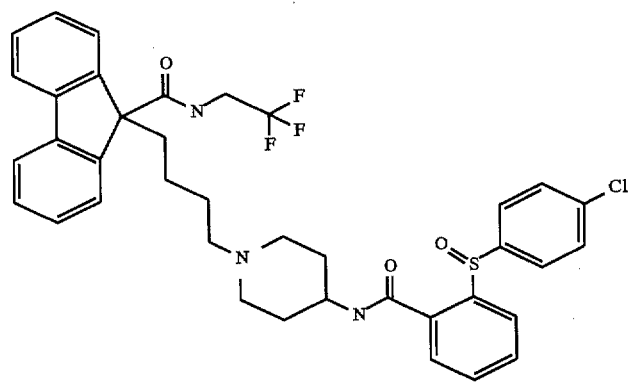
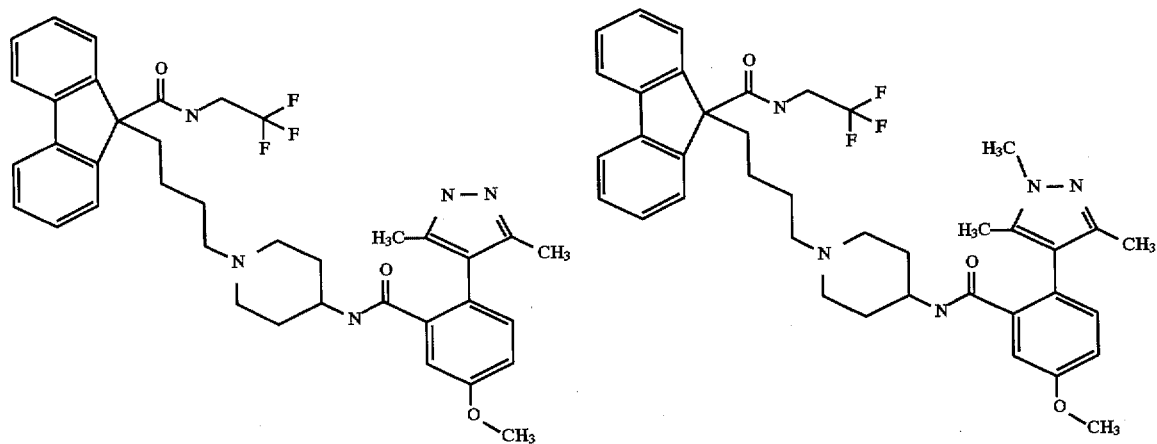

-continued
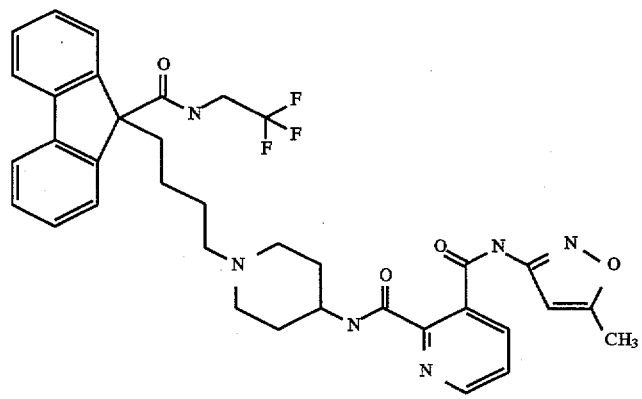
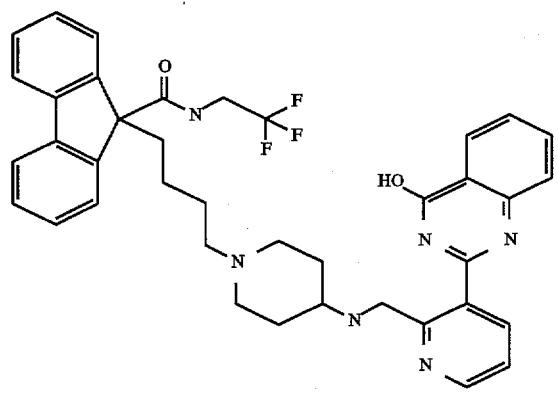
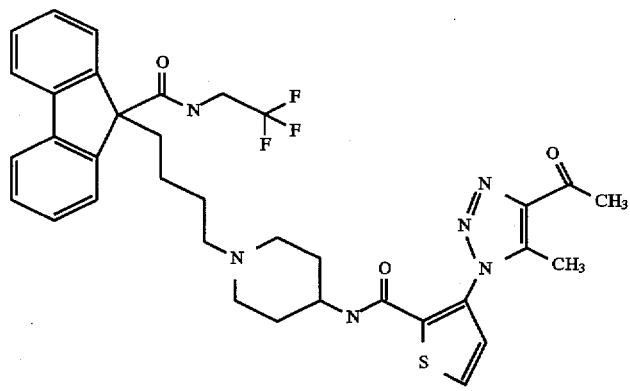
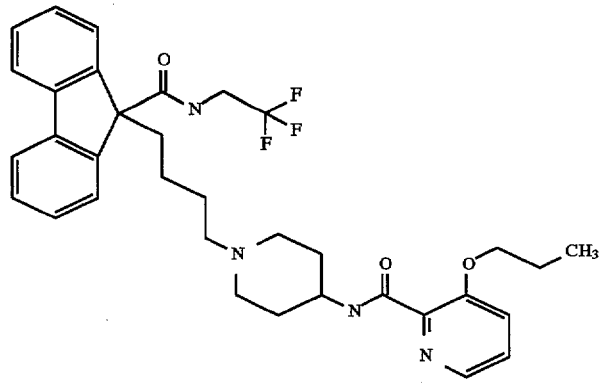

-continued
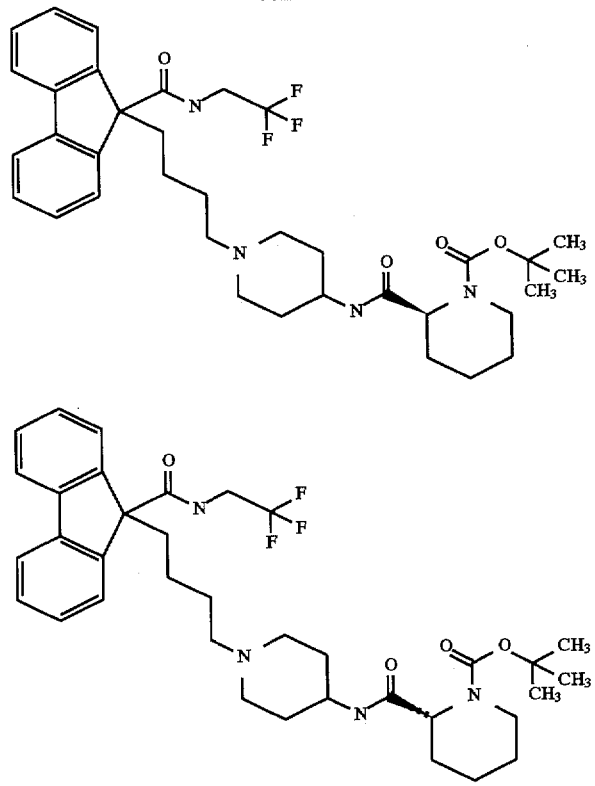
the monohydrochloride thereof, the dihydrochloride thereof or the pharmaceutically acceptable salt thereof.
12. The compound as defined in claim 1 which is
-continued
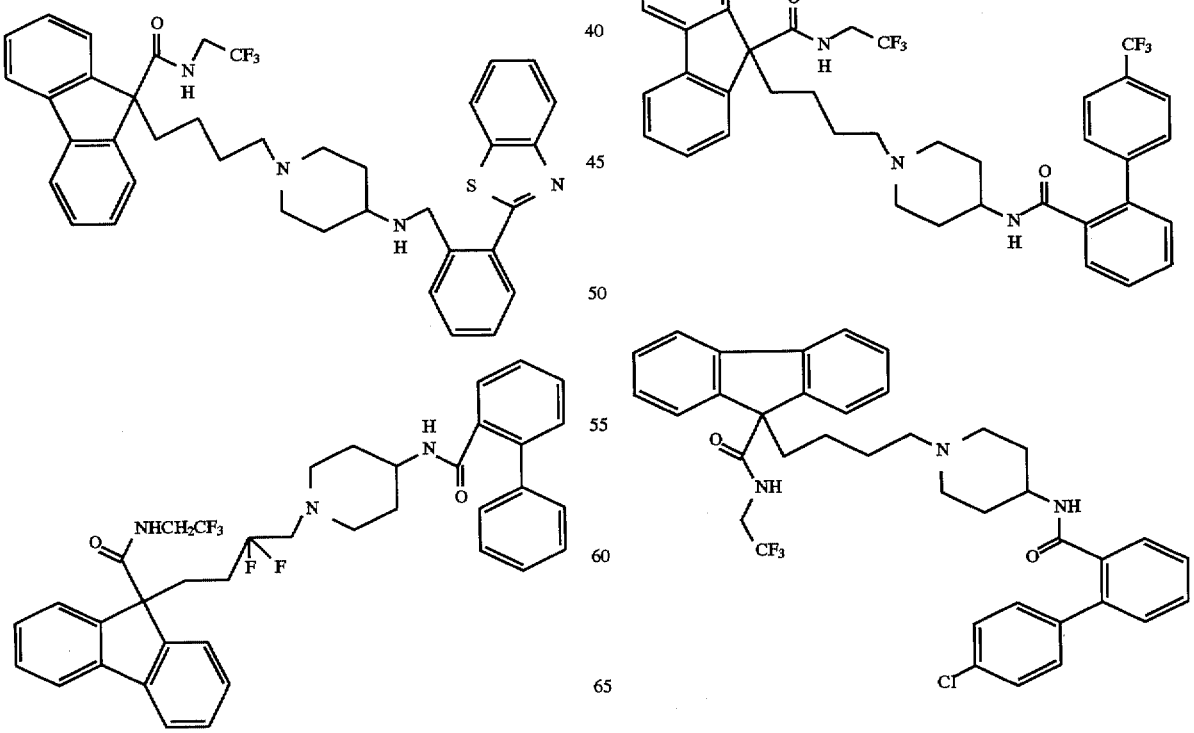

185
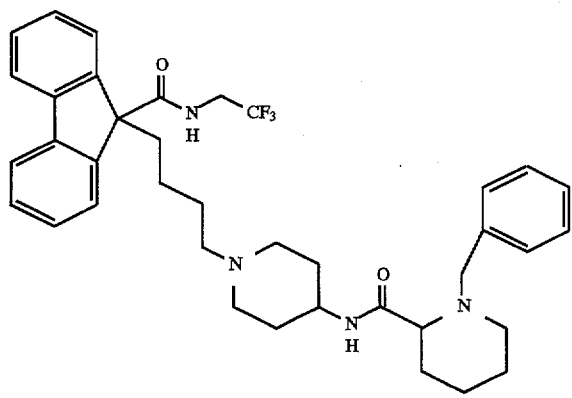
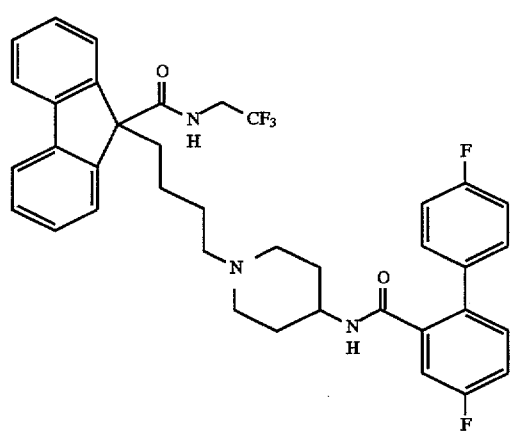
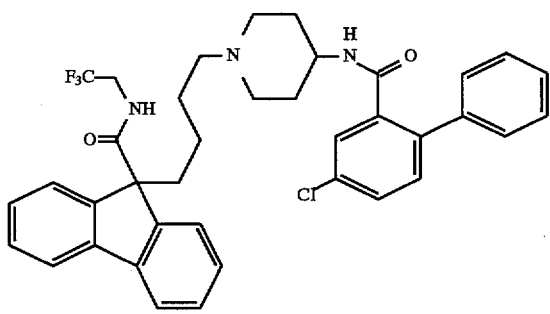
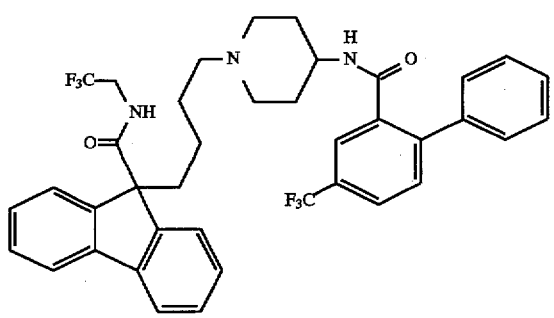
186
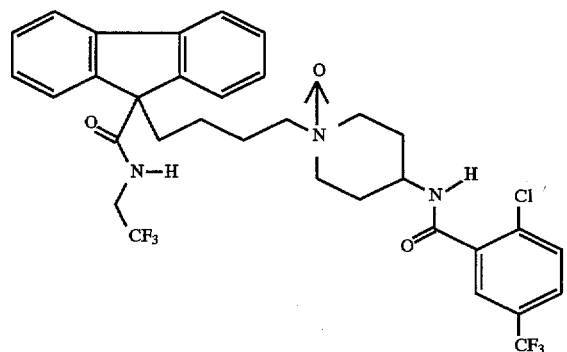
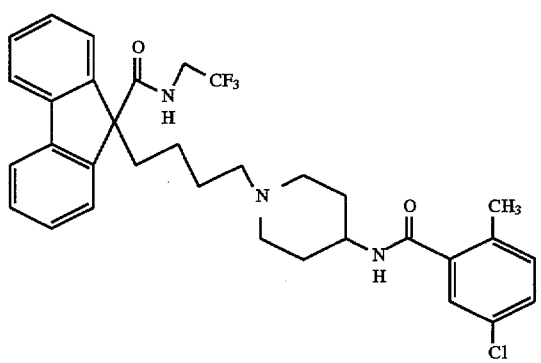
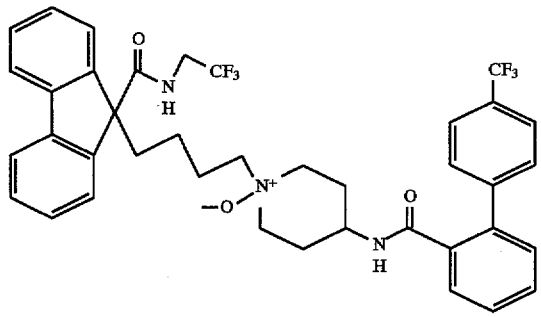
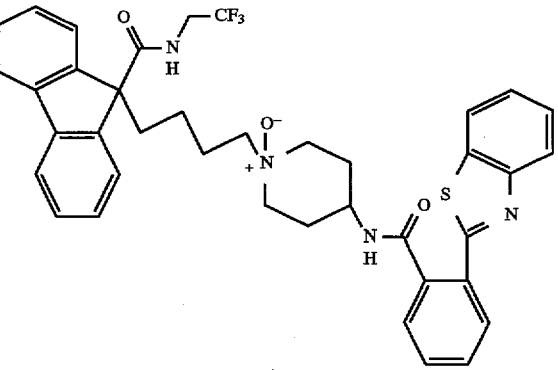

187
-continued
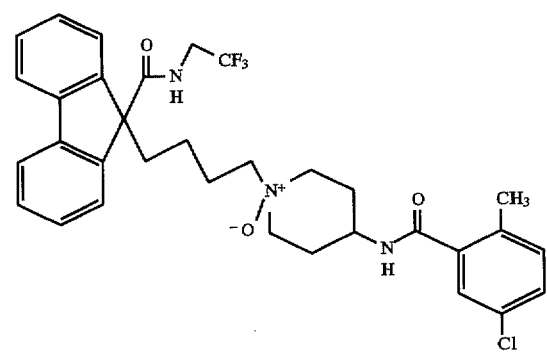
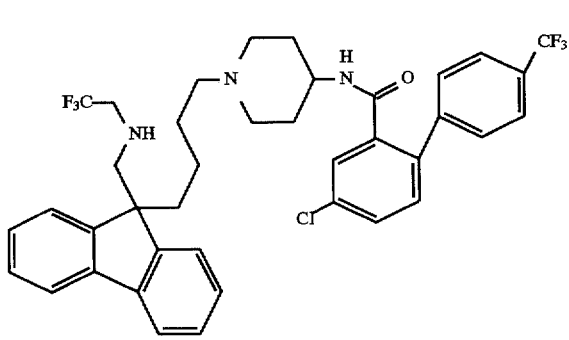
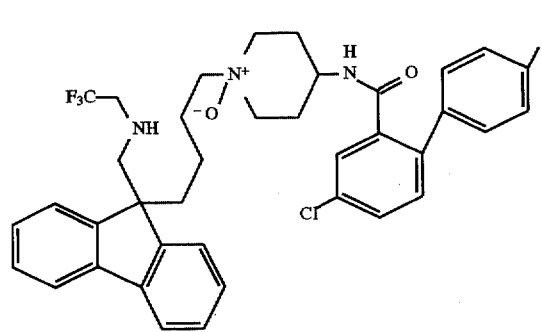
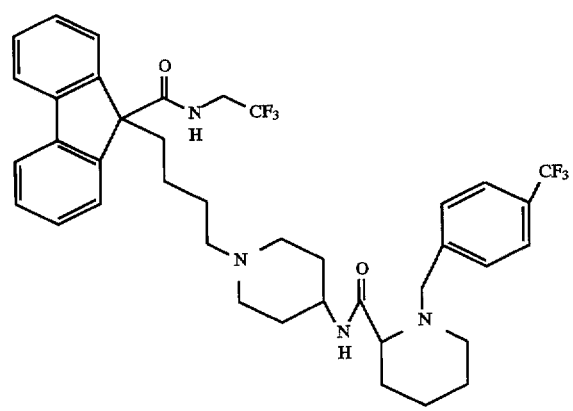
188
-continued
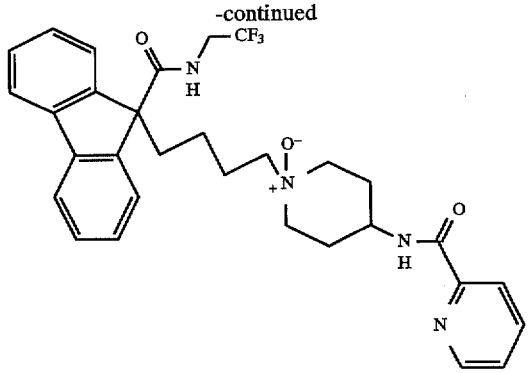
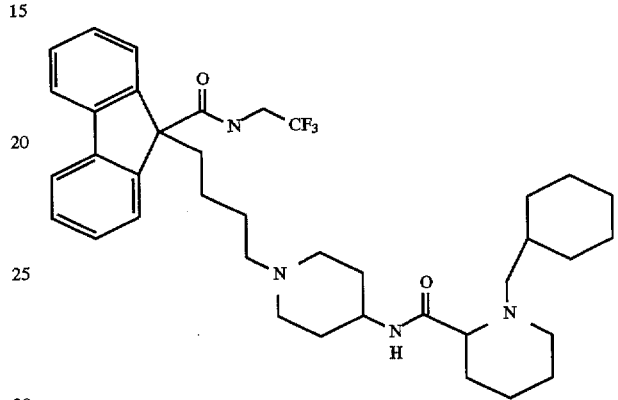
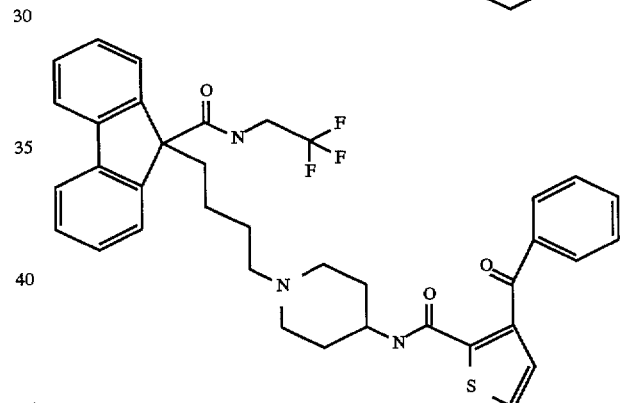
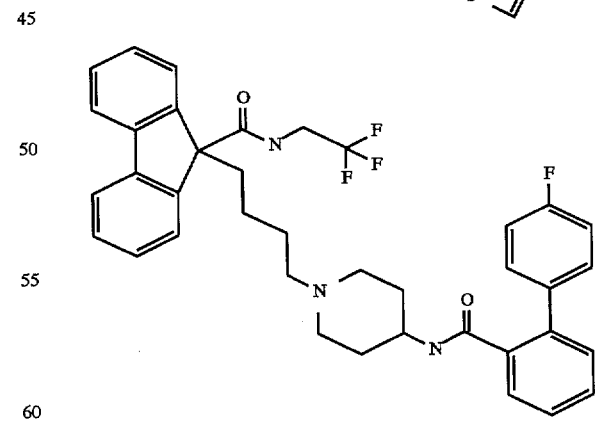

-continued

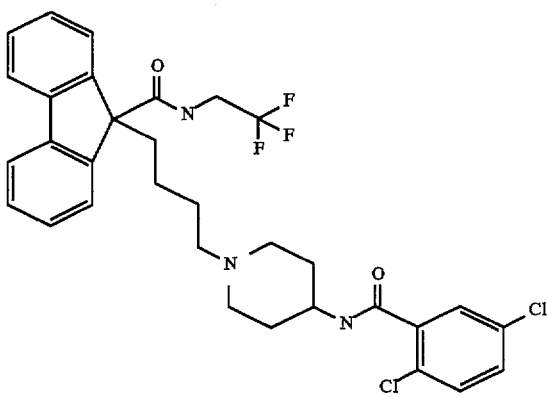

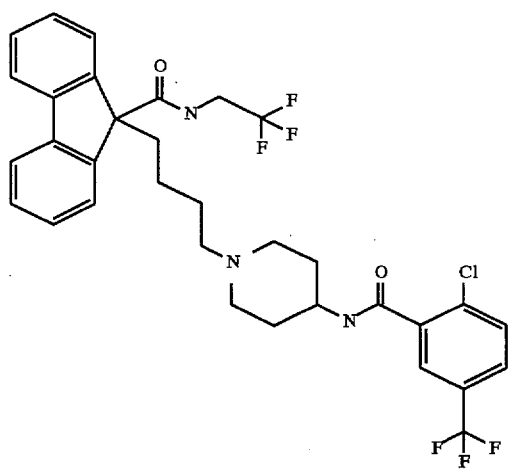

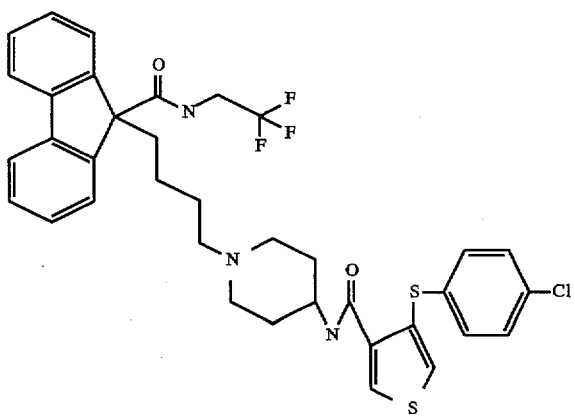

the monohydrochloride thereof, the dihydrochloride thereof or other pharmaceutically acceptable salt thereof.

13. A compound of the structure

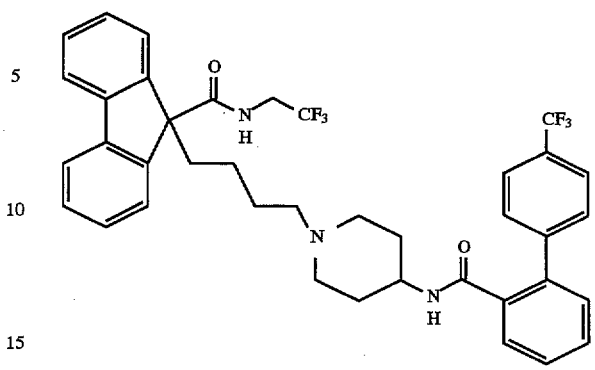

or a pharmaceutically acceptable salt thereof or the piperidine N-oxide thereof.

14. A method for preventing or treating atherosclerosis; pancreatitis secondary to hypertriglyceridemia; hyperglycemia (1) by causing a reduced absorption of dietary fat through MTP inhibition, (2) by lowering triglycerides through MTP inhibition or (3) by decreasing the absorption of free fatty acids through MTP inhibition; or obesity by causing a reduced absorption of dietary fat through MTP, in a mammal species, which comprises administering to a patient in need of treatment a therapeutically effective amount of a compound as defined in claim 1 or 13.

15. A method of lowering serum lipid levels, cholesterol and/or triglycerides, or preventing and/or treating hyperlipemia, hyperlipidemia, hyperlipoproteinemia, hypercholesterolemia and/or hypertriglyceridemia, which comprises administering to a patient in need of treatment a therapeutically effective amount of a compound as defined in claim 1 or 13.

16. A compound having the structure

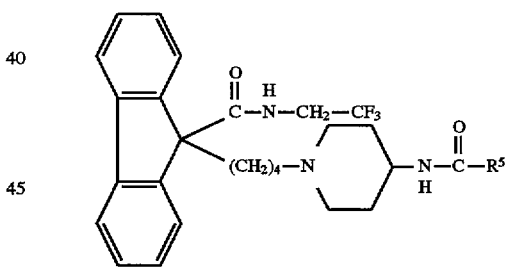

including the piperidine N-oxide thereof or a pharmaceutically acceptable salt thereof, $R^5$ is heteroaryl, aryl, heterocycloalkyl or cycloalkyl, each $R^5$ group being optionally substituted with 1, 2, 3 or 4 substituents which may be the same or different wherein a substituent on $R^5$ is adjacent to a ring carbon attached to the

group.

17. The compound as defined in claim 16 wherein $R^5$ is phenyl substituted with haloalkylphenyl or heteroaryl.
18. The compound as defined in claim 17 wherein $R^5$ is
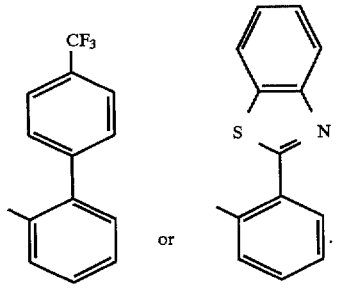
19. The compound as defined in claim 16 having the structure
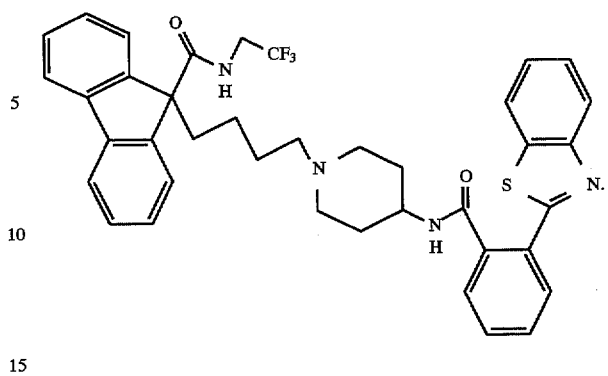
* * * * *